United States Patent [19]
Peel et al.

[11] Patent Number: 4,617,937
[45] Date of Patent: Oct. 21, 1986

[54] BLOOD PRESSURE MONITORING SYSTEM

[75] Inventors: Harry H. Peel; John S. Brisco; Mark E. Moczygemba; Robert L. Neatherlin; Brenda A. Sargent, all of San Antonio, Tex.

[73] Assignee: Nippon Colin, Komaki, Japan

[21] Appl. No.: 778,290

[22] Filed: Sep. 20, 1985

Related U.S. Application Data

[63] Continuation of Ser. No. 702,226, Feb. 21, 1985, abandoned.

[51] Int. Cl.⁴ ............................................. A61B 5/02
[52] U.S. Cl. .................................... 128/680; 128/682; 128/683
[58] Field of Search .............................. 128/680–683, 128/709, 696, 691

[56] References Cited

U.S. PATENT DOCUMENTS

| | | | |
|---|---|---|---|
| 4,245,648 | 1/1981 | Trimmer et al. | 128/689 X |
| 4,396,018 | 8/1983 | Sibley | 128/680 |
| 4,423,738 | 1/1984 | Newgard | 128/672 |
| 4,425,920 | 1/1984 | Bourland et al. | 128/691 X |
| 4,448,202 | 5/1984 | Wajzcuk et al. | 128/709 |

Primary Examiner—William E. Kamm
Assistant Examiner—Francis J. Jaworski
Attorney, Agent, or Firm—Hubbard, Thurman, Turner & Tucker

[57] ABSTRACT

A blood pressure monitoring system is disclosed for monitoring blood pressure during stress testing or other physical activity as well as when quiescent. The blood pressure monitoring system of the present invention includes an inflatable cuff utilized in conjunction with a controllable electric air pump and deflation valve. Audio transducers are utilized to detect pulse sound at the proximal and distal edges of the inflatable cuff and pulse sound amplitudes as well as the time delay between pulse sounds proximal to the cuff and distal to the cuff are determined. Pulse sound amplitudes are then multiplied by time delay values for selected cuff pressures to generate a greatly enhanced blood pressure evaluation curve. In a preferred mode of the present invention digital filters and statistical analysis are then employed to determine systolic and diastolic blood pressure from the evaluation curve. Further novel features of the blood pressure monitoring system of the present invention include the ability of the system to select a trigger signal from multiple electrocardiographic leads by selecting the particular electrocardiographic lead with the least amount of noise present and the capability of modifying the inflation pressure and deflation rate of the cuff to permit either maximum accuracy or minimum measurement time during operation.

34 Claims, 10 Drawing Figures

BLOOD PRESSURE MONITORING SYSTEM

This application is a continuation, of application Ser. No. 702,226 filed 2/21/85 now abandoned.

BACKGROUND OF THE INVENTION

This invention relates to blood pressure measurement in general and in particular to automatic blood pressure monitoring systems. Still more particularly, this invention relates to methods and apparatus for accurately monitoring blood pressure during stress testing or other physical activity as well as when quiescent.

One of the major medical problems facing the public today is associated with the lack of control of abnormal blood pressure. Indeed, hypertension is a leading cause of disease and death in the United States and it has been estimated that over fifteen percent of the United States population has hypertension at present, controlled by intermittent oral therapy or emergency intravenous medication.

For control of abnormal blood pressure, accurate and dependable measurement of blood pressure is necessary both to determine the presence of a problem and for monitoring the pressure to assure alleviation or control of such problem. In particular, it is highly useful for the medical practitioner to determine a patient's blood pressure during physical activity such as during a diagnostic stress test; however, such testing generally results in severe and frequent arm motions which generate a large number of false signals known as motion artifacts.

As a result of the problems generated by these motion artifacts, numerous attempts have been made to provide an apparatus for measuring systolic and diastolic blood pressure during such testing in which artifact information may be substantially eliminated from Korotkov sound signals which are employed to determine blood pressure. One example of such a system is disclosed in U.S. Pat. No. 4,408,614, issued to Charles S. Weaver et al. Weaver et al provides an automatic computer-implemented technique for identifying and eliminating false outputs from a Korotkov sound detector included in a blood pressure measuring system or the like which is adapted for use during stress testing. The Weaver et al patent discloses a method by which a group of points of data may be operated on to delete suspected artifact points and enhance the accuracy of blood pressure measurement.

A second example of blood pressure measurement is disclosed in U.S. Pat. No. 4,425,920, issued to Bourland et al. Bourland et al discloses an apparatus and method for the measurement and control of blood pressure in which blood pressure is indirectly monitored without the use of a pressure transducer by sensing the pulse transit time to different sites within an artery. The transit time is inversely related to the blood pressure and pulses which are developed therefrom are utilized to form arterial pulse waves, the comparison between which provides an indication of measured blood pressure.

While known systems do generally provide some degree of enhanced accuracy due to partial elimination of motion artifact, it is generally accepted that an improved blood pressure monitoring system which may be utilized during diagnostic stress testing would be highly desired.

SUMMARY OF THE INVENTION

It is therefore one object of the present invention to provide an improved blood pressure monitoring system.

It is another object of the present invention to provide an improved blood pressure monitoring system which minimizes false outputs caused by motion artifacts.

It is still another object of the present invention to provide an improved blood pressure monitoring system which permits variable deflation of the blood pressure cuff to permit maximum accuracy or minimum measurement time.

It is another object of the present invention to provide an improved blood pressure monitoring system which includes means for selecting one of a plurality of electrocardiographic Leads to be utilized as a trigger signal by analyzing the signal to noise ratio of each electrocardiographic Lead.

It is still another object of the present invention to provide an improved blood pressure monitoring system which selects the inflation pressure, deflation rate, and exhaust pressure of the blood pressure cuff based upon previous measurements of the patient's systolic and diastolic blood pressure.

The foregoing objects are achieved as is now described. The blood pressure monitoring system of the present invention includes an inflatable cuff utilized in conjunction with a controllable electric air pump and deflation valve. Audio transducers are utilized to detect pulse sound at the proximal and distal edges of the inflatable cuff and pulse sound amplitudes as well as the time delay between pulse sounds proximal to the cuff and distal to the cuff are determined. Pulse sound amplitudes are then multiplied by time dealy values for selected cuff pressures to generate a greatly enhanced blood pressure evaluation curve. In a preferred mode of the present invention digital filters and statistical analysis are then employed to determine systolic and diastolic blood pressure from the evaluation curve. Further novel features of the blood pressure monitoring system of the present invention include the ability of the system to select a trigger signal from multiple electrocardiographic Leads by selecting the particular electrocardiographic Lead with the least amount of noise present and the capability of modifying the inflation pressure and deflation rate of the cuff to permit either maximum accuracy or minimum measurement time during operation.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
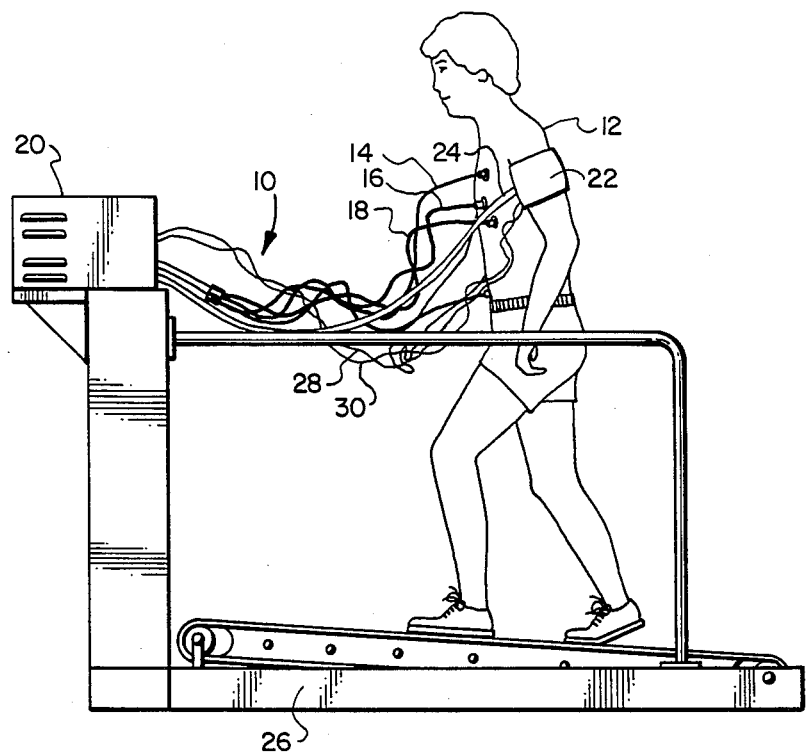
FIG. 1 depicts a diagrammatic view of a patient undergoing a diagnostic stress test utilizing the blood pressure monitoring system of the present invention.

With reference now to the figures and in particular with reference to FIG. 1, there is depicted a diagrammatic view of a patient stress test utilizing blood pressure monitoring system 10 of the present invention. As can be seen, blood pressure monitoring system 10 includes an electronic unit 20 which is coupled to patient 12 utilizing a plurality of electrocardiographic electrodes 32, 33, 34 and 36 and which also includes an inflatable cuff 22. Flexible air tube 24 is coupled to inflatable cuff 22 and is utilized in conjunction with an electric air pump (not shown) and a controllable deflation valve (not shown) to inflate and deflate inflatable cuff 22 within a range of pressures within which Korotkov sounds are produced. As is typical in diagnostic stress testing, patient 12 is depicted walking on a treadmill 26 and in all probability, the patient's arms will be moving, generating so-called "artifact noise" which will render accurate measurement of blood pressure highly difficult. Concealed within inflatable cuff 22 are two audio transducers (not shown) which are utilized to convert pulse sounds to electric signals. These signals are then coupled to electronic unit 20 by means of wires 28 and 30, as will be illustrated herein.

Figure 2:
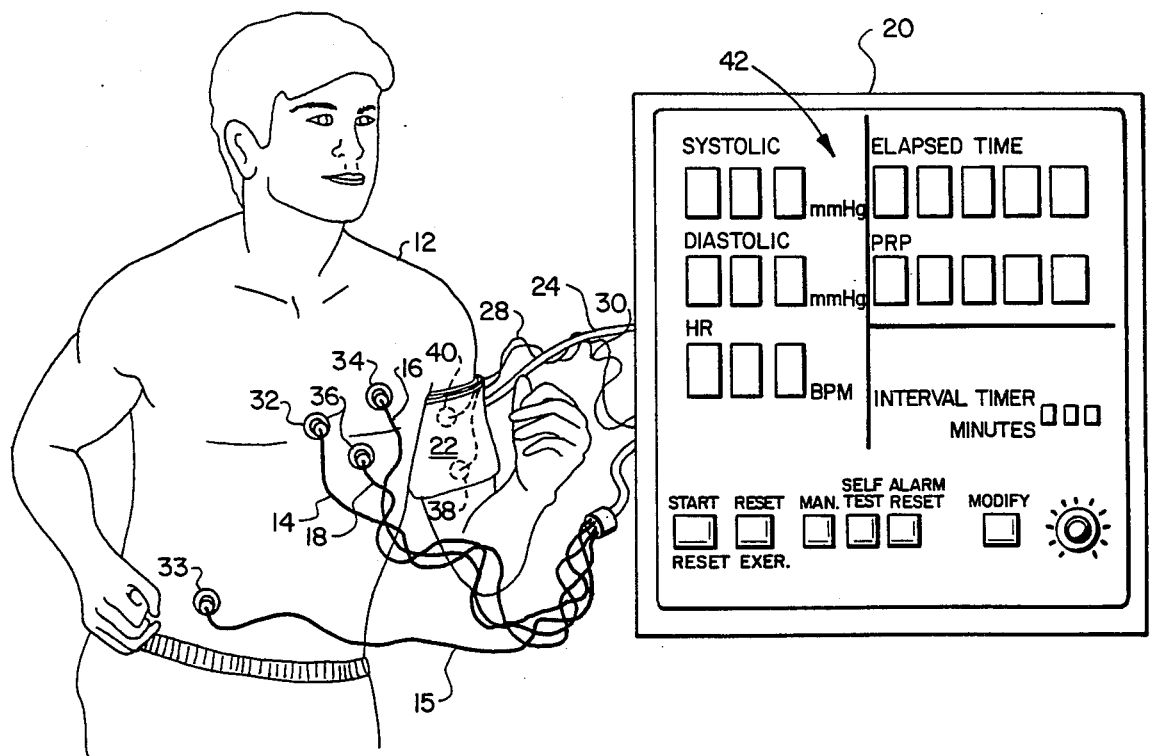
FIG. 2 depicts an enlarged view of the electronic unit of the blood pressure monitoring system of the present invention which illustrates the connections between the patient and the blood pressure monitoring system of the present invention.

Referring now to FIG. 2, there is depicted an enlarged view of electronic unit 20 of blood pressure monitoring system 10 of the present invention which clearly demonstrates the connections between patient 12 and blood pressure monitoring system 10. As may be seen clearly, electrocardiographic electrodes 32, 33, 34 and 36 are coupled to electronic unit 20 by means of wires 14, 15, 16 and 18 and serve to generate three electrocardiographic Lead signals. As will be explained in greater detail herein, electronic unit 20 then selects an optimum Lead from among the electrocardiographic Leads to be utilized as a trigger signal. Depicted within inflatable cuff 22 are two audio transducers 40 and 38. Audio transducer 40 is referred to as the proximal audio transducer and is located near or proximate to the patient's body, along the proximal edge of inflatable cuff 22. Audio transducer 38 is referred to as the distal audio transducer and is located away from the patient's body along the distal edge of inflatable cuff 22. As can be seen, electronic unit 20 includes a front panel 42 upon which systolic and diastolic pressure as well as elapsed time, pulse rate and interval between blood pressure measurements may be displayed. Additionally, electronics unit 20 also includes a plurality of switches which permit the various modes of operation to be selected.

Figure 3:
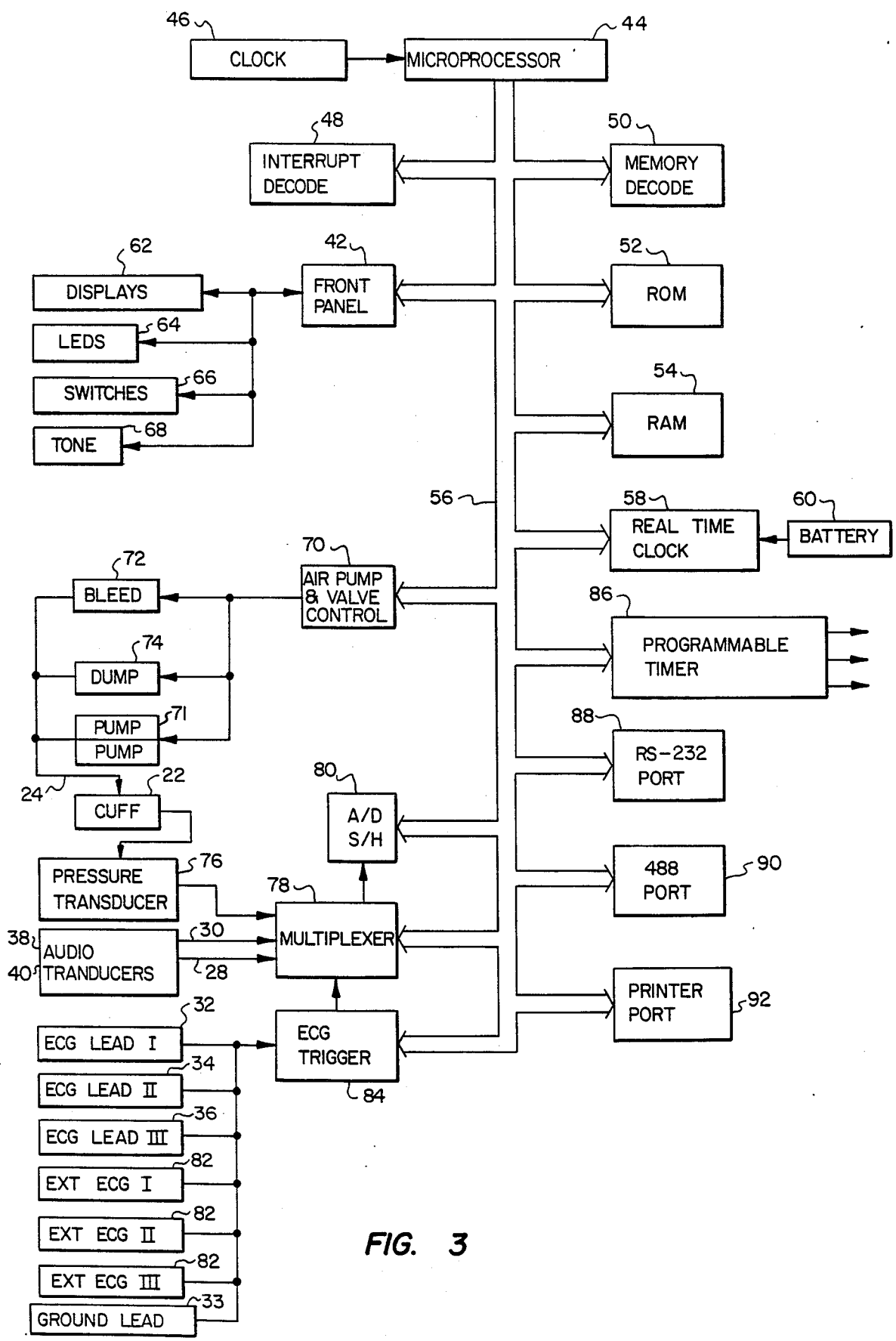
FIG. 3 depicts a block diagram of the blood pressure monitoring system of the present invention.

With reference now to FIG. 3, there is depicted a simplified block diagram of blood pressure monitoring system 10 of the present invention. Where possible, the elements within the block diagram of FIG. 3 have been given the same reference numerals as utilized in FIGS. 1 and 2. As can be seen, blood pressure monitoring system 10 utilizes a microprocessor to control the operation of the system. In a preferred embodiment of the present invention, microprocessor 44 is an MC68000 microprocessor and is utilized in conjunction with clock 46 which provides an 8 megahertz clock output. Interrupt decode 48 and memory decode 50 are utilized in conjunction with microprocessor 44. Interrupt decode 48 includes interrupt decode logic and system reset logic. Memory decode 50 is utilized to permit data stored in memory to be addressed and buffered for access by microprocessor 44.

Microprocessor 44 is capable of addressing both read-only-memory 52 and random-access-memory 54. In a preferred embodiment of the present invention, 128 K bytes are provided in both read-only-memory and random-access-memory. A real-time clock is provided and coupled to microprocessor 44 along bus 56. Real-time clock 58 is utilized to permit the actual time and date of a particular test to be stored in memory with the data resulting from that test. A battery 60 is also provided to ensure that real-time clock 58 does not need to be periodically reset should power to blood pressure monitoring system 10 be interrupted.

As disclosed in FIG. 2, the front panel 42 of electronic unit 20 includes both displays 62, LED indicators 64 and switches 66 which permit the various modes of operation to be selected. Additionally, a tone generator 68 is provided and is utilized to generate an alarm tone under alarm conditions.

Air pump and valve control module 70 are utilized to inflate and deflate inflatable cuff 22. Air pump and valve control module 70 preferably controls two electric air pumps 71 and valves, such as the pump and valve module Model No. FN30-S4668, manufactured by Cannon Seiki of Japan. Additionally, a bleed valve 72 and dump valve 74 are provided to permit the pressure within inflatable cuff 22 to be slowly bled off or rapidly dumped in the event that the process must begin again rapidly or the measurement has been completed.

Outputs from pressure transducer 76 and audio transducer 38 and 40 which represent the pressure within inflatable cuff 22 and the presence of pulse sounds detected by audio transducers 38 and 40 are coupled to multiplexer 78 which is preferably a sixteen channel multiplexer which includes analog signal conditioning circuitry, channel decode logic and analog control logic. The output of multiplexer 78 is then passed to a sample and hold circuit and then to a twelve bit analog to digital converter 80.

Electrocardiographic signals from electrodes 32, 34, 36 and ground lead 33 or external electrocardiographic Lead signals 82 may be coupled to electrocardiographic trigger circuit 84. Electrocardiographic trigger circuit 84 consists of the electrocardiographic circuitry and a floating lead detector. The floating Lead detector periodically samples the electrocardiographic Leads for 60

Hertz noise which increases when an electrode becomes detached from the patient. By utilizing a comparison and selection process to select the one electrocardiographic Lead from a plurality of Leads which represents the best signal to generate a trigger signal, blood pressure monitoring system 10 will not fail should an electrocardiographic electrode become dislodged or should an unusual amount of noise be present on a particular Lead. Additionally, this process includes means for detecting the absence or presence of an electrocardiographic signal so that should an electrocardiographic signal be lost electrocardiographic trigger circuit 84 may immediately switch to a second electrocardiographic Lead to continue blood pressure measurement. Additionally, a particular electrocardiographic Lead may be user selected by a programmed switch located on front panel 42.

A programmable timer 86 such as Model MC146818 integrated circuit timer is also provided to permit blood pressure monitoring system 10 to accurately and correctly determine intervals between successive blood pressure measurements. Finally, blood pressure monitoring system 10 also includes several output ports to permit data from blood pressure monitoring system 10 to be coupled to a variety of devices. Included among these output ports are RS-232 port 88 which preferably is implemented utilizing an MC6850 asynchronous communication interface adaptor, baud rate generator and various line drivers and receivers. The baud rate in this device is switch selectable from 50 to 19,200 baud and thus permits data from blood pressure monitoring system 10 to be transmitted serially to another device utilizing a similar port. Next, a general purpose interface circuit which utilizes a standard IEEE-488 connector 90 is also provided to permit blood pressure monitoring system 10 to communicate with additional devices. Finally, a printer output port 92 is also provided so that blood pressure measurement data derived by blood pressure monitoring system 10 may be coupled to a printer to provide hard copy for medical record purposes.

Figure 4A:
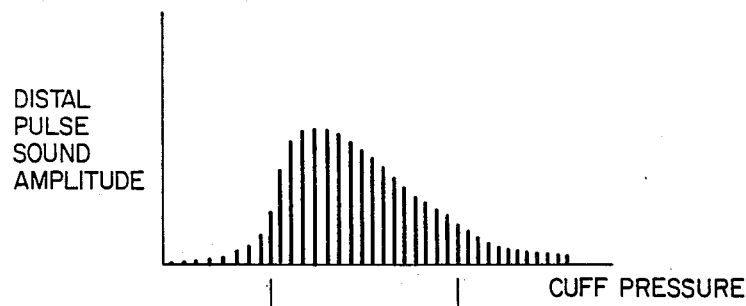
FIG. 4A depicts a graph of pulse sound amplitudes plotted versus cuff pressures when utilizing the novel blood pressure monitoring system of the present invention.

With reference now to FIG. 4A there is depicted a graph of pulse sound amplitudes plotted versus cuff pressures. As can be seen, the amplitude of pulse sounds detected at distal audio transducer 38 will increase as the pressure within inflatable cuff 22 bleeds off. The point where the pulse sounds detected at distal audio transducer 38 become audible is generally referred to as the systolic blood pressure. It should be noted that as cuff pressure diminishes further from right to left in the graphs of FIG. 4A, that the distal pulse sound amplitudes drop off rapidly at a point which is acknowledged to be the diastolic blood pressure. Many blood pressure monitoring systems utilize distal pulse sound amplitudes to detect both systolic and diastolic blood pressures by determining the point at which the distal pulse sound amplitudes first exceed a given reference value and the point thereafter at which the distal pulse sound amplitudes fall below a given reference value. It should be noted that the values depicted in FIG. 4a are ideal in nature and that in actual practice artifact noises make these two points substantially more difficult to locate.

Figure 4B:
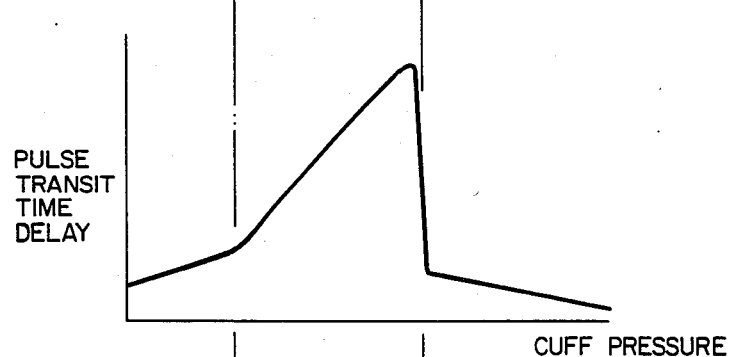
FIG. 4B depicts a graph of the time delay between pulse sound detected proximal to the blood pressure cuff and the pulse sound detected distal to the blood pressure cuff versus cuff pressure when utilizing the novel blood pressure monitoring system of the present invention.

Referring not to FIG. 4B, there is depicted a graph of the time delay between a pulse sound detected at the proximal audio transducer and the sound generated by the same pulse when it reaches the distal audio tranducer. As can be seen, at high cuff pressures a small amplitude distal pulse sound is present which occurs at practically the same time as the pulse sound detected by the proximal audio transducer. At a point generally determined to be the systolic blood pressure the transit time or delay between a pulse detected at the proximal audio transducer and the same sound detected at the distal audio transducer becomes quite high. Thereafter, as cuff pressure continues to diminish the time delay between the moment a pulse is detected at the proximal audio transducer and the moment that pulse is detected at the distal audio transducer decreases generally linearly to a point where the decrease shifts slightly. That point is generally referred to as the diastolic blood pressure. Again, the graph depicted in FIG. 4B is ideal in nature and the presence of artifact noise makes this method highly difficult to utilize to accurately determine systolic and diastolic blood pressure.

Figure 4C:
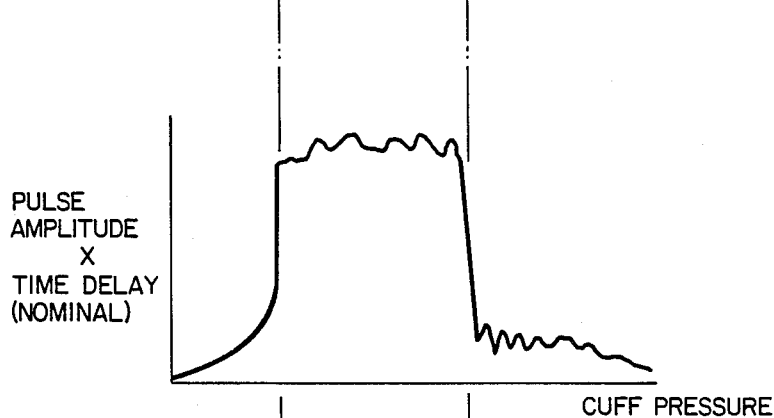
FIG. 4C depicts a graph of a blood pressure evaluation curve which is obtained by determining the product of the pulse amplitudes depicted in FIG. 4A and the time delays depicted in FIG. 4B versus cuff pressure with the novel blood pressure monitoring system of the present invention.

With reference now to FIG. 4C, there is depicted a graph of a novel blood pressure evaluation curve which is utilized by blood pressure monitoring system 10 of the present invention. The graph in FIG. 4C is obtained by multiplying the pulse amplitudes present in FIG. 4A by the pulse transit time delay values depicted in graph 4B. As may be seen, the combination of these two measurements results in an evaluation curve which includes highly distinguishable transitions at the systolic and diastolic pressure points. The utilization of this evaluation curve greatly enhances the accuracy of blood pressure monitoring system 10 and permits systolic and diastolic pressure to be accurately determined by an evaluation of the curve.

Figure 4D:
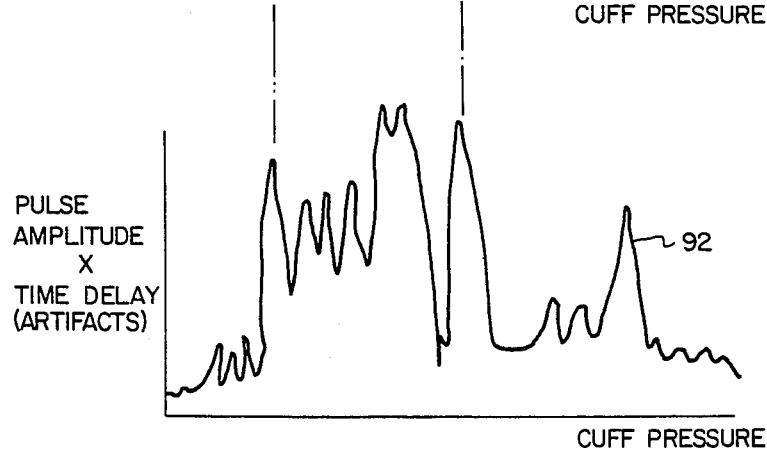
FIG. 4D depicts a graph of a blood pressure evaluation curve similar to FIG. 4C wherein large artifact errors are present.

Finally, FIG. 4D depicts a graph of a blood pressure evaluation curve similar to that depicted in 4C wherein large artifact errors are present. As may be seen, the graph depicted in FIG. 4D would make evaluation of systolic and diastolic transition points rather difficult. In order to successfully determine systolic and diastolic pressure points when utilizing a curve similar to that depicted in 4D, an additional filter and analysis step is required to eliminate errors which may be caused by artifact noise.

The analysis of the graph depicted in FIG. 4D is accomplished by digital operation on the values depicted therein by means of microprocessor 44 (see FIG. 3). In a preferred embodiment of the present invention each cuff pressure point on graph 4D is analyzed utilizing a so-called "median" filter. A median filter analyzes several successive points and substitutes the median value point for the middle point of the analyzed points. Five data points are used in this embodiment. In this manner, large transitions followed by a recession to nominal values will be eliminated. Next, a weighted average filter may then be applied to achieve further smoothing of the curve which results from the utilization of the median filter. Those ordinarily skilled in the art will appreciate that while these two well known filtering techniques are utilized in the depicted embodiment of the present invention that other statistical smoothing techniques may be equally advantageous and may also be utilized.

Finally, a statistical analysis approach is utilized to analyze the resultant curve to determine the transitions points which represent systolic and diastolic pressure. Most known blood pressure monitoring systems utilize an absolute level which is predetermined and report systolic pressure at the first point which occurs above this nominal level and diastolic pressure at the first point thereafter which occurs below the predetermined level. In contrast, blood pressure monitoring system 10 of the present invention utilizes a statistical analysis to determine whether or not a particular rise in the curve represents the systolic pressure. For example, points along the curve are tested until such time as three successive points exceed the standard deviation from the curve at that point. Thereafter, microprocessor 44 selects the second point which exceeded the standard deviation and designates that point as the systolic pressure.

Additionally, a second processing technique is utilized to ensure that the statistical analysis previously described does not result in an erroneous reading due to a large artifact such as the artifact present at point 92 of FIG. 4D. This system sets up estimated systolic and diastolic pressures by analyzing the smooth curves of the amplitude data and amplitude-delay time product data. The maximum points along the curves are found and then the data point previous to the first three consecutive points that are less than some percentage of that maximum point becomes the estimated systolic pressure. A percentage of fifty percent for amplitude data and a percentage of forty percent for product data are used. These become the estimated systolic and diastolic pressures and the determined systolic and diastolic pressure must be within a selected range of the estimated systolic and diastolic pressures to permit blood pressure monitoring system 10 to accept the determination.

Figure 5A:
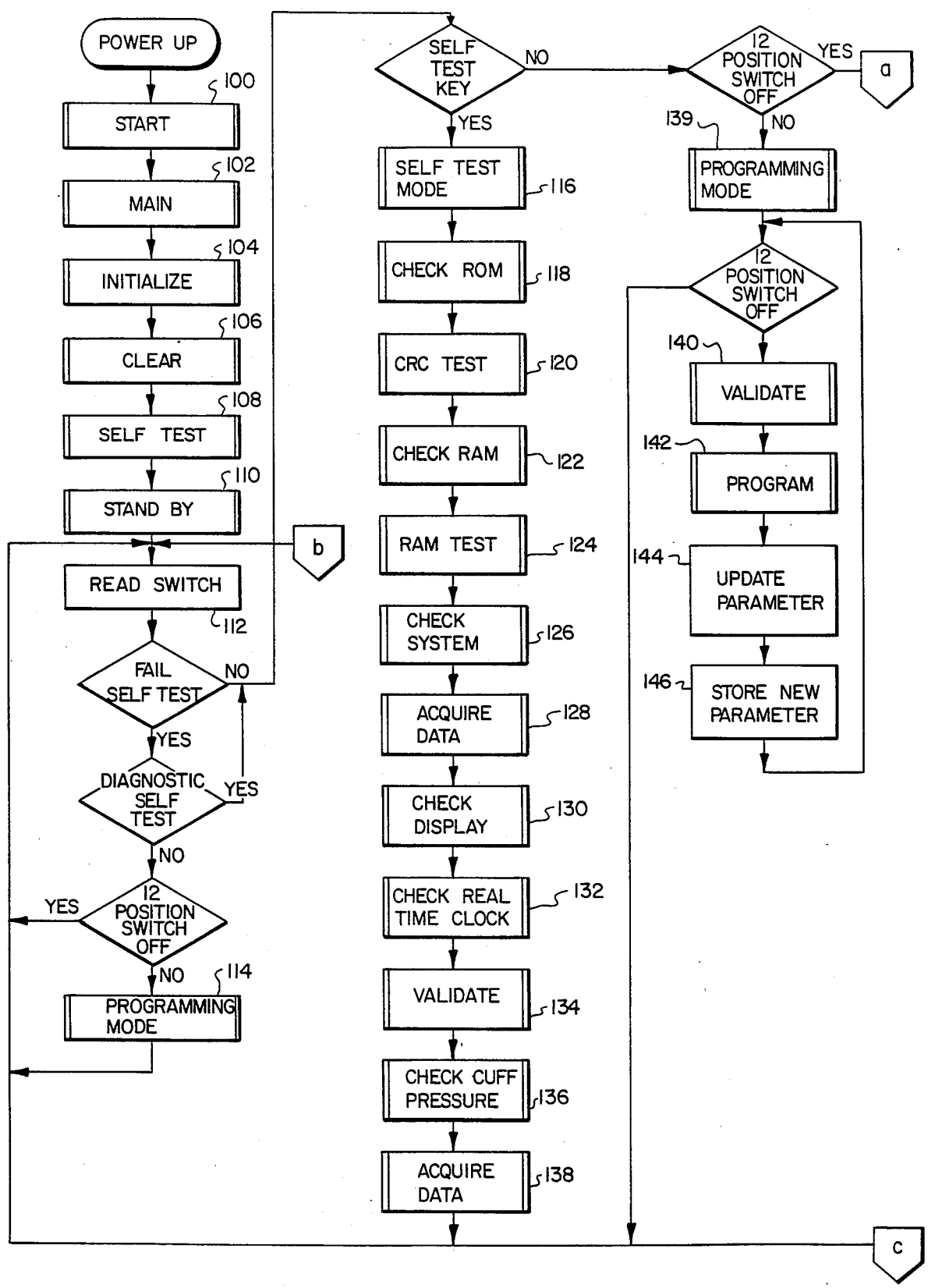
FIGS. 5A, 5B and 5C depict a logic flow diagram for the operation of the novel blood pressure monitor system of the present invention.
Figure 5B:
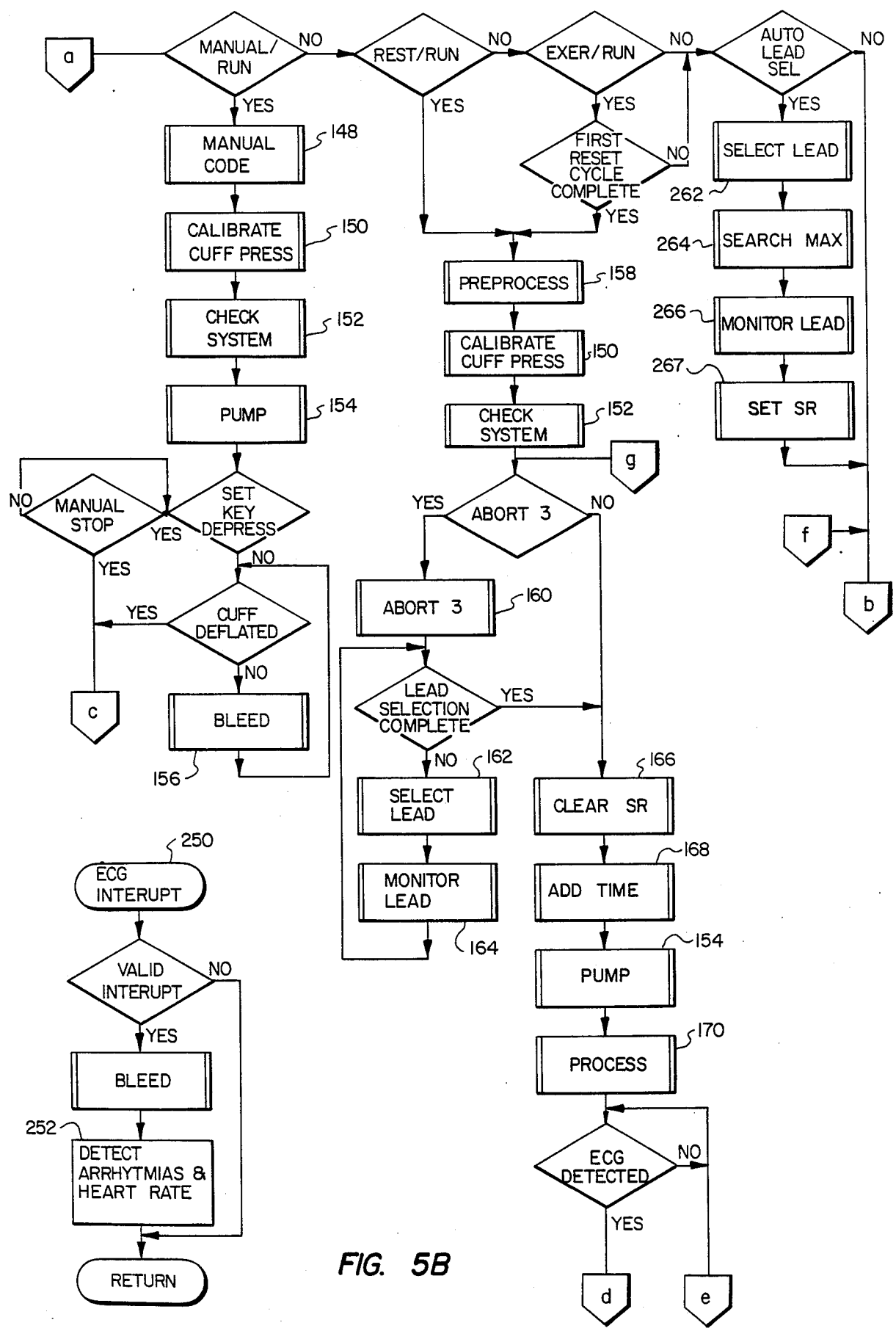
Figure 5C:
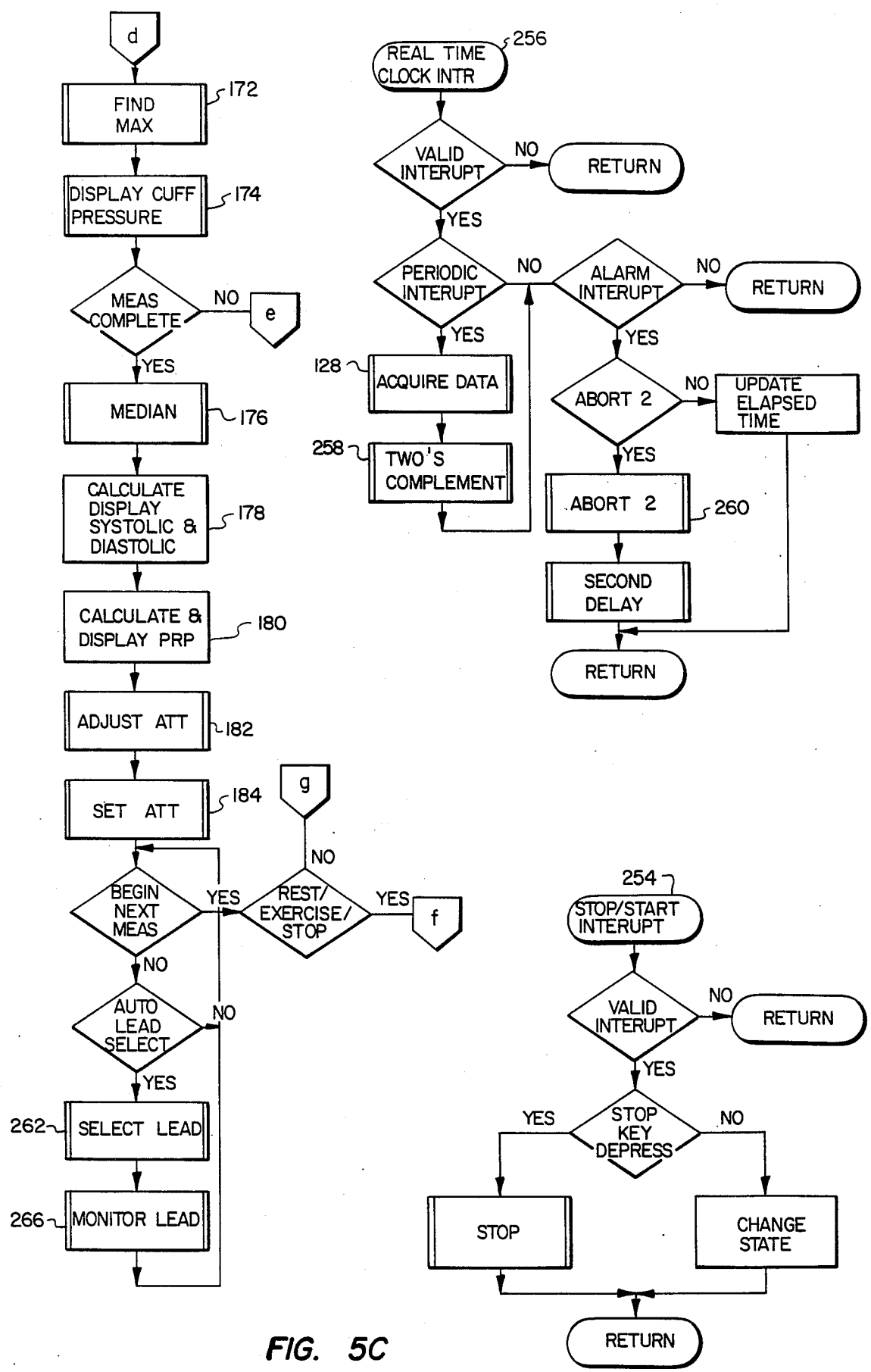

Finally now referring to FIGS. 5A, 5B, and 5C, there is depicted a logic flow diagram for the operation of blood pressure monitoring system 10 of the present invention.

Processing of blood pressure information is accomplished by blood pressure monitoring system 10 and initiated by the application of power to electronics unit 20 of blood pressure monitoring system 10. After power has been applied to blood pressure monitoring system 10 a start routine illustrated in block 100 begins instruction execution. The address for this routine is fetched by microprocessor 44 at the reset exception vector and is stored as the initial program counter. The start routine the initializes the address registers and reverts program execution to the main portion of the program indicated in block 102. This portion of the program permits all hardware devices to be initialized as indicated in block 104 and the status register is cleared as indicated in block 106. Thereafter, a self test sequence is performed as indicated in block 108. In the event the blood pressure monitoring system has failed a self test an error message is displayed.

The self test sequence takes approximately ten seconds to complete and results in a diagnostic message when an error occurs during the self test. Additionally, a tone alarm will sound for one second to indicate that an error in the diagnostic mode has been indicated.

Among the tests indicated in the diagnostic mode of self test are the check ROM test indicated at block 118. The check ROM test is a cyclic redundancy check (CRC) as indicated in block 120 which is performed on the program ROM located at selected byte addresses within ROM 52. Additionally, a check RAM routine indicated by block 122 is performed and various RAM tests indicated by block 124 are performed on specific byte addresses within random access memory 54.

The diagnostic mode then tests the power supplies present within blood pressure monitoring system 10 and individual channels of multiplexer 78 are selected and verified for a specified range as indicated in block 126.

Data within individual channels of multiplexer 78 are then acquired as indicated in block 128 by selecting the desired analog signal and converting from analog to digital state.

Blood pressure monitoring system 10 next allows the operator to check the displays, alarm LEDS, switch LEDS and tone alarm for functionality during the check indicated in block 130. Validation of the real time clock's programmable parameters is performed as indicated in block 132 and block 134 and the cuff pressure transducer circuitry is tested as indicated in block 136. Dump valve 74 and bleed valve 72 are opened at the start of this self test in order for the transducer to stabilize prior to the test occurring. The cuff pressure channel on multiplexer 78 is selected and the output from the analog to digital converter 80 is read. This reading corresponds to a cuff pressure relatively close to zero. Finally, after the cuff pressure has been completely bled off, data within the appropriate channel of multiplexer 78 is acquired for a self test.

After the self test is complete, the blood pressure monitoring system 10 is placed into the standby mode as indicated in block 110.

Operation of blood pressure monitoring system 10 is then begun as indicated in block 112 by a routine which monitors the user's selection of front panel control keys and switches. A preliminary record of the switch buffers is stored each time the routine is called and the switch buffer contents are compared to preliminary switch buffer contents to detect the user's inputs.

Referring now to FIG. 5B as well as FIG. 5A, additional logic flow chart diagrams are depicted which demonstrate the various operational modes of blood pressure monitoring system 10. First, the self test may be performed again by pressing the self test key as indicated in block 116. Second, the twelve position parameters may be programmed by the programming routine as indicated in block 139. Third, the manual mode routine indicated at block 148 provides for manual operation of blood pressure monitoring system 10. The manual mode of operation is entered by pressing the manual key and then pressing the run key on electronics unit 20. After calibrating the cuff pressure as indicated at block 150 and checking the system as indicated in block 152, blood pressure monitoring system 10 will pump inflatable cuff 22 up to the operator selected pressure as indicated in block 154 and then begin bleeding inflatable cuff 22 at a rate of 3 mmHg per second as indicated in block 156. This method will terminate when inflatable cuff 22 has been deflated to a pressure below 40 mmHg or until the manual stop key has been depressed. Any changes in the switch position cause the validate and program stops 140 and 142 to be enacted and the switch parameter to be updated as indicated in block 144 and the new switch parameter thereafter stored per block 146.

Next, the rest mode may be utilized to obtain base line blood pressure measurements while patient 12 is at rest. Base line information from the rest mode is required prior to activating the exercise mode. To begin operation in the rest mode, the operator presses a stop/run push button to select the run state which is indicated by the lighting of an LED. The preprocess function indicated at block 158 then occurs and a complex sequence of events takes place. The pressure transducer 76 is calibrated, as indicated in block 150, blood pressure monitor system 10's power supplies are tested as indicated in block 152 and all displays are reset to zero. The Abort "3" procedure is then utilized to determine whether or not an electrocardiographic Lead signal is present. If the Abort "3" flag indicates a loss of electrocardiographic signal, the Abort "3" routine, as indicated in block 160, is activated and an alternate electrocardiographic Lead is selected as indicated in block 162. The selected Lead is monitored as indicated in block 164 and if Lead selection has been completed microprocessor 44 will then clear the status register as indicated in block 166 to begin operation.

Block 168 is then utilized to calculate the interval in time of a measurement cycle by adding the current time and the interval time setting as established by the operator. As above, inflatable cuff 22 is then pumped up as indicated in block 154 until the pressure within inflatable cuff 22 reaches the desired cuff pressure.

The data acquisition mode of blood pressure monitoring system 10 indicated by block 170 labeled "Process" has several steps in a loop that are performed while the cuff is depressurizing. These steps include: (1) waiting for an electrocardiographic trigger to occur; (2) finding a pulse indicated by the proximal audio transducer output signal; (3) finding a pulse indicted by the distal audio transducer data; (4) finding the average cuff pressure for that pulse; (5) checking for an arrhythmia or false trigger condition; (6) performing a real time sort by cuff pressure of the data; (7) checking the cuff pressure against the value needed to open the dump valve and exit from data acquisition loop; (8) recovering from temporary loss of an electrocardiographic signal interrupt if necessary; (9) checking the amplitude of the distal pulses and reinflating the cuff if a large amplitude occurs near the beginning of the measurement; and (10) checking the amplitude of the proximal pulses and aborting the measurement if the amplitude is too low.

The processing procedure utilized by blood pressure monitoring system 10 utilizes a concept of "windowing" in the description of the proximal and distal audio transducer data acquisition process. "Windowing" is the process utilized to reduce the amount of data that is examined for each pulse. The size of the window is determined by previous data and its location is determined by a trigger from another event.

A pulse detected by the proximal audio transducer is searched for in a window of the raw proximal audio transducer data. The window begins 25 milliseconds after the occurrence of an electrocardiographic pulse and continues for 250 milliseconds during the first measurement. Thereafter, the duration is adjusted as discussed below. A subroutine is utilized to find the location and peak-to-peak amplitude of the proximal pulse. When the proximal pulse has been located and its amplitude stored in memory, the delay time from electrocardiographic trigger to proximal pulse is calculated by subtracting the location in time of the electrocardiographic trigger from the location in time of the proximal pulse in memory and then saving that data.

The distal pulse is searched for in a window of the raw distal audio transducer data. This window begins 50 milliseconds before the location of the proximal pulse that was just found. The distal window is open for 225 milliseconds. The same subroutine is then utilized to find the location and peak-to-peak amplitude of the distal pulse. The proximal pulse to distal pulse delay time is calculated by subtracting the location in time of the proximal pulse from the location in time of the distal pulse in memory. The delay time between these two pulses and pulse amplitude are then saved.

It is well known in the art that the proximal pulse diminishes toward the end of a measurement cycle. Since the search for the distal pulse is based upon the location of the proximal pulse, the loss of the proximal pulse must be compensated for. This is accomplished by first calculating an average of the first five electrocardiographic trigger to proximal pulse delay times after the fifth pulse has occurred. Beginning with the sixth pulse, this average is utilized as the position, relative to the electrocardiographic trigger signal, from which to search for the distal pulse.

The next step in the processing loop is to find the cuff pressure for a given pulse. An average of the fifty cuff pressure points corresponding to the distal pulse window is calculated and saved. The calculated avarage cuff pressure is then displayed if it is less than the cuff pressure of the previous pulse. This check is made to prevent the display of temporary changes in cuff pressure. This condition is common during exercise measurements because arm movement can cause large temporary fluctuations in cuff pressure.

The process program next checks for an arrhythmia condition by examining a flag set by the electorcardiographic interrupt handler. This flag is set if the time between the last electrocardiographic trigger signal and the current electrocardiographic trigger signal is more then twenty-five percent different than the average. This may signal a true arrhythmia or a false trigger. If the arrhythmia flag is set and the pulse amplitude is near the noise level and the cuff pressure is within the previous systolic to diastolic envelope, that pulse is rejected as a probable false trigger pulse.

The next step in the data acquisition loop is the real-time ordering of cuff pressure values. This technique is employed because of the possibility of a temporary cuff pressure increase due to arm movement. Ordering the cuff pressures allows for the maximum amount of data to be available for blood pressure detection. The real-time ordering process is best described as a single pass of a bubble sort. The technique begins by comparing the cuff pressure of the present pulse with the immediately preceding average cuff pressure array value. If the present cuff pressure is less, no action is needed; if the present cuff pressure is equal to the previous value, the present value is ignored. If the present value is greater than the previous value, the two cuff pressures swap positions in the array along with the corresponding pulse and delay data. The present value, in its new position, is then compared with its new, immediately preceding value and swapped if necessary.

Next, the present cuff pressure is compared with the predetermined value necessary to open dump valve 74. If dump valve 74's opening value has been reached, an external flag is set. An internal flag is also set that allows the data acquisition loop to terminate.

The next section of the data acquisition processing loop attempts to recover from a temporary loss of the electrocardiographic signal. If a difference of more than 20 mmHg exists between the cuff pressure of the present and previous pulses, then the cuff is reinflated to a pressure 10 mmHg greater than the previous cuff pressure value. In this way, pulse data that should have been acquired during the 20 mmHg gap can be acquired.

Next, the amplitude of the output of the distal audio transducer is then compared with the nominal distal pulse threshold for the first five pulses of the measurement. If the distal pulse amplitude is above this threshold, cuff pressure is probably insufficient to obtain distal data above the systolic level. If two consecutive distal pulses are above the threshold, the cuff is reinflated to a point 30 mmHg above the initial inflation value. This reinflation may occur twice. If a third reinflation is necessary, the dump value is opened and a message is displayed to the operator. The machine then waits ten seconds and re-initiates the measurement procedure.

The amplitude of the proximal pulse is also compared with a noise threshold for the first eight pulses of the measurement. The amplitude of the proximal pulses should be significant near the beginning of the measurement. A low proximal amplitude could signal a faulty audio transducer or poor positioning of the cuff. If three consecutive pulses are less than the threshold value, the measurement is aborted, and a message is displayed to the operator.

After the pulse data has been collected, the further processing of the data consists of several steps in addition to the actual calculation of blood pressure. Included among these steps are: (1) adjustment of the length of the proximal pulse window for the next cycle; (2) multiplying the proximal pulse to distal pulse delay time and the corresponding distal pulse amplitude to obtain the product data set; (3) median filtering the distal amplitude data set and the product data set; (4) weighted average filtering the distal amplitude data set and the product data set; (5) determine blood pressure from both data sets and display the best results; (6) setting the cuff pump up value and the dump valve opening value for the next cycle; (7) calculation and display of the average heart rate; (8) calculation and display of the pulse rate product (PRP); (9) setting of maximum systolic and diastolic alarms if necessary; and (10) adjustment of the programmable attenuators for the next cycle.

The proximal window length is readjusted during processing for the next cycle. This is advantageous because the time between the electrocardiographic trigger signal and the proximal pulse can vary widely from one cycle to the next. The dynamic quality of the proximal window length allows the minimum amount of raw data processing without sacrificing flexibility. The adjusted proximal window length is calculated by finding an average of the first ten electrocardiographic trigger signals to proximal pulse delay times and then adding 100 milliseconds to that average.

Next, the product data set is generated to determine the blood pressure evaluation curve. The product utilized is, as explained above, that of the distal amplitude and the proximal pulse to distal pulse delay time for the pulse. The proximal to distal delay time is derived by subtracting the average electrocardiographic trigger signal to proximal pulse delay time from the electrocardiographic trigger signal to distal pulse delay time. The delay time is calculated in this way because the proximal pulse diminishes before the distal pulse which means that the actual delay time is not reliable. This data set is generated for the purpose of finding the systolic pressure. It is well known in the art that the proximal pulse to distal pulse delay time is greatest at the systolic pressure point. This characteristic adds definition to the systolic pressure point and therefore increases the reliability of the systolic pressure calculation.

The median filter and weighted average filter are then applied to both the amplitude data set and the product data set as indicated in block 176. The primary function of the median filter is to remove single or double point artifacts from the data set. The median filter does this very well but it can also cause consecutive data points to be equal. This can cause the data set to have a stairstep appearance. The weighted average filter removes these stairsteps and further smooths the data. This filter produces a new output data point by adding a value to the previous input data point. This value is one-half the difference between the current and previous input data points.

Another important feature of blood pressure monitoring system 10 of the present invention is that the cuff inflation value and dump valve opening value may be changed from one cycle to the next due to the fact that blood pressure may change greatly during a stress test. This is accomplished by adding a value to the systolic pressure to obtain the cuff inflation value for the next cycle and by subtracting a value from the diastolic pressure to obtain the dump valve opening value for the next cycle. An error resulting in a low systolic reading can cause successive measurements to be in error due to insufficient inflation of inflatable cuff 22. Blood pressure monitoring system 10 attempts to avoid this problem by comparing the present systolic pressure to the systolic pressure from the previous measurements. The over pump value is then added to the greater of the two pressures. This has the effect of now allowing a single poor measurement to affect the inflation value for the next measurement. If blood pressure monitoring system 10 is in the rest mode a value of 30 mmHg is added to the systolic pressure and a value of 20 mmHg is subtracted from the diastolic pressure. If blood pressure monitoring system 10 is in the exercise mode, a value of 50 mmHg is added to the systolic pressure and a value of 30 mmHg is subtracted from the diastolic pressure.

In keeping with the dynamic nature of blood pressure monitoring system 10, both proximal and distal audio transducers are equipped with software programmable attenuators. This is necessary because the amplitude of the pressure pulse signals increase as heart rate and systolic pressure increase and the amplitude decreases as the patient returns to normal after exercising. The maximum amplitude of the signal detected by the audio transducers are utilized to adjust the attenuator setting at the end of cycle as indicated in blocks 182 and 184.

The process of determining the systolic and diastolic pressures from each of the two mentioned data sets utilized by blood pressure monitoring system 10 begins with finding the value and position of the largest distal pulse in the data set as indicated in block 172. In the product data set, the estimated systolic pressure is generated by searching the distal pulse data beginning with the position of the largest distal pulse and searching toward the data with the highest cuff pressure. When three consecutive distal data values are found to be less than forty percent of the maximum distal pulse value, the cuff pressure of that data point immediately preceding the first point below forty percent of the largest distal pulse becomes the estimated systolic pressure. The estimated diastolic pressure is then found in a similar manner by examining the distal pulse data beginning with the position of the largest distal pulse and searching toward the lowest cuff pressure. Again, individual points are examined until such time as three consecutive points are found which are below forty percent of the largest distal pulse amplitude. The same method is used to find the estimated systolic and diastolic pressures in the amplitude data set except that the threshold test uses a value of fifty percent.

Once the estimated systolic and diastolic pressures have been determined, an iterative technique is utilized to generate a set of provisional systolic pressures as indicated in block 178. To generate the set of provisional systolic pressures, the iterative technique is applied to the distal pulse data and the analogous cuff pressure data beginning with the highest cuff pressure and proceeding toward the estimated systolic pressure. The provisional diastolic pressures are generated by utilizing the iterative technique beginning with the lowest cuff pressure and proceeding toward the estimated diastolic pressure. The iterative technique uses statistical methods to generate the set of provisional pressures. Since the methods used are mathematical in nature, it is easier to represent the necessary values in terms of "X" and "Y". In the following discussion, a reference to "X" indicates a cuff pressure value and a reference to "Y" indicates the analogous distal pulse amplitude. The slope and Y intercept calculations are utilized to represent a "best fit" line through the data in an X-Y coordinate system. The standard deviation about the slope line is used to represent the variation of the data from the slope line. An expected value of Y calculation is used to make inferences about an actual value of Y. A prediction interval based upon the values of statistical distribution are utilized to find the departure from normal of the distal pulse amplitudes. The statistical method is begun by initializing several sums with the X and Y data of the first three data points. The sums needed for the statistical calculation consist of the sum of the X values, the sum of the Y values, the sum of the squares of the X values, the sum of the squares of the Y values and the sum of the products of the X and Y values. Next, the slope and Y intercept of the regression line and standard deviation are calculated. Beginning with the next pair of X and Y values, an expected value of Y for the actual value of X is calculated. Next, a prediction interval is calculated and added to the expected value of Y. This sum is the prediction range. It is compared to the actual value of Y to determine the disposition of the associated X value.

If the actual value of Y is less than or equal to the prediction range, the current X and Y values are added to the sums and new slope, Y intercept, and standard deviation values are calculated. Then new expected value, prediction interval, and prediction range values are calculated utilizing the next pair of X and Y values.

If the actual value of Y is greater than, or deviates from, the prediction range, the current X and Y values are not added to the sums. Instead, only new expected value, prediction interval, and prediction range values are calculated utilizing the next pair of X and Y values.

The prediction range is then compared to the acutal value of Y and, as a result, the actions described in one of the above two paragraphs are taken. This sequence continues until three consecutive actual Y values are greater than the prediction range. When three consecutive deviations occur, the provisional value for this iteration of the loop is the X value associated with the second of the three Y values to deviate.

Another iteration is then begun by adding to the sums the X and Y values of the first of the three points to deviate, the calculating new slope, Y intercept, standard deviation, expected value, and prediction range values. The next Y value, the second point to deviate from the previous iteration, is then compared to the prediction range and one of the paths described above is taken. The second iteration continues until another provisional pressure is found and added to the set. The iterations continue until the provisional pressure just found is within 5 mmHg of the estimated systolic or diastolic pressure.

Once the set of provisional values is complete, an attempt is made to choose the most accurate value as the final pressure. As the iterative technique approaches the estimated pressure, the provisional values found tend to be contiguous data points. This is because the distal pulse amplitude increases quickly as the blood pressure envelope is approached. The selection of the final pressure is begun by testing the provisional pressures beginning with the value closest to the estimated pressure and testing in reverse order of acquisition. The provisional value is rejected if the next provisional value is also the next data value in the X data set. The rejection process is continued until the next provisional value is not the next X value, or until only one provisional value is left. The final pressure is the provisional value being tested when the rejection process is stopped.

The iteration technique and provisional value rejection process described above are utilized for finding the systolic pressure and the diastolic pressure. As mentioned earlier, the systolic pressure is found by processing the data set from the highest cuff pressure toward the estimated systolic pressure, or from the beginning of the data set toward the middle. The diastolic pressure is found by processing the data from the end of the data set toward the middle. Although the process is the same in both cases, separate program codes are utilized in the preferred embodiment of the present invention because the polarity of the comparisons utilized is reversed.

Various interrupt signals within blood pressure monitoring system 10 may be utilized to interrupt the process just described. The first such interrupt, depicted as part of FIG. 5B, is the electrocardiographic interrupt indicated at block 250 of FIG. 5B. This interrupt routine services the electrocardiographic Leads and is active only during the rest or exercise mode of blood pressure monitoring system 10's operation. A valid electrocardiographic interrupt check is made each time the routine is called. Processing is immediately transferred back to the point at which the interrput occurred when an invalid interrupt has been detected. The electrocardiographic interrupt is used to keep a running time count of the last six electrocardiographic pulses to determine the intermediate heart rate. This running time count includes arrhythmias and is updated every time after the first electrocardiographic trigger. The intermediate heart rate value is visible on front panel 42 of electronic unit 20 and is updated every two seconds. Arrhythmia detection is done after the first three electrocardiographic trigger signals. Thereafter, a running three pulse time count is kept and compared to the previous running three pulse time count. An arrhythmia has occurred when the current pulse time deviates from the last pulse time by twenty-five percent. This process is indicated by block 252.

A stop/start interrupt as indicated at block 254 of FIG. 5C is utilized to change mode operation from stop to start or from start to stop each time the user depresses and releases the stop/start key. The start mode initiates the rest, exercise and manual modes of operation. The stop mode halts the activity of the current operation except for the self test and programming modes.

Finally, the real-time clock interrupt signal indicated at block 256 of FIG. 5C services two of three possible sources of real-time clock interrupts to microprocessor 44, the alarm interrupt and the periodic interrupt. Alarm interrupts are initiated by the preprocess routine which activates a one second interrupt to update the elapsed time at the elapsed time display. The elapsed time display is disabled and an error message is displayed when an error condition is detected. The elapsed time continues to update, but the display retains a user message indicating that the operator should check the system until the error condition is corrected. If an electrocardiographic trigger Lead is detected as being detached, then the "Abort 2" subroutine indicated at block 260 is utilized to delay operation so that a proper electrocardiographic Lead may be selected.

Periodic interrupts are uniquely initiated from various routines. A test is made for the routine currently activating the interrupt in a top down fashion. After a periodic interrupt, data which has been acquired as indicated in block 128 is put into two's complement form by the routine indicated at block 258.

Finally, referring again to FIG. 5B, the process by which blood pressure monitoring system 10 selects the optimum electrocardiographic Lead configuration is illustrated. The select lead routine indicated by block 262 is utilized to determine which of the three electrocardiographic Leads is utilized as a trigger lead. Each of the electrocardiographic Leads is analyzed as indicated in block 264 to determine which Lead has the largest signal to noise ratio. After a particular Lead has been detected as having the largest signal to noise ratio, that Lead is monitored as indicated in block 266 and utilized to generate the electrocardiographic trigger signal. The status register is set at block 26%.

While the logic flow diagrams illustrated in FIGS. 5A, 5B and 5C are meant to illustrate the operation of blood pressure monitoring system 10, those ordinarily skilled in the art will appreciate that alternate algorithms may be utilized which will not depart substantially from the spirit and scope of this invention. A copy of the source code utilized to operate blood pressure monitoring system 10 is attached hereto as Appendix A; however, variations in that program may be suggested to those ordinarily skilled in the art upon reference to this specification and it is comtemplated that the appended claims will cover these and other modifications or embodiments that fall within the true scope of this invention.

```
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern unsigned long CURRENT_INT_TIME, PREVIOUS_INT_TIME;

extern int IO_CONTROL,io_control,ALARM_LED,alarm_led,TRIGGER_LEAD,
           SECOND_BEST,DIA_DISPLAY,PRP_DISPLAY,SYS_DISPLAY,REG_B;

extern short bleed_valve,STATUS_OF_LEAD_SELECTION_PROCESSING,
             CLOCK_RUNNING,ERROR_CONDITION,ALARM_ON,ABORT2,
             NO_ECG_FOUND,
             MODE_IS_STOP,MODE_IS_START,ecg_control;

extern unsigned short BLEED_VALVE,ECG_CONTROL;

/*********************/
/****************************         ABORT2          ****************************/
                           /*********************/

/*
   Routine Name         : abort2
   Parameters Passed    : --
   Parameters Returned  : --
   Calling Routines     : real_time_clock_interrupt
   Routines Called      : second_delay, display, clear_sr, stop
   Local Variables      : i -- loop control
*/ abort2()
{short i;

/*
   Disable elapsed time update, data acquisition, pump, ECG's, and open
   dump and bleed valves.
*/
```

```
REG_B &= (DISABLE_AIE & DISABLE_PIE);
CLOCK_RUNNING = NO;
IO_CONTROL = io_control &= DUMP_VALVE_OPEN;
IO_CONTROL = io_control |= PUMP_OFF;
BLEED_VALVE = bleed_valve |= BLEED_VALVE_OPEN;
ECG_CONTROL = ecg_control &= DISABLE_ECG_INT;
NO_ECG_FOUND = NO;
CURRENT_INT_TIME = PREVIOUS_INT_TIME = 0;

/*
Indicate error condition to user.  The DIASTOLIC display will show the
previous trigger lead which is no longer satisfactory.
*/

ALARM_LED = alarm_led |= (TONE_ALARM_ON | ECG_LED_ON);
ALARM_ON = ERROR_CONDITION = YES;
display(&SYS_DISPLAY,"  0   0   0ECG CHECK",17,-1,0);
switch (TRIGGER_LEAD){ case ECG_LEAD1 : display(&DIA_DISPLAY," L1",2,-1,0);
                    break;
   case ECG_LEAD2 : display(&DIA_DISPLAY," L2",2,-1,0);
                    break;
   case ECG_LEAD3 : display(&DIA_DISPLAY," L3",2,-1,0);
                    break;
} clear_sr(LEVEL0_INTERRUPT);

/*
Sound tone alarm for 1 second.
*/ second_delay(1);
ALARM_ON = NO;
ALARM_LED = alarm_led &= TONE_ALARM_OFF;

/*
Delay for a total of 10 seconds before allowing the use of the second
best lead configuration.  This allows the ECG circuitry to stabilize
after a lead has come loose.
*/ for (i = 0; i < 9 && MODE_IS_START; i++)
   second_delay(1);

/*
Reenable periodic interrupts.
*/

REG_B |= ENABLE_PIE;

/*
Select the second best lead choice if the user has not stopped the
current measurement cycle.  Do not change leads if the user has
manually selected the lead.
*/ if (MODE_IS_START){
   if (STATUS_OF_LEAD_SELECTION_PROCESSING == YES){
      TRIGGER_LEAD = SECOND_BEST;
      ECG_CONTROL = ecg_control &= CLEAR_LEAD_SELECTION;
      ECG_CONTROL = ecg_control |= TRIGGER_LEAD;
      ECG_CONTROL = ecg_control &= FLOAT_RESET_LOW;
      ECG_CONTROL = ecg_control |= FLOAT_RESET_HIGH;
   }
```

```
    }
    else{
      stop();
      return;
    }

/*
  Reset variables once the 10 second delay is up. Set flag to 'process'
  routine to signal recovery has occurred. Reenable the elapsed time
  update. Remove previous error messages from the displays and continue
  with the measurement.
*/

ERROR_CONDITION = NO;
    ABORT2 = CLOCK_RUNNING = YES;
    REG_B |= ENABLE_AIE;
    display(&PRP_DISPLAY," 0.0      ",8,-1,0);
    return;

"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern unsigned int bleed_valve;
extern int TRIGGER_LEAD,DIA_DISPLAY,PRP_DISPLAY,REG_B,IO_CONTROL,
           SYS_DISPLAY,io_control,ALARM_LED,alarm_led;
extern short PROCESSING_LEAD_SELECTION,LEAD_MONITORING,LEADS_PROCESSED,
             LEAD_PROGRESS,LEAD_STATUS,LEAD1[],LEAD2[],LEAD3[],BAD[],
             LEAD_SELECTION_COMPLETE,MODE_IS_START,ALARM_ON,
             CLOCK_RUNNING,ERROR_CONDITION;
extern unsigned short BLEED_VALVE;

/********************/
/*************************    ABORT3    *******************************/
                          /********************/

/*
  Routine Name          : abort3
  Parameters Passed     : --
  Parameters Returned   : YES -- signals calling routine that abort
                                 procedure was successful
                          NO  -- signals calling routine that abort
                                 procedure failed
  Calling Routines      : preprocess
  Routines Called       : select_lead, display
  Local Variables       : i -- loop control
*/ abort3()
{short i;

/*
  Disable pump and open dump and bleed valves.
*/

IO_CONTROL = io_control &= DUMP_VALVE_OPEN;
    IO_CONTROL = io_control |= PUMP_OFF;
    BLEED_VALVE = bleed_valve |= BLEED_VALVE_OPEN;
```

```c
/*
 Sound tone alarm for 1 second and turn on ECG LED alarm.
*/

ALARM_LED = alarm_led |= (TONE_ALARM_ON | ECG_LED_ON);
  ALARM_ON = YES;

/*
 The DIASTOLIC display will tell the operator which trigger lead
 was last functioning properly.
*/ display(&SYS_DISPLAY,"  0   0   0",8,-1,0);
  switch (TRIGGER_LEAD){ case ECG_LEAD1 : display(&DIA_DISPLAY," L1",2,-1,0);
                     break;
    case ECG_LEAD2 : display(&DIA_DISPLAY," L2",2,-1,0);
                     break;
    case ECG_LEAD3 : display(&DIA_DISPLAY," L3",2,-1,0);
                     break;
  }

/*
 Activate lead selection and reset flags.
*/

PROCESSING_LEAD_SELECTION = YES;
  LEAD_MONITORING = 1;
  LEAD_SELECTION_COMPLETE = NO;
  LEADS_PROCESSED = LEAD_PROGRESS = LEAD_STATUS = 0;
  for (i = 0; i < 3; i++)
    LEAD1[i] = LEAD2[i] = LEAD3[i] = BAD[i] = 0;

/*
 Do lead selection until a new lead has been selected or the
 measurement is stopped.
*/ while (MODE_IS_START && !LEAD_SELECTION_COMPLETE)
    select_lead(&LEAD_PROGRESS,&LEAD_MONITORING,&LEAD_STATUS);

/*
 Remove error message from the display and reactivate the elapsed
 time if a new trigger lead was successfully selected and the user
 has not depressed the STOP key.  Continue with the measurement.
*/ if (MODE_IS_START){
    display(&PRP_DISPLAY," 0.0     ",8,-1,0);
    REG_B |= ENABLE_AIE;
    CLOCK_RUNNING = YES;
    ERROR_CONDITION = NO;
    return(YES);
  }

/*
 Either user was no longer in the RUN state of operation or
 a good trigger lead could not be selected.
*/ return(NO);
}
"C"
"68000"
$EXTENSIONS ON$
```

```
$ASM_FILE$
$WARN OFF$
$FAR ON$
$CALL_ABS_LONG ON$
$LIB_ABS_LONG ON$
$INIT_ZEROES OFF$
#include "DEFINES"

extern int MULTIPLEXER,IO_CONTROL,AD_CONVERSION,TIMER2_CNTRL_REG,
           MSB3_BUFFER,TIMER3_LATCH,multiplexer,io_control,
           timer2_cntrl_reg;
extern short DATA_OK;

/*********************/
/************************   ACQUIRE DATA  ****************************/
                          /*********************/

/*
  Routine Name         : acquire_data
  Parameters Passed    : analog_signal -- multiplexer channel to be
                                          sampled
  Parameters Returned  : A/D conversion results
  Calling Routines     : manual_mode, cal_cuffp, real_time_interrupt,
                         bleed, check_cuff_pressure, check_system,
                         pump
  Routines Called      :  --
  Local Variables      : temp -- temporary storage
*/ acquire_data(analog_signal)
int analog_signal;
{int temp;

/*
  Reset invalid data flag.
*/

DATA_OK = YES;

/*
  Select analog multiplexer channel.
*/

MULTIPLEXER = multiplexer &= CLEAR_MUX_CHANNEL;
  MULTIPLEXER = multiplexer |= analog_signal;

/*
  Initiate A/D conversion.
*/

IO_CONTROL = io_control &= AD_START;
  temp = AD_CONVERSION;
  IO_CONTROL = io_control |= AD_READ;

/*
  Set a 40 microsecond delay time.  Set the invalid data flag if delay
  time is up and data is not converted.
*/

TIMER2_CNTRL_REG = timer2_cntrl_reg &= SELECT_PT3;
  MSB3_BUFFER = 00H;
  TIMER3_LATCH = 04H;

/*
  Wait for data ready bit to be set or the 40 microsecond delay time
  to be up.
*/
```

```
  while (((TIMER2_CNTRL_REG & PT3_TIME_OUT) == NO) &&
         (AD_CONVERSION & AD_DATA_NOT_READY))
    ;
  if (AD_CONVERSION & AD_DATA_NOT_READY)
    DATA_OK = NO;
  return(AD_CONVERSION & AD_DATA_MASK);
}
```

"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$

```
                        /*******************/
/***************************    ADD TIME    ****************************/
                        /*******************/

/*
 Routine Name       :  add_time
 Parameters Passed  :  time1 -- first time
                       time2 -- second time
 Parameters Returned:  time1 + time2
 Calling Routines   :  preprocess, bleed
 Routines Called    :  --
 Local Variables    :  sec  -- total seconds
                       min  -- total minutes
                       sec1 -- seconds of time1
                       min1 -- minutes of time1
                       sec2 -- seconds of time2
                       min2 -- minutes of time2
*/ add_time(time1,time2)
int time1,time2;
{int sec1,min1,sec2,min2,sec,min;

/*
 Initialize minute variable.
*/ min = 0;

/*
 Determine second and minute values.
*/ min1 = (short) (time1 / 100);
  sec1 = (short) (time1 % 100);
  min2 = (short) (time2 / 100);
  sec2 = (short) (time2 % 100);

/*
 Increment minutes and subtract 60 from seconds if the seconds variable
 overflows.
*/ if ((sec = sec1 + sec2) > 59){
    min++;
    sec -= 60;
  }

/*
 Subtract 100 from minutes if the minutes variable overflows.
*/
```

```
  if ((min = min1 + min2 + min) > 99)
    min -= 100;

/*
 Return calculated time.
*/ return( min * 100 + sec);
 }

"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$ extern double LN();

/*******************/
/*************************   ADJUST ATTEN   *****************************/
                          /*******************/

/*
 Routine Name           : adjust_atten
 Parameters Passed      : hi_peak -- maximum peak amplitude (peak to peak)
                          atten -- current attenuator setting
 Parameters Returned    : value -- adjusted attenuator setting
                          atten -- untouched attenuator setting
 Calling Routines       : process
 Routines Called        : set_atten
 Local Variables        : value -- adjusted attenuator setting
*/ adjust_atten(hi_peak,atten)
int hi_peak,atten;
{
 int value;

/*
 Make sure that the maximum peak amplitude found was a positive value.
*/ if (hi_peak > 0){

/*
 Adjust the programmable attenuator using the formula:
   Change in attenuation = 20 * log(maximum amplitude / desired amplitude).
 Since the common log is not available, use the conversion:
   log(n) = ln(n) / ln(10).
*/ value = ((LN(hi_peak / 2500.0) / 2.302585093) * 200) + atten;

/*
 Do not exceed attenuator limits.
*/ if (value > 199)
      value = 199;
    else if (value < 0)
      value = 0;
```

```
/*
 Set the attenuator to adjusted value and return.
*/
      set_atten(value);

return(value);
 }

/*
 A negative manximum amplitude was detected so return attenuator
 setting untouched.
*/ return(atten);
}

"C"
 "68000"
 $EXTENSIONS ON$
 $FAR ON$
 $CALL_ABS_LONG ON$
 $LIB_ABS_LONG ON$
 $ASM_FILE$
 $INIT_ZEROES OFF$
 $WARN OFF$
 #include "DEFINES"

extern int PUMP_UP,CUFFP_OFFSET,IO_CONTROL,io_control,ELAPSED_TIME,
            BLEED_DOWN,INTERVAL_END,LAST_CUFF_PRESSURE,
            HEART_RATE,BLEED_CRACK_POINT;
 extern unsigned int bleed_valve;
 extern short MODE_IS_START,MODE_IS_REST,MODE_IS_MANUAL,MODE_IS_EXEC,
              DATA_OK,MEASUREMENT_COMPLETE,BLEED_PROCESS_FINISHED,
              DATASET_COMPLETE,K,FIRST_BLEED,BLEED_RATE_ESTABLISHED,
              INITIAL_BLEED;
 extern unsigned short BLEED_VALVE;

/*******************/
/************************       BLEED       *****************************
                              /*******************/

/*
  Routine Name          :  bleed
  Parameters Passed     :  time -- time in ms between ECG triggers
  Parameters Returned   :  --
  Calling Routines      :  ecg_interrupt, manual_mode
  Routines Called       :  acquire_data, add_time
  Local Variables       :  temp -- temporary storage
                           count -- number of good data samples from the
                                 A/D
                           total -- summation of data sampling from the
                                 A/D
                           i -- loop counter
                           current_cuff_pressure -- bit representation of
                                                 the current cuff
                                                 pressure
                           deviation -- projected bleed rate (bits)
                           num -- value to add or subtract from the bleed
                                 valve to obtain the desired bleed rate
                                 (bits)
                           cuff_pressure_change -- the chang in cuff
                                                 pressure from previous
                                                 to current (bits)
                           depressurization_time -- cuff depressurization
```

```
                                                time from pump up to
                                                bleed down in seconds
                      cuff_depressurization -- amount to depressurize
                                                the cuff from pump up
                                                to bleed down (bits)
                      bleed_rate -- bleed rate (bits)
*/ bleed(time)
unsigned int time;
{int temp,total,count,i,current_cuff_pressure,deviation,num,
     cuff_pressure_change;
 static int depressurization_time,cuff_depressurization;
 short bleed_rate;

if (MODE_IS_START){

/*
 Sample cuff pressure on the multiplexer and get results from the A/D.
*/ for (i=count=total=0; i<AVG_COUNT; i++){
      if ((temp = acquire_data(CUFF_PRESSURE) - CUFFP_OFFSET) < 0)
         temp = 0;
      if (DATA_OK){
         total += temp;
         count++;
      }
    }
    if (count == 0)
      count = 1;

/*
 Obtain a reference cuff pressure value to start the bleed process.
*/
    if (FIRST_BLEED){
      FIRST_BLEED = NO;
      LAST_CUFF_PRESSURE = total / count;

/*
 Determine the cuff pressure depressurization amount and time for the
 Exercise mode.
*/ if (MODE_IS_EXEC){
         cuff_depressurization = PUMP_UP - BLEED_DOWN;
         depressurization_time = (((float) cuff_depressurization /
                                   (float) (FIVE_mmHg * HEART_RATE)) * 60.0);
      }
      return;
    }

/*
 Get a current cuff pressure value and determine amount of change
 seen since last time the procedure was called.
*/ current_cuff_pressure = total / count;
    cuff_pressure_change = LAST_CUFF_PRESSURE - current_cuff_pressure;

/*
 Test for end of bleed processing.
*/ if (DATASET_COMPLETE || current_cuff_pressure < BLEED_DOWN){
       IO_CONTROL = io_control &= DUMP_VALVE_OPEN;
```

```
        BLEED_VALVE = bleed_valve = BLEED_VALVE_OPEN;

/*
A mandatory 10 second rest period after measurement cycles is
enforced.
*/ if (MEASUREMENT_COMPLETE){
           if ((temp = add_time(ELAPSED_TIME, 10)) > INTERVAL_END)
              INTERVAL_END = temp;

}
        BLEED_PROCESS_FINISHED = YES;
        return;
     }

/*
Bleed rate for the Rest mode is based on 3 mmHg per ECG.
The calculation for this is (3 mmHg / ECG) / CUFFP_CONV.
*/ if (MODE_IS_REST)
        bleed_rate = deviation = THREE_mmHg;

/*
Bleed rate for the Manual mode is based on 3 mmHg per second.
The calculation for this is (3 mmHg / CUFFP_CONV) / half second.
*/ else if (MODE_IS_MANUAL)
        bleed_rate = deviation = 13;

/*
Bleed rate for the Exercise mode is based on 5 mmHg per ECG.
Time constraints must be enforced in this mode.  A 20 second bleed
rate is enforced if depressurization time is less than 20 seconds.
A 30 second bleed rate is enforced if depressurization time is greater
than or equal to 30 seconds.  A 5 mmHg bleed rate is used when the
depressurization time is less than 30 seconds and greater than 20.
*/ else if (MODE_IS_EXEC){
        if (time <= 0)
           time = 1;
        if (depressurization_time <= 20)
           bleed_rate = deviation = cuff_depressurization / (17000 / time);
        else if (depressurization_time > 30)
           bleed_rate = deviation = cuff_depressurization / (27000 / time);
        else
           bleed_rate = deviation = FIVE_mmHg;
     }

/*
Eliminate excessive decreases in the bleed valve opening by one half
when the change in cuff pressure is negative.
*/ if (cuff_pressure_change < 0)
        cuff_pressure_change /= 2;

/*
Calculate the bleed valve adjustment.
*/ num = deviation - cuff_pressure_change;

/*
```

Allow only openings of the bleed valve to occur until the
bleed rate is established.
*/

```
   if (!BLEED_RATE_ESTABLISHED){
     if (num < 0)
        num = 0;

if (num > 10)
        num = 10;
     if (cuff_pressure_change >= bleed_rate){
        if (++K >= 2){
```

/*
Determine the valve crack point if this is the first bleed of the
Rest mode.
*/

```
          if (INITIAL_BLEED){
            temp = bleed_valve + 10;
            if (temp > 255)
               temp = 255;
            if (temp < BLEED_VALVE_CLOSED){
               INITIAL_BLEED = NO;
               BLEED_CRACK_POINT = temp;
            }
            else
               K = 0;
          }
          else
             BLEED_RATE_ESTABLISHED = YES;
        }
     }
     else
        K = 0;
   }
```

/*
Allow positive and negative adjustments to the bleed valve once the
bleed rate has been established.
*/

```
   else if (num > 10)
     num = 10;
   else if (num < -10)
     num = -10;
   bleed_valve -= num;
```

/*
Do not exceed limitations of the bleed valve.
*/

```
   if (bleed_valve > 255)
     bleed_valve = 255;
   BLEED_VALVE = (short)bleed_valve;

LAST_CUFF_PRESSURE = current_cuff_pressure;
 }
}

"C"
"68000"
$EXTENSIONS ON$
$ASM_FILE$
$WARN OFF$
$FAR ON$
$EXTENSIONS ON$
$CALL_ABS_LONG ON$
```

```
$LIB_ABS_LONG ON$
$INIT_ZEROES OFF$
#include "DEFINES"

extern unsigned int bleed_valve;
extern int CUFFP_OFFSET,IO_CONTROL,io_control,REG_A,REG_B;
extern short IN_CAL_CUFFP,PIR_DETECTED,DATA_OK;
extern unsigned short BLEED_VALVE;
```

/********************/
/********************** CAL_CUFFP **************************
/********************/

```
/*
 Routine Name        : cal_cuffp
 Parameters Passed   : -
 Parameters Returned : cuff pressure offset value
 Calling Routines    : preprocess, manual_mode
 Routines Called     : acquire_data
 Local Variables     : not_steady        -- flag to indicate whether
                                            or not to continue
                       time_count        -- counter to control delay
                                            before processing
                       percentage        -- percent of flucuation
                                            that will be allowed
                       zero_pressure     -- the cuff pressure offset
                       margin            -- variation in cuff pressure
                                            allowed
                       old_cuffp_offset  -- previous offset value
                       total             -- averaging register
                       count             -- averaging samples taken
                       avg_count         -- number of samples to take
                       temp              -- current raw cuff pressure
                       i                 -- loop control
*/ cal_cuffp()
{
/*
 Declare the local variables.
*/
   char not_steady = TRUE;
   int time_count,
       percentage,
       zero_pressure, margin, old_cuffp_offset, temp;
   long i, total, count, avg_count;

/*
 Initialize local and global variables; open bleed and dump valves.
*/
   IN_CAL_CUFFP = YES;
   time_count = 2;
   percentage = 50;
   avg_count = 100;
   old_cuffp_offset = CUFFP_OFFSET;
   IO_CONTROL = (io_control &= DUMP_VALVE_OPEN);
   BLEED_VALVE = bleed_valve &= BLEED_VALVE_OPEN;
   REG_A = PIR_500;
   PIR_DETECTED = NO;

/*
 Continue the process until the difference between 2 successive
 cuff pressure offsets is within the allowable error.
*/
   while (not_steady) {

/*
 Wait for 1 second
```

```
        REG_B |= ENABLE_PIE;
        for (i = 0; i < time_count; i++) {
           while (!PIR_DETECTED)
              ;
           PIR_DETECTED = NO;
        }
        REG_B &= DISABLE_PIE;

/*
 Cuff pressure should be at zero; find the current value of pressure
  transducer.
*/
        for (i = count = total = 0; i < avg_count; i++) {
           temp = acquire_data(CUFF_PRESSURE);
           if (DATA_OK) {
              total += temp;
              count++;
           }
        }
        if (count == 0)
          count = 1;

/*
 Calculate the allowable margin of error.
*/
        margin = (zero_pressure = total / count) / percentage;

/*
 Check to see if we are within tolerance.
*/
        if (zero_pressure < old_cuffp_offset + margin &&
            zero_pressure > old_cuffp_offset - margin) {
           not_steady = FALSE;
        }

/*
 Make the new value the old value for next iteration if necessary.
*/
        old_cuffp_offset = zero_pressure;
     }

/*
 Return the new zero pressure reference, 'CUFFR_OFFSET'.
*/
    IN_CAL_CUFFP = NO;
    return(zero_pressure);
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern short DATA_OK,DIAGNOSTIC_SELFTEST,FAILED_SELFTEST;

/***********************/
/************************ CHECK CUFF PRESSURE ***************************/
                      /***********************/

/*
 Routine Name        :  check_cuff_pressure
```

```
 Parameters Passed     :   --
 Parameters Returned   :   --
 Calling Routines      :   selftest_mode
 Routines Called       :   halt, acquire_data
 Local Variables       :   temp -- temporary storage
*/ check_cuff_pressure()
{int temp;

/*
 Sample signal on the cuff pressure multiplexer channel.  Generate an
 error condition if the results from the A/D are not within -3.0 to -4.0
 volt range.
*/ temp = acquire_data(CUFF_PRESSURE);
  if (convert(temp) < -4.0 || convert(temp) > -3.0 && DATA_OK){
    if (DIAGNOSTIC_SELFTEST)
       halt(40,selftest);
    FAILED_SELFTEST = YES;
  }
}

"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int ALARM_LED,alarm_led,SWITCH_LED,switch_led;

/********************/
/************************  CHECK DISPLAYS  **************************/
                      /********************/
/*
 Routine Name          :   check_displays
 Parameters Passed     :   --
 Parameters Returned   :   --
 Calling Routines      :   selftest_mode
 Routines Called       :   second_delay
 Local Variables       :   temp -- temporary storage
*/ check_displays()
{int temp;

/*
 Turn on all LED's and put the displays in the Lamp Test mode.
 Sound the tone alarm for one second.
*/

ALARM_LED = alarm_led |= (ALARM_LEDS_ON | TONE_ALARM_ON);
  SWITCH_LED = switch_led &= LAMP_TEST_ON;
  SWITCH_LED = switch_led |= (SWITCH_LEDS_ON | OSCIL_LED_ON);
  second_delay(1);

/*
 Turn off all LED's, lamp test, and tone alarm.  This sequence
 of steps leaves the K-SOUND LED on.
*/
```

```
ALARM_LED = alarm_led &= (ALARM_LEDS_OFF & TONE_ALARM_OFF);
SWITCH_LED = switch_led &= (SWITCH_LEDS_OFF & OSCIL_LED_OFF);
SWITCH_LED = switch_led |= LAMP_TEST_OFF;
}

"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int SYS_DISPLAY,PRP_DISPLAY;
extern short DIAGNOSTIC_SELFTEST,FAILED_SELFTEST;

/********************/
/************************  CHECK RAM   *****************************/
                           /********************/

/*
  Routine Name         :   check_ram
  Parameters Passed    :   --
  Parameters Returned  :   --
  Calling Routines     :   selftest_mode
  Routines Called      :   ram_test, halt, display
  Local Variables      :   badram -- number of bad RAM words encountered
                                     during the test
*/ check_ram()
{int badram;

/*
 Send message to the displays when in the Diagnostic Self-test mode.
*/ if (DIAGNOSTIC_SELFTEST)
    display(&SYS_DISPLAY,"TESTRAM  ",8,-2,8);

/*
 Perform test on all RAM's.
*/ badram = ram_test();

/*
 Check to see if any RAM's failed the test.  Display the error message
 when in the Diagnostic Self-test mode.
*/ if (badram){
    if (DIAGNOSTIC_SELFTEST){
      halt (20,selftest);
    }
    FAILED_SELFTEST = YES;
  }

/*
 Blank displays when in the Diagnostic Self-test mode.
*/ if (DIAGNOSTIC_SELFTEST)
    display(&PRP_DISPLAY,"",0,-2,8);
```

```
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int REG_A, REG_B, MONTH, YEAR, DATE, HOUR, MINUTE;

/*************************/
/*********************** CHECK REAL TIME CLOCK ********************/
                    /*************************/

/*
  Routine Name         :  check_real_time_clock
  Parameters Passed    :  --
  Parameters Returned  :  --
  Calling Routines     :  selftest_mode
  Routines Called      :  validate
  Local Variables      :  --
*/ check_real_time_clock()
{

/*
  Inhibit any Real-Time Clock calendar or time updates.
*/ while (REG_A & UPDATE_CYCLE_IN_PROGRESS)
    ;
  REG_B |= STOP_UPDATE_CYCLE;

/*
  Validate all Real-Time Clock settings.  Assign the 12 position
  switch parameter to the minimal setting if data is invalid.
  Assign the value of 84 when the YEAR setting is invalid.
*/ validate(&MONTH,12,1,month);
  validate(&YEAR,99,YEAR_SETTING,year);
  validate(&DATE,0,1,date);
  validate(&HOUR,23,0,hour);
  validate(&MINUTE,59,0,minute);

/*
  Allow normal Real-Time Clock calendar and time updates.
*/

REG_B &= RESUME_UPDATE_CYCLE;
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"
```

```
extern int SYS_DISPLAY;
extern short DIAGNOSTIC_SELFTEST,FAILED_SELFTEST;

/********************/
/*************************  CHECK ROM  *****************************/
                          /********************/

/*
  Routine Name          :  check_rom
  Parameters Passed     :  --
  Parameters Returned   :  --
  Calling Routines      :  selftest_mode
  Routines Called       :  display, halt, crctst
  Local Variables       :  badrom --  indicates which set of ROM's is bad;
                                       a 0 means bad and a 1 means good
                           ptr -- pointer to bad ROM indicator
                           i --   loop counter

*/ check_rom()
{short i,badrom;
 int ptr;

/*
 Display message to user when in the Diagnostic Self-test mode.
*/ if (DIAGNOSTIC_SELFTEST)
    display(&SYS_DISPLAY,"TESTROM  ",8,-2,8);

/*
 Perform CRC test on all ROM's.
*/ badrom = crctst();

/*
 Check to see which ROM's failed.  Display error message if in the
 Diagnostic Self-test mode.
*/ for (i = 10, ptr = 1; ptr != 4H && badrom != 0; i++){
    if ((ptr & badrom) != 0){
       if (DIAGNOSTIC_SELFTEST)
          halt(i,selftest);
       FAILED_SELFTEST = YES;
    }
    ptr = ptr << 1;
 }
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern short DATA_OK,DIAGNOSTIC_SELFTEST,FAILED_SELFTEST;

/********************/
/*************************  CHECK SYSTEM  ****************************/
                          /********************/
```

```
/*
Routine Name         : check_system
Parameters Passed    : --
Parameters Returned  : --
Calling Routines     : selftest_mode, manual_mode, preprocess
Routines Called      : halt, acquire_data
Local Variables      : value -- result from the A/D
*/ check_system()
{int value;

/*
Sample signal on the +5 volt multiplexer channel.  Generate an error
condition if results from the A/D are not in the + 1.25 +- 10 percent
range.
*/ value = acquire_data(PLUS_5V);
  if (convert(value) >= 1.375 && convert(value) <= 1.125 && DATA_OK){
    if (DIAGNOSTIC_SELFTEST)
      halt(30,selftest);
    FAILED_SELFTEST = YES;
  }

/*
Sample signal on the +15 volt multiplexer channel.  Generate an error
condition if results from the A/D are not in the + 3.75 +- 2 percent
range.
*/ value = acquire_data(PLUS_15V);
  if (convert(value) >= 3.825 && convert(value) <= 3.675 && DATA_OK){
    if (DIAGNOSTIC_SELFTEST)
      halt(31,selftest);
    FAILED_SELFTEST = YES;
  }

/*
Sample signal on the -5 volt multiplexer channel.  Generate an error
condition if results from the A/D are not in the + 1.25 +- 10 percent
range.
*/ value = acquire_data(MINUS_5V);
  if (convert(value) >= -1.125 && convert(value) <= -1.375 && DATA_OK){
    if (DIAGNOSTIC_SELFTEST)
      halt(32,selftest);
    FAILED_SELFTEST = YES;
  }

/*
Sample signal on the -15 volt multiplexer channel.  Generate an error
condition if results from the A/D are not in the - 3.75 +- 2 percent
range.
*/ value = acquire_data(MINUS_15V);
  if (convert(value) >= -3.675 && convert(value) <= -3.825 && DATA_OK){
    if (DIAGNOSTIC_SELFTEST)
      halt(33,selftest);
    FAILED_SELFTEST = YES;
  }

/*
Sample signal on the digital ground multiplexer channel.  Generate an
error condition if the results from the A/D are not less than 0.1 volt.
*/
```

```
value = acquire_data(DIGITAL_GROUND);
if (convert(value) >= 0.1 && DATA_OK){
   if (DIAGNOSTIC_SELFTEST)
     halt(34,selftest);
   FAILED_SELFTEST = YES;
}

/*
Sample signal on the analog ground multiplexer channel.  Generate an
error condition if the results from the A/D are not less than 0.1 volt.
*/
value = acquire_data(ANALOG_GROUND);
if (convert(value) >= 0.1 && DATA_OK){
   if (DIAGNOSTIC_SELFTEST)
     halt(35,selftest);
   FAILED_SELFTEST = YES;
}
}
"68000"
```

```
;                              /*******************/
;****************************    CLEAR_SR    ****************************/
;                              /*******************/
;

;Routine Name         : clear_sr
;Parameters Passed    : -2[A6] -- interrupt mask level to clear
;Parameters Returned  :   --
;Calling Routines     : preprocess, initialize, abort2
;Routines Called      :   --
;Local Variables      : D0 -- temporary storage
;                       -2[A6] -- temporary storage PROG
         GLOBAL clear_sr
clear_sr
         LINK     A6,#-2
         CLR      -2[A6]           ;clear temporary storage allocation
         MOVE     8[A6],D0         ;get interrupt mask
         MOVE     SR,-2[A6]        ;get current Status Register contents
         AND      D0,-2[A6]        ;mask interrupt with current Status Register
         MOVE     -2[A6],SR        ;replace Status Register with masked value
         UNLK     A6
         RTS
      END
"68000" LIST
```

```
;                              /*******************/
;****************************    CRCTST     ****************************/
;                              /*******************/
;

;Routine Name         : CRCtst
;Parameters Passed    :   --
;Parameters Returned  : D7 -- flag indicating individual ROM's that
;                             failed.  A "0" means the ROM's passed
;                             the CRC test; a "1" means they failed.
;Calling Routines     : check_rom
;Routines Called      :   --
;Local Variables      : D0 -- ROM bit pointer
;                       D1 -- bad ROM pointer (by chip)
;                       D2 -- CRC value
;                       D3 -- temporary storage
;                       A0 -- ROM table pointer
;                       A1 -- ROM start address
;                       A2 -- ROM end address
;                       A3 -- result table address
;                       A4 -- stored result address
```

GLOBAL crctst

PROG

```
crctst    CLR.B D7                    ;clear bad ROM flag
          MOVE.B #-1,D1               ;initialize bad ROM pointer
          MOVE.L #RSTTBL,A3           ;get result table pointer
          MOVE.L #ADRTBL,A0           ;get ROM address table pointer
NXTROM    ADDQ.B #1,D1                ;increment bad ROM pointer
          MOVE.L [A0]+,A1             ;get ROM start address
          MOVE.L [A0],A2              ;get ROM stop address
          CMP.L A1,A2                 ;finished?
          BEQ FINISHED                ;yes-return
          CLR.W D2                    ;no--clear CRC value
TSTWORD   MOVE.W #15,D0               ;initialize bit pointer
          MOVE.W [A1],D3              ;get ROM contents
TSTBIT    TST.W D0                    ;finished with word?
          BMI NXTWORD                 ;yes-get next word
          LSR #1,D2                   ;no--shift CRC value to establish carry
          BTST.L D0,D3                ;test bit
          BEQ CONTINUE                ;bit=0; carry=1; change CRC value
          BCS NOCHG                   ;bit=1; carry=1; no change to CRC value
          BRA CHANGE                  ;bit=1; carry=0; change CRC value
CONTINUE  BCC NOCHG                   ;bit=0; carry=0; no change to CRC value
CHANGE    EORI.W #10A0H,D2            ;exor CRC value with polynomial
NOCHG     SUBQ #1,D0                  ;next bit
          BRA TSTBIT
NXTWORD   ADDQ.L #2,A1                ;next word
          CMP.L A1,A2                 ;finished testing chip?
          BNE TSTWORD                 ;no--test next byte
          MOVE.W D2,74000H            ;yes-store CRC value for access to EPROM
          MOVE.L [A3]+,A4             ;get prestored result
          CMP.W [A4],D2               ;compare prestored CRC with computed CRC
          BEQ NXTROM                  ;equal--next ROM
          BSET.B D1,D7                ;differ-flag bad ROM chip
          BRA NXTROM                  ;next ROM
FINISHED  EXT.L D7                    ;return bad ROM flag
          RTS
          ADRTBL    DC.L    0,08000H,0FFFAH,0FFFAH
          RSTTBL    DC.L    00FFFCH,00FFFEH
          END
"C"
"68000"
$EXTENSIONS ON$
$FAR ON$
$CALL_ABS_LONG ON$
$LIB_ABS_LONG ON$
$ASM_FILE$
$INIT_ZEROES OFF$
$WARN OFF$
include "DEFINES"

extern int TIMER2_CNTRL_REG,timer2_cntrl_reg,MSB3_BUFFER,TIMER3_LATCH,
           TIMER1_3_CNTRL_REG,timer1_3_cntrl_reg;

/********************/
/************************    DELAY    **************************/
                         /********************/

/*
Routine Name        : delay
Parameters Passed   : msb -- most significant byte
                      lsb -- least significant byte
Parameters Returned :   --
Calling Routines    : program, read_sw
Routines Called     :   --
Local Variables     :   --
*/
```

```
delay(msb,lsb)
short msb,lsb;
{

/*
  Select Timer 3 of the Programmable Timer and load delay times into the
  Timer's buffer.
*/

TIMER2_CNTRL_REG = timer2_cntrl_reg &= SELECT_PT3;
  MSB3_BUFFER = msb;
  TIMER3_LATCH = lsb;

/*
  Wait for delay time to expire.
*/ while ((TIMER2_CNTRL_REG & PT3_TIME_OUT)==NO)
      ;
}
"C"
"68000"
$EXTENSIONS ON$
$FAR ON$
$CALL_ABS_LONG ON$
$LIB_ABS_LONG ON$
$INIT_ZEROES OFF$
$WARN OFF$
$ASM_FILE$
#include "DEFINES"

extern short NULL;
extern long table1[5];

/********************/
/****************************   DISPLAY    *****************************/
                          /********************/
/*
  Routine Name          : display
  Parameters Passed     : *display_loc -- display address
                          message -- string array containing message to be
                                     displayed
                          m_limit -- string length
                          value -- digital value to be displayed
                          v_limit -- value length
  Parameters Returned   : --
  Calling Routines      : halt, manual_mode, real_time_interrupt, pump,
                          ecg_interrupt, program, preprocess, initialize,
                          abort3, abort2, process, standby_mode, main
  Routines Called       : --
  Local Variables       : temp -- temporary storage
                          i -- loop and index counter
*/ display(display_loc,message,m_limit,value,v_limit)
int *display_loc,m_limit,v_limit,value;
char message[];
{int temp,i;

/*
  Display numerical value first.
*/ switch (value){

/*
```

```
  No value is to be displayed.
*/ case -1  : break;
/*
 Display blanks only.
*/ case -2  : for (i=0; i<=v_limit; i++){
                *display_loc++ = BLANK;
              }
              break;
/*
 Display number after removing leading zeroes and converting to ASCII
 format.
*/
   default : for (i=v_limit; i>=0; i--){
                temp = value/table1[i];
                if (temp==0 && NULL && i!=0)
                   *display_loc++ = BLANK;
                else{
                   *display_loc++ = temp + 48;
                   NULL = NO;
                }
                value=value-(temp * table1[i]);
              }
              break;
   }
/*
 Display message if string parameter has been passed.
*/ if (m_limit > 0){
      for (i=0; i<=m_limit; i++){
         *display_loc++ = message[i];
      }
   }
   NULL = YES;
}
"C"
'68000'
$EXTENSIONS ON$
$FAR ON$
$WARN OFF$
$INIT_ZEROES OFF$
$CALL_ABS_LONG ON$
$LIB_ABS_LONG ON$
$ASM_FILE ON$
#define FILTER_VALUE 2

/********************/
/****************************   EXP_FILTER   ****************************/
                              /********************/
/*
* Routine Name          : exp_filter
* Parameters Passed     : input  - address of unfiltered input data set
*                         output - address of filtered output data set
*                         length - length of data set
* Parameters Returned   : -
* Calling Routines      : process
* Routines Called       : -
* Local Variables       : temp_exp - name for data set that holds
*                                    the data between 1st and 2nd pass.
*                         i        - array pointer
*/

/*
```

```
* Exponential filter or weighted average subroutine.
*   This filter is used on the distal data to enhance the the pulse
*   data envelope. The filter smooths positive and negative transitions
*   by adding a fraction of the difference between the current pulse
*   amplitude and the previous pulse amplitude to the previous pulse.
*   The sum becomes a data point in a new data set.
*
* The data set is passed through the filter twice. Once from beginning
*   to end and once from end to beginning. This is done to negate the
*   the phase shift characteristic of the filter.
*/
exp_filter(input, output, length)
int input[], output[], length;
{
   int i, temp_exp[100];

/*
* Perform the first pass from left to right putting the results
*   in the temporary array.
*/
   temp_exp[0] = input[0];

for(i = 1; i < length; i++) {
      temp_exp[i] = input[i - 1] +
                    ((input[i] - input[i - 1]) / FILTER_VALUE);
   }

/*
* Perform the second pass from right to left putting the results
*   in the output array.
*/
   output[length - 1] = temp_exp[length - 1];
      for(i = length - 2; i >= 0; i--) {
         output[i] = temp_exp[i + 1] +
                     ((temp_exp[i] - temp_exp[i + 1]) / FILTER_VALUE);
      }
   }

"C"
"68000"
$EXTENSIONS ON$
$FAR ON$
$WARN OFF$
$INIT_ZEROES OFF$
$CALL_ABS_LONG ON$
$LIB_ABS_LONG ON$
#include "DEFINES"

extern int MAX_AMPLITUDE,SIZE,MAX_POSITION;
extern unsigned RAW_DATA_POSITION;
extern short BLEED_PROCESS_FINISHED,INTERVAL_UP,MODE_IS_STOP;
```

/********************/
/*******************    FIND_MAX    *******************/
/********************/

```
/*
   Routine Name         : find_max
   Parameters Passed    : array, begin, start, length
   Parameters Returned  : index
   Calling Routines     : process
   Routines Called      : -
   Local Variables      : peak_not_found          -- flag for loop control
                          current_minima_position -- position in array of
                                                     current minima
                          current_maxima_position -- position in array of
                                                     current maxima
```

|  |  |
|---|---|
| time_between_peaks | -- time between current minima and maxima |
| index | -- current position in array |
| end | -- last position in array to search |
| minimum_time | -- minimum time allowed between current minima and maxima |
| maximum_time | -- maximum time allowed between current minima and maxima |
| current_minima | -- digital value of current minima |
| current_maxima | -- digital value of current maxima |
| temp1 | -- current peak-to-peak value |
| temp2 | -- location of current peak_to_peak value |

```
*/

$PAGE$
/* ******************************************************************** */
/*                                                                      */
/*    Peak detection subroutine                                         */
/*                                                                      */
/* ******************************************************************** */
find_max(array, begin, start, length)
int array[], start;
unsigned int begin, length;
{
    char peak_not_found;
    unsigned int  current_minima_position, current_maxima_position,
                  time_between_peaks, index, end, temp2;
    int minimum_time, maximum_time,
        current_minima, current_maxima,
        temp1;

/*
   Initialization
*/
    index = begin + start;
    current_minima_position = current_maxima_position = index;
    MAX_POSITION = index;
    current_minima = current_maxima = MAX_AMPLITUDE = 0;
    minimum_time = 4 / SAMPLE_INTERVAL;
    maximum_time = 24 / SAMPLE_INTERVAL;
    end = index + length;
    peak_not_found = TRUE;

/*
   Begin processing and continue until end of window.
*/
    while (index < end) {

/*
   Find a minimum point. Synchronize with data collection by not getting
   ahead of position indicated in 'RAW_DATA_POSITION'.
*/
        while (peak_not_found) {
            if (index < RAW_DATA_POSITION) {
                if (array[(index + 1) % SIZE] > array[index % SIZE])
                    peak_not_found = FALSE;
                index++;
                if (index > end)
                    return(index);
            }
```

```
/*
 Check a few external flags so we don't get stuck.
 */
        if (BLEED_PROCESS_FINISHED || INTERVAL_UP || MODE_IS_STOP)
           return;
      }
/*
 Found a minima; use last maxima data to find current peak-to-peak
  amplitude and position.
 */
      peak_not_found = TRUE;
      current_minima = array[(index - 1) % SIZE];
      current_minima_position = index - 1;
      time_between_peaks = current_minima_position - current_maxima_position;

/*
 Check time between this minima and current maxima for validity; save
  ampitude and position if amplitude is highest so far.
 */
      if (time_between_peaks >= minimum_time  &&
          time_between_peaks <= maximum_time) {
         temp1 = current_maxima - current_minima;
         temp2 = current_maxima_position +
            ((current_minima_position - current_maxima_position) / 2);
         if (temp1 > MAX_AMPLITUDE  &&  temp2 >= begin) {
            MAX_AMPLITUDE = temp1;
            MAX_POSITION = temp2;
         }
      }

/*
  Find a maximum point. Synchronize with data collection by not getting
   ahead of position indicated in 'RAW_DATA_POSITION'.
 */
      while (peak_not_found) {
         if (index < RAW_DATA_POSITION) {
            if (array[(index + 1) % SIZE] < array[index % SIZE])
               peak_not_found = FALSE;
            index++;
            if (index > end)
               return(index);
         }
/*
 Check a few external flags so we don't get stuck.
 */
        if (BLEED_PROCESS_FINISHED || INTERVAL_UP || MODE_IS_STOP)
           return;
      }
/*
 Found a maxima; use last minima data to find current peak-to-peak
  amplitude and position.
 */
      peak_not_found = TRUE;
      current_maxima = array[(index - 1) % SIZE];
      current_maxima_position = index - 1;
      time_between_peaks = current_maxima_position - current_minima_position;

/*
 Check time between this maxima and current minima for validity; save
  ampitude and position if amplitude is highest so far.
 */
      if (time_between_peaks >= minimum_time  &&
          time_between_peaks <= maximum_time) {
         temp1 = current_maxima - current_minima;
         temp2 = current_minima_position +
            ((current_maxima_position - current_minima_position) / 2);
```

```
            if (temp1 > MAX_AMPLITUDE  &&   temp2 >= begin) {
               MAX_AMPLITUDE = temp1;
               MAX_POSITION = temp2;
            }
         }
      } return(index);
   }
"C"
"68000"
$EXTENSIONS ON$
$CALL_ABS_LONG ON$
$LIB_ABS_LONG ON$
$INIT_ZEROES OFF$
$FAR ON$
$WARN OFF$
$ASM_FILE$
#include "DEFINES"

extern int SWITCH_LED,switch_led,ALARM_LED,alarm_led,SYS_DISPLAY,
           PRP_DISPLAY,SELECTION;
extern short MODE_IS_HALT;

/********************/
/*************************     HALT      ****************************/
                       /********************/

/*
 Routine Name          : halt
 Parameters Passed     : err -- error number
                         setting -- current programmable switch setting
                                    at time of routine call
 Parameters Returned   : --
 Calling Routines      : check_rom, check_ram, check_cuff_pressure,
                         check_system
 Routines Called       : second_delay, read_sw, display
 Local Variables       : --
*/ halt(err,setting)
int setting,err;
{

/*
 Place the unit in the STOP state.
*/

MODE_IS_HALT = YES;
  SWITCH_LED = switch_led |= STOP_LED_ON;

/*
 Display error number and message.
*/ display (&SYS_DISPLAY,"",0,-2,8);
  display (&PRP_DISPLAY,"ERROR",4,err,3);

/*
 Sound tone alarm for one second.
*/

ALARM_LED = alarm_led |= TONE_ALARM_ON;
  second_delay(1);
  ALARM_LED = alarm_led &= TONE_ALARM_OFF;
```

```
/*
 Wait for the operator to select the appropriate setting necessary
 to continue processing.
*/
 read_sw();
 while ((SELECTION & setting)==0)
   read_sw();

/*
 Remove error message from display and return to processing at the point
 of error detection.
*/ display (&PRP_DISPLAY,"",0,-2,8);
 SWITCH_LED = switch_led &= STOP_LED_OFF;
 MODE_IS_HALT = NO;
)
"C"
"68000"
$EXTENSIONS ON$
$FAR ON$
$CALL_ABS_LONG ON$
$LIB_ABS_LONG ON$
$WARN OFF$
$ASM_FILE$
$INIT_ZEROES OFF$
#include "DEFINES"

extern unsigned int bleed_valve;
extern int REG_A,REG_B,SYS_DISPLAY,ALARM_LED,alarm_led,SWITCH_LED,
           switch_led,IO_CONTROL,io_control,MULTIPLEXER,multiplexer,
           REG_C,REG_D,TIMER1_3_CNTRL_REG,TIMER2_CNTRL_REG,MSB1_BUFFER,
           MSB2_BUFFER,TIMER1_LATCH,TIMER2_LATCH,timer1_3_cntrl_reg,
           timer2_cntrl_reg,ACIA1_CNTRL_STAT_REG,ACIA2_CNTRL_STAT_REG,
           INT_MASK_REG,MAX_SYSTOLIC,MAX_DIASTOLIC,MAX_CUFF,MAX_MMHG,
           MAX_HEART,LEAD,TRIGGER_LEAD,SECOND_BEST,SELECTION,SIZE,
           DUAL_LED,DI_COUNT,PI_COUNT,BLEED_CRACK_POINT,PI_ATTEN,DI_ATTEN;
extern short MODE_IS_START,PIR_DETECTED,DATA_OK,ABORT3,SHOW_TIME,
           ecg_control,NULL,IN_PUMP,ALARM_ON,ABORT2,
           MODE_IS_STOP,REST_MODE_STATUS,SELFTEST_OLD_STATE,
           REST_EXEC_OLD_STATE,MANUAL_OLD_STATE,LEAD_MONITORING,
           IN_CAL_CUFFP,IN_SECOND_DELAY,MODE_IS_REST,MODE_IS_EXEC,
           MODE_IS_MANUAL,MODE_IS_PROGRAM,MODE_IS_MODIFY,MODE_IS_HALT,
           MODE_IS_SELFTEST,GOOD_REST_DATA,EXEC_WAS_PREVIOUS_MODE,
           MODE_TRANSITION,FAILED_SELFTEST,LEAD_SELECTION_COMPLETE,
           DATASET_COMPLETE,PROCESSING_LEAD_SELECTION,LEAD_PROGRESS,
           STATUS_OF_LEAD_SELECTION_PROCESSING,MODE_IS_STANDBY,
           PREVIOUS_ERROR_CONDITION,BLEED_PROCESS_FINISHED,
           LEAD_STATUS,LEADS_PROCESSED,CLOCK_RUNNING,NO_ECG_FOUND,
           LEAD1[],LEAD2[],LEAD3[],BAD[],FIRST_TIME,ERROR_CONDITION,
           PI_DI_AMP_AVG_COMPLETE,SAMPLING_PI_DI,PROGRAMMED_MAX_CUFF;
extern unsigned short BLEED_VALVE,ECG_CONTROL,I;
extern float LEAD1_SIGNAL_NOISE_RATIO,LEAD2_SIGNAL_NOISE_RATIO,
           SUM_DI_AMP,SUM_PI_AMP,
           AVG_DI_ARRAY[],AVG_PI_ARRAY[],
           LEAD3_SIGNAL_NOISE_RATIO;

/*********************/
/*************************   INITIALIZE   **************************/
                        /*********************/

/*
 Routine Name         : Initialize.
 Parameters Passed    :  --
 Parameters Returned  :  --
 Calling Routines     : main
 Routines Called      : clear_sr, display
```

Local Variables     :  temp -- temporary storage
*/

```
initialize()
{int temp;

/*
 Initialize the I/O control software and hardware locations but
   wait until programmable timer is initialized before initializing
   the attenuators.
*/
IO_CONTROL = io_control = (AD_READ | PUMP_OFF) &
                          SET_ATTEN_0db &
                          DUMP_VALVE_OPEN &
                          DISABLE_PROXIMAL_ATTEN &
                          DISABLE_DISTAL_ATTEN;

BLEED_VALVE = bleed_valve = BLEED_VALVE_OPEN;
BLEED_CRACK_POINT = 255;

ECG_CONTROL = ecg_control = (FLOAT_RESET_HIGH | DISABLE_ECG_TESTS) &
                            DISABLE_ECG_INT & CLEAR_LEAD_SELECTION;

display(&SYS_DISPLAY,"".0,-2,17);

ALARM_LED = alarm_led = ALARM_LEDS_OFF & TONE_ALARM_OFF;

SWITCH_LED = switch_led = LAMP_TEST_OFF & OSCIL_LED_OFF & DISABLE_SS_INT &
                         SWITCH_LEDS_OFF;
temp = DUAL_LED;

MULTIPLEXER = multiplexer = DISABLE_ANALOG_FILTER_TEST;

/*
 MC146818 Real-Time Clock Initialization.
*/

REG_B = (STOP_UPDATE_CYCLE | BINARY_MODE | HOUR_24 | DAYLIGHT_SAVINGS_TIME)
        & (DISABLE_PIE & DISABLE_AIE & DISABLE_UIE);
if ((REG_A & DIVIDER_SELECTION_BITS) != TIME_BASE_4_194304MHz)
   REG_A = RESET_DIVIDER_CHAIN;
REG_A = SELECT_4_194304MHz_TIME_BASE & DISABLE_PIR;
temp = REG_C;
temp = REG_D;
REG_B &= RESUME_UPDATE_CYCLE;

/*
 MC6840 Programmable Timer Module Initialization.
*/

TIMER2_CNTRL_REG = timer2_cntrl_reg = SELECT_PT3;
TIMER1_3_CNTRL_REG = timer1_3_cntrl_reg = (CONTINOUS_OPERATING_MODE |
                                          PRESCALE_8 | ENABLE_CLOCK) &
                                          DISABLE_PT_OUTPUT & DISABLE_PT_INT
                                          & COUNTING_MODE_16_BIT;
TIMER2_CNTRL_REG = timer2_cntrl_reg = (ENABLE_PT_OUTPUT | ENABLE_CLOCK |
                                      SELECT_PT1) & COUNTING_MODE_16_BIT &
                                      CONTINOUS_OPERATING_MODE &
                                      DISABLE_PT_INT;
TIMER1_3_CNTRL_REG = timer1_3_cntrl_reg = (ENABLE_PT_OUTPUT | ENABLE_CLOCK) &
                                          COUNTING_MODE_16_BIT &
                                          CONTINOUS_OPERATING_MODE &
                                          DISABLE_PT_INT &
                                          ALL_TIMERS_OPERATIVE;
```

```
temp = square_wave_output(5000);
MSB1_BUFFER = (short) (temp / 256);
TIMER1_LATCH = (short) (temp % 256);

temp = square_wave_output(400000);
MSB2_BUFFER = (short) (temp / 256);
TIMER2_LATCH = (short) (temp % 256);
/*
 Initialize the programmable attenuators.
*/

PI_ATTEN = DI_ATTEN = 0;

IO_CONTROL = io_control |= (LOAD_PROXIMAL_ATTEN |
                            LOAD_DISTAL_ATTEN);
IO_CONTROL = io_control &= (DISABLE_PROXIMAL_ATTEN &
                            DISABLE_DISTAL_ATTEN);

/*
 MC6850 Asynchronous Communications Interface Adapter Initialization.
*/

ACIA1_CNTRL_STAT_REG = MASTER_RESET;
ACIA1_CNTRL_STAT_REG = (CLOCK_DIVIDE_RATIO_16 | B7_EVEN_1_STOP) &
                       (DISABLE_ACIA_RX_INT & DISABLE_ACIA_TX_INT);

ACIA2_CNTRL_STAT_REG = MASTER_RESET;
ACIA2_CNTRL_STAT_REG = (CLOCK_DIVIDE_RATIO_16 | B7_EVEN_1_STOP) &
                       (DISABLE_ACIA_RX_INT & DISABLE_ACIA_TX_INT);

/*
 MC68488 General Purpose Interface Adapter Initialization.
*/

INT_MASK_REG = DISABLE_GPIA_INT;

/*
 Initial values for the 12 position Programmable Switch.
*/

MAX_SYSTOLIC = 180;
MAX_DIASTOLIC = 100;
MAX_CUFF = 180;
MAX_MMHG = 20;
MAX_HEART = 180;

LEAD = AUTOMATIC_LEAD_SELECTION;

NULL = MODE_IS_STOP = YES;
REST_MODE_STATUS = FIRST_TIME = YES;

SELFTEST_OLD_STATE = REST_EXEC_OLD_STATE = MANUAL_OLD_STATE = 1;
LEAD_MONITORING = 1;

IN_CAL_CUFFP = IN_PUMP = IN_SECOND_DELAY = DATA_OK = NO;
PROCESSING_LEAD_SELECTION = STATUS_OF_LEAD_SELECTION_PROCESSING = NO;
MODE_IS_REST = MODE_IS_EXEC = MODE_IS_START = MODE_IS_MANUAL = NO;
MODE_IS_PROGRAM = MODE_IS_MODIFY = MODE_IS_HALT = MODE_IS_SELFTEST = NO;
PREVIOUS_ERROR_CONDITION = ALARM_ON = CLOCK_RUNNING = NO;
GOOD_REST_DATA = EXEC_WAS_PREVIOUS_MODE = FAILED_SELFTEST = NO;
LEAD_SELECTION_COMPLETE = DATASET_COMPLETE = ABORT2 = ABORT3 = NO;
SAMPLING_PI_DI = PROGRAMMED_MAX_CUFF = MODE_TRANSITION = NO;
BLEED_PROCESS_FINISHED = NO_ECG_FOUND = ERROR_CONDITION = NO;
PI_DI_AMP_AVG_COMPLETE = NO;
SHOW_TIME = YES;
```

```
SELECTION = MODE_IS_STANDBY = LEAD_PROGRESS = LEAD_STATUS = 0;
SECOND_BEST = TRIGGER_LEAD = LEADS_PROCESSED = 0;

SUM_PI_AMP = SUM_DI_AMP = 0.0;
for (temp = 0; temp < 10; temp++) {
   AVG_DI_ARRAY[temp] = 0.0;
   AVG_PI_ARRAY[temp] = 0.0;
}
PI_COUNT = DI_COUNT = 0:
LEAD1_SIGNAL_NOISE_RATIO = LEAD2_SIGNAL_NOISE_RATIO = 0.0;
LEAD3_SIGNAL_NOISE_RATIO = 0.0;

for (I = 0; I < 3; I++)
   LEAD1[I] = LEAD2[I] = LEAD3[I] = BAD[I] = 0;
I = 0;

SIZE = 2000;

/*
   Enable all interrupts.
*/
clear_sr(LEVEL0_INTERRUPT);

}
"C"
"68000"
$EXTENSIONS ON$
$FAR ON$
$CALL_ABS_LONG ON$
$LIB_ABS_LONG ON$
$ASM_FILE$
$INIT_ZEROES OFF$
$WARN OFF$
$ENTRY OFF$
#include "DEFINES"

extern int SWITCH_BUFFER,SYS_DISPLAY,SWITCH_LED,switch_led;
extern short DIAGNOSTIC_SELFTEST,FAILED_SELFTEST,
             MODE_IS_STOP,MODE_IS_REST,ecg_control,
             STATUS_OF_LEAD_SELECTION_PROCESSING,
             PROCESSING_LEAD_SELECTION;
extern unsigned short ECG_CONTROL;

/*********************/
/***************************     MAIN     *****************************/
                            /*********************/

/*
Routine Name         :   main
Parameters Passed    :   --
Parameters Returned  :   --
Calling Routines     :   start
Routines Called      :   standby_mode, initialize, selftest_mode,
                         display
Local Variables      :   --
*/ main()
  {

/*
   Look for special Diagnostic Self-test mode upon power-up.
  */

DIAGNOSTIC_SELFTEST = NO;
  if ((SWITCH_BUFFER & SELFTEST_DEPRESSED) == 0)
     DIAGNOSTIC_SELFTEST = YES;
```

```
/*
 Do initialization of all software/hardware devices.
*/ initialize();

/*
 Perform the self-tests.  Inform user of the STBPM status when not in
 the Diagnostic mode.  Place the unit in the STOP/REST mode of operation.
*/ if (!DIAGNOSTIC_SELFTEST)
     display(&SYS_DISPLAY,"TESTSELF ",8,-2,8);
  selftest_mode();
  if (FAILED_SELFTEST && !DIAGNOSTIC_SELFTEST)
     display(&SYS_DISPLAY,"FAIL ",4,-2,12);
  SWITCH_LED = switch_led |= (STOP_LED_ON | REST_LED_ON);
  MODE_IS_STOP = MODE_IS_REST = YES;

/*
 Allow lead selection to begin.
*/

STATUS_OF_LEAD_SELECTION_PROCESSING = PROCESSING_LEAD_SELECTION = YES;

/*
 Enable START/RUN and ECG interrupts.
*/

SWITCH_LED = switch_led &= DISABLE_SS_INT;
  ECG_CONTROL = ecg_control &= DISABLE_ECG_INT;
  ECG_CONTROL = ecg_control |= ENABLE_ECG_INT;

/*
 Go to the Standby mode until next power-up sequence.
*/ standby_mode();
}
"C"
"68000"
$EXTENSIONS ON$
$ASM_FILE$
$WARN OFF$
$FAR ON$
$CALL_ABS_LONG ON$
$LIB_ABS_LONG ON$
$INIT_ZEROES OFF$
#include "DEFINES"

extern unsigned int bleed_valve;
extern int SYS_DISPLAY,CUFFP_OFFSET,PUMP_UP,REG_A,REG_C,MAX_CUFF,
           BLEED_CRACK_POINT,BLEED_DOWN,LAST_CUFF_PRESSURE;
extern short MODE_IS_MANUAL,MODE_IS_MODIFY,FIRST_TIME,MODE_IS_START,
             BLEED_PROCESS_FINISHED,PREVIOUS_ERROR_CONDITION,DATA_OK,
             ERROR_CONDITION,DIAGNOSTIC_SELFTEST,FAILED_SELFTEST,
             INITIAL_BLEED;
extern unsigned short BLEED_VALVE;

/********************/
/************************   MANUAL MODE   ****************************/
                         /********************/

/*
 Routine Name         : manual_mode
 Parameters Passed    : -
 Parameters Returned  : -
```

```
Calling Routines      : standby_mode
Routines Called       : acquire_data, cal_cuffp, check_system, display
                        pump, stop
Local Variables       : in_normal_mode      -- flag to signal normal or
                                               diagnostic mode
                        selftest1_status    -- save status flag
                        selftest2_status    -- save status flag
                        avg_count           -- number of samples used to
                                               average the cuff pressure
                        cuff_pressure       -- current cuff pressure
                        total               -- register that holds total
                                               for cuff pressure average
                        count               -- count of samples taken
                                               for cuff pressure average
                        i                   -- loop control
*/ manual_mode()
{
/*
  Data declarations and initialization.
*/
   short in_normal_mode, selftest1_status,selftest2_status;
   int temp, avg_count, cuff_pressure, i;
   long total, count;

BLEED_PROCESS_FINISHED = NO;

/*
 Set up averaging loop counter.
*/
   avg_count = 50;

/*
 We are in normal mode if MODIFY key wasn't active.
*/
   in_normal_mode = MODE_IS_MANUAL && !MODE_IS_MODIFY;
   MODE_IS_MODIFY = NO;

/*
  If there was a previous error condition, re-initialize the display.
*/
   if (PREVIOUS_ERROR_CONDITION){
     PREVIOUS_ERROR_CONDITION = NO;
     display(&SYS_DISPLAY,"MAN. ",4,-2,12);
   }

/*
 Check power supplies.
*/ selftest1_status = DIAGNOSTIC_SELFTEST;
  selftest2_status = FAILED_SELFTEST;
  FAILED_SELFTEST = DIAGNOSTIC_SELFTEST = NO;
  check_system();
  DIAGNOSTIC_SELFTEST = selftest1_status;
  if (FAILED_SELFTEST){
    stop();
    ERROR_CONDITION = YES;
    FAILED_SELFTEST = selftest2_status;
    display(&SYS_DISPLAY,"VOLTCHECK",8,-2,8);
    return;
  }
  FAILED_SELFTEST = selftest2_status;

/*
   If this is first cycle in manual mode, then calibrate
   the pressure transducer.
```

```
*/
   if (FIRST_TIME)
      CUFFP_OFFSET = cal_cuffp();

/*
   Pump up the cuff to value specified.
*/
   PUMP_UP = MAX_CUFF / CUFFP_CONV;
   if (pump() == FAIL)
      return;

/*
   Execute this only if in the normal manual mode.
*/
   if (in_normal_mode) { if (FIRST_TIME) {
         FIRST_TIME = NO;
         INITIAL_BLEED = YES;
      }
/*
   Initialize the bleed valve.
*/
      else
         BLEED_VALVE = bleed_valve = BLEED_CRACK_POINT;

/*
   Set the dump valve opening
*/
      BLEED_DOWN = FORTY_mmHg;
   }

REG_A = PIR_500;

/*
   Start the loop; at half second intervals, adjust the bleed rate
   and display the current cuff pressure.
*/
   while (MODE_IS_START) { while ((REG_C & PF_MASK) == 0)
         ;
/*
   If this is normal mode, call the bleed adjustment routine.
*/
      if (in_normal_mode)
         bleed(0);

/*
   If this is the diagnostic mode, just find the current cuff pressure.
*/
      else {
         for (i = count = total = 0 ; i < avg_count; i++){
            if ((temp = acquire_data(CUFF_PRESSURE) - CUFFP_OFFSET) < 0)
               temp = 0;
            if (DATA_OK){
               total += temp;
               count++;
            }
         }
         if (count == 0)
            count = 1;
         LAST_CUFF_PRESSURE = total / count;
      }

/*
   In either mode, display the current cuff pressure.
*/
```

```
        cuff_pressure = (int)((double) LAST_CUFF_PRESSURE * CUFFP_CONV);
        display(&SYS_DISPLAY, "", 0, cuff_pressure, 2);

/*
   If the cuff pressure is less than 40 mmHg, open the dump and bleed valves
   and return to the standby mode.
*/
        if (in_normal_mode  &&  BLEED_PROCESS_FINISHED){
            stop();
            return;
        }
      }
   }
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

/*******************/
/************************       MEDIAN      ****************************/
                        /*******************/

/*
   Routine Name           : median
   Parameters Passed      : array, index, size
   Parameters Returned    : 'median value'
   Calling Routines       : process
   Routines Called        : -
   Local Variables        : change   -- flag to control bubble sort
                            tempa    -- temporary array for sorting values
                            temp     -- temporary register for bubble sort
                            i        -- loop control
*/

/* ******************************************************************** */
/*                                                                      */
/*   Median filter subroutine                                           */
/*                                                                      */
/* ******************************************************************** */
median(array, index, size)
int array[], index, size;
{
/*
   Define and initialize local variables.
*/
   char change = TRUE;
   int temp, tempa[10], i;

/*
   Load the temporary array from the passed array.
*/
   for (i = 0; i < size; i++)
      tempa[i] = array[index - i];

/*
   Bubble sort the temporary array.
*/
   while (change) {
      change = FALSE;
      for (i = 0; i < size - 1; i++) {
         if (tempa[i] > tempa[i + 1]) {
```

```
            temp = tempa[i];
            tempa[i] = tempa[i + 1];
            tempa[i + 1] = temp;
            change = TRUE;
         }
      }
   }
/*
   Choose the median element of the sorted temporary array.
*/
   return(tempa[size / 2]);
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$ long Zlongreal_round();

float cd1[100], cd2[100];
float m1[100], m2[100], b1[100], b2[100];
extern int xx, max_xx;

min_error(x_array,y_array,begin,end)
float x_array[],
      y_array[];
int begin,end;

{
  float sum_x_1,sum_y_1,sum_xy_1,sum_x2_1,sum_y2_1,
        sum_x_2,sum_y_2,sum_xy_2,sum_x2_2,sum_y2_2,
        slope1,y_int1,
        slope2,y_int2,
        new_slope1,new_y_int1,
        new_slope2,new_y_int2,
        sum_r2,max_r2,
        x,y,SSxy,r2_1,r2_2,temp;
  int   index,length1,length2,i,j;

sum_x_1 = sum_y_1 = sum_xy_1 = sum_x2_1 = sum_y2_1 = 0;
  sum_x_2 = sum_y_2 = sum_xy_2 = sum_x2_2 = sum_y2_2 = 0;

if ((end - begin) < 6)
    return(10);

/*
   Initialize the first array summing values
*/
  for (index = begin, j=0; index - begin < 3; index++, j++){
    sum_x_1 += x = x_array[index];
    sum_y_1 += y = y_array[index];
    sum_xy_1 += x * y;
    sum_x2_1 += x * x;
    sum_y2_1 += y * y;
  }
  length1 = j;

/*
   Initialize the second array summing values
*/
  for (i = index, j = 0; i < end; i++, j++){
    sum_x_2 += x = x_array[i];
```

```
        sum_y_2 += y = y_array[i];
        sum_xy_2 += x * y;
        sum_x2_2 += x * x;
        sum_y2_2 += y * y;
    }
    length2 = j;
/*
    Initialize the slope, y-intercept, and coefficient-of-determination
        values for both arrays
*/
    new_slope1 = (SSxy = sum_xy_1 - (sum_x_1 * sum_y_1) / length1) /
            (sum_x2_1 - (sum_x_1 * sum_x_1) / length1);
    new_y_int1 = (sum_y_1 / length1) - new_slope1 * (sum_x_1 / length1);
    r2_1 = (new_slope1 * SSxy) / (sum_y2_1 - (sum_y_1 * sum_y_1) / length1);

new_slope2 = (SSxy = sum_xy_2 - (sum_x_2 * sum_y_2) / length2) /
            (sum_x2_2 - (sum_x_2 * sum_x_2) / length2);
    new_y_int2 = (sum_y_2 / length2) - new_slope2 * (sum_x_2 / length2);
    r2_2 = (new_slope2 * SSxy) / (sum_y2_2 - (sum_y_2 * sum_y_2) / length2);

max_r2 = r2_1 + r2_2;

while (length2 > 3){
/*
    Remove the sums of point 'x' from 2nd array and add them to the 1st
*/
        sum_x_1 += x = x_array[index];
        sum_x_2 -= x;
        sum_y_1 += y = y_array[index];
        sum_y_2 -= y;

sum_xy_1 += x * y;
        sum_xy_2 -= x * y;
        sum_x2_1 += x * x;
        sum_x2_2 -= x * x;
        sum_y2_1 += y * y;
        sum_y2_2 -= y * y;

/*
    Increment 1st array and decrement 2nd array
*/
        length1++;
        length2--;

/*
    Calculate new slope, y-intercept, and c. d. values for both arrays
*/
        slope1 = (SSxy = sum_xy_1 - (sum_x_1 * sum_y_1) / length1) /
                (sum_x2_1 - (sum_x_1 * sum_x_1) / length1);
        y_int1 = (sum_y_1 / length1) - slope1 * (sum_x_1 / length1);
        r2_1 = (slope1 * SSxy) / (sum_y2_1 - (sum_y_1 * sum_y_1) / length1);

slope2 = (SSxy = sum_xy_2 - (sum_x_2 * sum_y_2) / length2) /
                (sum_x2_2 - (sum_x_2 * sum_x_2) / length2);
        y_int2 = (sum_y_2 / length2) - slope2 * (sum_x_2 / length2);
        r2_2 = (slope2 * SSxy) / (sum_y2_2 - (sum_y_2 * sum_y_2) / length2);

sum_r2 = r2_1 + r2_2;

m1[xx] = slope1; m2[xx] = slope2;
        b1[xx] = y_int1; b2[xx] = y_int2;
        cd1[xx] = r2_1; cd2[xx++] = r2_2;
/*
    If the new sum of c. d.'s is greater than the previous greatest,
        then save the slopes and y-intercepts for these lines
*/
        if (sum_r2 > max_r2){
```

```
      max_r2 = sum_r2;
      new_slope1 = slope1;
      new_y_int1 = y_int1;
      new_slope2 = slope2;
      new_y_int2 = y_int2;
      max_xx = xx;
    )
    index++;
  )
  if ((new_slope1 - new_slope2) == 0)
    return(11);

m1[xx] = 0; m2[xx] = 0; b1[xx] = 0; b2[xx] = 0; cd1[xx] = 0; cd2[xx++] = 0;
/*
  Return the x-value of the point of intersection of the 2 lines whose
    sum of coefficients-of-determination are greatest
*/
  return(Zlongreal_round((new_y_int2 - new_y_int1) / (new_slope1 - new_slope2)));
)
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int SIZE,REG_A,REG_B,SECOND,ECG_STATUS_BUFFER;
extern unsigned int RAW_DATA_POSITION;
extern short ecg_control,DELAY,DELAY_TIME;
extern unsigned short ECG_CONTROL;

/*******************/
/*************************   MONITOR LEAD   ****************************/
                        /*******************/

/*
  Routine Name        : monitor_lead
  Parameters Passed   : lead_selection -- lead to be monitored
                        new_lead -- flag signaling different lead to be
                                      monitored
  Parameters Returned : progress code:
                          0 -- continue processing on current lead
                          1 -- finished processing on current lead
  Calling Routines    : select_lead
  Routines Called     : set_sr
  Local Variables     : pulse_detected -- signals when an ECG trigger
                                            has occurred
                        first_trigger -- signals first ECG trigger
                        time -- time in seconds spent monitoring
                                  current lead
                        temp -- temporary storage
                        old_time -- time in seconds when current
                                      lead monitoring started
                        before_trigger -- data acquisition index
                                            position when the first ECG
                                            trigger is detected
                        after_trigger -- data acquisition index
                                            position after the first ECG
                                            trigger is detected

*/ monitor_lead(lead_selection,new_lead)
short lead_selection,*new_lead;
```

```c
{static short pulse_detected, first_trigger;
 static int time,temp,old_time,before_trigger,after_trigger;

/*
 Select the new lead to be monitored and activate a two millisecond
 data acquisition of the raw ECG lead amplitudes.  Mask the microprocessor
 SR to level four to disable the servicing of ECG interrupts.  The ECG
 interrupt pending flag will be monitored.
*/ if (!*new_lead){
    ECG_CONTROL = ecg_control &= CLEAR_LEAD_SELECTION;
    ECG_CONTROL = ecg_control |= lead_selection;
    set_sr (LEVEL4_INTERRUPT);
    ECG_CONTROL = ecg_control &= DISABLE_ECG_INT;
    ECG_CONTROL = ecg_control |= ENABLE_ECG_INT;
    RAW_DATA_POSITION = 0;
    SIZE = 2000;
    DELAY = YES;
    DELAY_TIME = 0;
    REG_A = PIR_02;
    REG_B |= ENABLE_PIE;
    before_trigger = after_trigger = pulse_detected = NO;
    first_trigger = YES;
    *new_lead = YES;

/*
 Record a starting time.
*/ while (REG_A & UPDATE_CYCLE_IN_PROGRESS)
      ;
    old_time = SECOND & LOW_BYTE_MASK;
    return(0);
  }

/*
 Delay 50 milliseconds if a different lead was selected.  This allows the
 ECG trigger circuitry to stabilize before starting data acquisition.
*/ if (DELAY)
    return(0);

/*
 Record a new time.
*/ while (REG_A & UPDATE_CYCLE_IN_PROGRESS)
    ;
  if ((time = (SECOND & LOW_BYTE_MASK) - old_time) < 0)
    time += 60;

/*
 Check the interrupt status.  Store the current position of the data
 acquisition pointer if the first ECG trigger has occurred.
*/ if (!(ECG_STATUS_BUFFER & ECG_INTERRUPT_PENDING)){
    ECG_CONTROL = ecg_control &= DISABLE_ECG_INT;
    ECG_CONTROL = ecg_control |= ENABLE_ECG_INT;
    pulse_detected = YES;
    if (first_trigger){
      first_trigger = NO;
      before_trigger = RAW_DATA_POSITION;
      return(0);
    }
  }
```

```
}
/*
There must be at least 50 samples taken after the trigger pulse and a
total of at least 500 samples taken during the first second of lead
monitoring.  Collect two seconds of data when no ECG trigger is seen.
*/ after_trigger = RAW_DATA_POSITION;
 if (pulse_detected && ((after_trigger < 500) ||
    (after_trigger - before_trigger < 50)))
   return(0);
 else if (pulse_detected == NO && time < 2)
    return(0);
 return(1);
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include"DEFINES"

extern unsigned long CURRENT_INT_TIME,PREVIOUS_INT_TIME;

extern unsigned int RAW_DATA_POSITION, bleed_valve;

extern int ELAPSED_TIME,SYS_DISPLAY,REG_A,HR_ALARM,MIN_ALARM,SEC_ALARM,
          REG_B,MAX_CUFF,PI_ATTEN,DI_ATTEN,IO_CONTROL.io_control,
          CUFFP_OFFSET,TRIGGER_LEAD,SIZE,ECG[],ALARM_LED,alarm_led,
          PRP_DISPLAY,INTERVAL_MIN,INTERVAL_END,DIA_DISPLAY,
          SYSTOLIC,DIASTOLIC,PUMP_UP,BLEED_DOWN,
          SAMPLE_INDEX,SAMPLE_TIME,BLEED_CRACK_POINT;

extern short MODE_TRANSITION,ELAPSED_MIN1,ELAPSED_MIN2,DIAGNOSTIC_SELFTEST,
          ELAPSED_SEC1,ELAPSED_SEC2,MODE_IS_REST,FAILED_SELFTEST,
          INTERVAL_UP,MODE_IS_START,LEAD_SELECTION_COMPLETE,ecg_control,
          ABORT3,AVERAGE_HR_DISPLAYED,PROCESSING_LEAD_SELECTION,
          MEASUREMENT_COMPLETE,BLEED_PROCESS_FINISHED,MODE_IS_EXEC,
          FIRST_TIME,FIRST_ECG,STATUS_OF_LEAD_SELECTION_PROCESSING,
          LEAD_STATUS,LEAD_MONITORING,LEAD_PROGRESS,LEAD1[],LEAD2[],
          LEAD3[],BAD[],LEADS_PROCESSED,CLOCK_RUNNING,ERROR_CONDITION,
          ABORT2,INITIAL_BLEED,PREVIOUS_ERROR_CONDITION,NO_ECG_FOUND,
          SAMPLING_PI_DI,PROGRAMMED_MAX_CUFF,DATASET_COMPLETE,
          SHOW_TIME;

extern unsigned short HR_SWITCH,ECG_CONTROL,BLEED_VALVE,INTERVAL_SEC;

extern int HR_DISPLAY;

/********************/
/************************   PREPROCESS   ***************************/
                       /********************/

/*
  Routine Name         : preprocess
  Parameters Passed    : --
  Parameters Returned  : --
  Calling Routines     : standby_mode
  Routines Called      : display, check_system, stop, abort3, clear_sr
                         pump, process, add_time, select_lead, cal_cuffp
  Local Variables      : temp -- temporary storage
```

```
                          selftest1_status -- Diagnostic Self-test status
                          selftest2_status -- Non-diagnostic Self-test status
                          old_trigger_lead -- previous lead selected
                          min -- interval time minute value
                          sec -- interval time second value
                          ret_code -- saves the return code of "process"
*/ preprocess()
{int ret_code, temp;
 static short selftest1_status,selftest2_status,old_trigger_lead;
 short min,sec;

/*
 Calibrate the pressure transducer.
*/

CUFFP_OFFSET = cal_cuffp();

/*
 Set displays for first measurement cycle of Rest or Exercise modes.
*/ if (MODE_TRANSITION || PREVIOUS_ERROR_CONDITION){
      MODE_TRANSITION = PREVIOUS_ERROR_CONDITION = NO;
      ELAPSED_TIME = ELAPSED_MIN1 = ELAPSED_MIN2 = 0;
      ELAPSED_SEC1 = ELAPSED_SEC2 = 0;
      if (HR_SWITCH & HR_SWITCH_ON)
         display (&SYS_DISPLAY,"  0   0   0 0.0 0:00",17,-1,0);
      else
         display (&SYS_DISPLAY,"  0   0     0.0 0:00",17,-1,0);

/*
 Set a don't care code in all alarm bytes of the Real-Time Clock
 for the one second ELAPSED TIME display update and enable alarm
 interrupts.
*/ while (REG_A & UPDATE_CYCLE_IN_PROGRESS)
         ;
      HR_ALARM = MIN_ALARM = SEC_ALARM = RTC_DONT_CARE_CODE;
      REG_B |= ENABLE_AIE;
      CLOCK_RUNNING = YES;

/*
 The initial Rest or Exercise cycle bleed and pump up values are
 as follows:

Mode    |  Bleed                          Pump Up
     ------------------------------------------------------------
     Rest    | 40 mmHg                         Operator programmed value
     Exercise| Previous diastolic - 30 mmHg    Previous systolic + 50 mmHg Set Proximal and Distal attenuators to 0.0 dB in the initial Rest Mode
 cycle.
*/ if (MODE_IS_REST){
         PUMP_UP = MAX_CUFF / CUFFP_CONV;
         BLEED_DOWN = FORTY_mmHg;
         PI_ATTEN = DI_ATTEN = 0;
         IO_CONTROL = io_control &= SET_ATTEN_0db;
         IO_CONTROL = io_control |= (LOAD_PROXIMAL_ATTEN |
                                     LOAD_DISTAL_ATTEN);
         IO_CONTROL = io_control &= (DISABLE_PROXIMAL_ATTEN &
                                     DISABLE_DISTAL_ATTEN);
      }
```

```
    else
      if (PROGRAMMED_MAX_CUFF){
        PROGRAMMED_MAX_CUFF = NO;
        PUMP_UP = MAX_CUFF / CUFFP_CONV;
      }
      else {
        PUMP_UP = (SYSTOLIC + 50) / CUFFP_CONV;
        BLEED_DOWN = (DIASTOLIC - 30) / CUFFP_CONV;
      }
  }

/*
Check the STBPM power supplies.  Display an error message to the
operator if the supplies are bad and return to the Standby mode.
*/ selftest1_status = DIAGNOSTIC_SELFTEST;
  selftest2_status = FAILED_SELFTEST;
  FAILED_SELFTEST = DIAGNOSTIC_SELFTEST = NO;
  check_system();
  DIAGNOSTIC_SELFTEST = selftest1_status;
  if (FAILED_SELFTEST){
    stop();
    REG_B &= DISABLE_AIE;
    CLOCK_RUNNING = NO;
    ERROR_CONDITION = YES;
    FAILED_SELFTEST = selftest2_status;
    display(&SYS_DISPLAY,"   0   0   0VOLTCHECK",17,-2,8);
    return;
  }
  FAILED_SELFTEST = selftest2_status;

/*
Initialize variables.
*/

INTERVAL_UP = YES;

/*
Take blood pressures while the measurement cycle is not stopped by
the operator.
*/ while (MODE_IS_START){

/*
For every measurement cycle, do the following:
*/ while (INTERVAL_UP || ABORT2){

/*
  Re-enable display of elapsed time if it had been disabled by an
    insufficient pump-up error.
*/
      SHOW_TIME = YES;

/*
  Select the trigger lead and show the operator the current lead status
  at the DIASTOLIC display.  Do "abort3" processing if the trigger lead
  is not satisfactory.
*/ if (TRIGGER_LEAD == BAD_LEAD){
        TRIGGER_LEAD = old_trigger_lead;
        ABORT3 = YES;
```

```
      if (abort3() == FAIL)
         return;
      else if (!LEAD_SELECTION_COMPLETE)
          TRIGGER_LEAD = old_trigger_lead;
      ECG_CONTROL = ecg_control &= CLEAR_LEAD_SELECTION;
      ECG_CONTROL = ecg_control |= TRIGGER_LEAD;
      switch (TRIGGER_LEAD){
         case ECG_LEAD1 :   display(&DIA_DISPLAY," L1",2,-1,0);
                            break;
         case ECG_LEAD2 :   display(&DIA_DISPLAY," L2",2,-1,0);
                            break;
         case ECG_LEAD3 :   display(&DIA_DISPLAY," L3",2,-1,0);
                            break;
      }

/*
 Initialize variables, close bleed valve, clear alarm LED's, and
 clear the microprocessor SR.
*/ clear_sr(LEVEL0_INTERRUPT);

SIZE = 2000;

for (temp = 0; temp < SIZE; temp++)
         ECG[temp] = 0;

AVERAGE_HR_DISPLAYED = INTERVAL_UP = NO_ECG_FOUND =
      PROCESSING_LEAD_SELECTION = ABORT2 = DATASET_COMPLETE =
      MEASUREMENT_COMPLETE = BLEED_PROCESS_FINISHED =
      SAMPLING_PI_DI = NO;

CURRENT_INT_TIME = PREVIOUS_INT_TIME = RAW_DATA_POSITION = 0;

FIRST_ECG = YES;

BLEED_VALVE = bleed_valve |= BLEED_VALVE_CLOSED;
      ALARM_LED = alarm_led &= ALARM_LEDS_OFF;

/*
 Read the INTERVAL TIME setting and calculate the end of the current
 measurement cycle.  Minimal interval times are 50 seconds in the
 Rest mode and 30 seconds in the Exercise mode.
*/ min = (((~INTERVAL_MIN) & LOW_BIT_MASK) * 10) +
            (((~INTERVAL_MIN) & HIGH_BIT_MASK) >> 4);
      sec = ((~INTERVAL_SEC) & LOW_BIT_MASK) * 10;
      if (MODE_IS_EXEC && (min == 0 && sec < 30))
         INTERVAL_END = add_time(ELAPSED_TIME,30);
      else if (MODE_IS_REST && (min == 0 && sec < 50))
         INTERVAL_END = add_time(ELAPSED_TIME,50);
      else
         INTERVAL_END = add_time(ELAPSED_TIME,(min * 100 + sec));

/*
 Test for pump up limits of 100 - 300 mmHg.
*/ if (PUMP_UP < (temp = CUFMIN / CUFFP_CONV))
         PUMP_UP = temp;
      else if (PUMP_UP > (temp = CUFMAX / CUFFP_CONV))
         PUMP_UP = temp;
```

```
/*
Disable the 2 millisecond data acquisition and ECG interrupts while
pumping up the cuff.
*/

REG_B &= DISABLE_PIE;
     ECG_CONTROL = ecg_control &= DISABLE_ECG_INT;

/*
Return to the Standby mode if bad pump up results occur; otherwise
continue. Set displays to standard values before pumping.
*/
     display(&SYS_DISPLAY,"   0", 2, -1, 0);
     display(&HR_DISPLAY,"  0 0.0     ", 11, -1, 0);

if (pump() == FAIL) {
        display(&SYS_DISPLAY,"",0,0,2);
        display(&DIA_DISPLAY,"",0,0,2);
        return;
     }

/*
A bleed valve crack point is established on the first REST measurement cycle
to help start the bleed process.  Assign this starting bleed valve opening
to measurement cycles thereafter.
*/ if (FIRST_TIME && MODE_IS_REST)
        INITIAL_BLEED = YES;
     else
        BLEED_VALVE = bleed_valve = BLEED_CRACK_POINT;

/*
Allow ECG interrupts to occur.  Process the results as the data becomes
available.
*/

REG_A = PIR_02;
     REG_B |= ENABLE_PIE;
     ECG_CONTROL = ecg_control &= DISABLE_ECG_INT;
     ECG_CONTROL = ecg_control |= ENABLE_ECG_INT;

/*
  Call "process" and check for an error on the return.
*/
     ret_code = process();

switch (ret_code) {

/*
  Return code of '0'; normal return so no action taken.
*/
        case 0 :
           break;

/*
  General purpose error return activities.
*/
        case 1 :
           display(&SYS_DISPLAY,"",0,0,2);
           display(&DIA_DISPLAY,"",0,0,2);
           display(&HR_DISPLAY,"",0,0,2);
           return;

/*
```

```
  ABORT2 error return; don't clear displays or return to STANDBY.
*/
        case 2 :
            break;

/*
  Insufficient pump-up error: set interval end time 10 seconds hence
  and disable the displaying of elapsed time.
*/
        case 3 :
            display(&SYS_DISPLAY,"",0,0,2);
            display(&DIA_DISPLAY,"",0,0,2);
            display(&HR_DISPLAY,"",0,0,2);
            SHOW_TIME = NO;
            INTERVAL_END = add_time(ELAPSED_TIME, 10);
            break;
        } if (ret_code == 0)
            output_data_rs232();

/*
Enable sampling of the proximal and distal channels to get individual
average amplitudes.  Do not do this if "abort2" processing has been
activated.
*/ if (!ABORT2){
          SAMPLE_TIME = SAMPLE_INDEX = 0;
          SAMPLING_PI_DI = YES;
        }

/*
  A mandatory 10 second period of rest after the bleed process is
  finished is issued before starting the next measurement cycle in
  either the Rest or Execise modes.
*/ if (BLEED_PROCESS_FINISHED && !ABORT2){
          if ((temp = add_time(ELAPSED_TIME,10)) > INTERVAL_END)
            INTERVAL_END = temp;
        }
        MEASUREMENT_COMPLETE = YES;
        FIRST_TIME = NO;
        old_trigger_lead = TRIGGER_LEAD;

/*
  If the return code from "process" was a 3 (insufficient pump-up)
  then don't disable the ECG interrupts.
*/
        if (ret_code != 3) {
            ECG_CONTROL = ecg_control &= (FLOAT_RESET_LOW & DISABLE_ECG_INT);
            ECG_CONTROL = ecg_control |= FLOAT_RESET_HIGH;
        }
    }

/*
Do ECG lead selection only if in the automatic lead selection mode
and the bleed process is finished.
*/
    if ((STATUS_OF_LEAD_SELECTION_PROCESSING == YES)
         && BLEED_PROCESS_FINISHED && !ABORT2){
      for (temp = 0; temp < 3; temp++)
        LEAD1[temp] = LEAD2[temp] = LEAD3[temp] = BAD[temp] = 0;
      LEAD_SELECTION_COMPLETE = NO;
      LEAD_STATUS = LEAD_PROGRESS = LEADS_PROCESSED = 0;
```

```
      LEAD_MONITORING = 1;
      PROCESSING_LEAD_SELECTION = YES;
      while (!INTERVAL_UP && MODE_IS_START)

select_lead(&LEAD_PROGRESS,&LEAD_MONITORING,&LEAD_STATUS);
   }
 }
 PROCESSING_LEAD_SELECTION = NO;
}
"C"
"68000"
$EXTENSIONS ON$
$FAR ON$
$WARN OFF$
$INIT_ZEROES OFF$
$CALL_ABS_LONG ON$
$LIB_ABS_LONG ON$
$ASM_FILE ON$
#include "DEFINES"

extern long Zlongreal_round();
extern double SQRT();

extern float AVG_PI_AMP, AVG_DI_AMP;

extern unsigned long CURRENT_INT_TIME,HR_COUNT;

extern int SYSTOLIC,DIASTOLIC,DI_ATTEN,PI_ATTEN,ECG[],CUFF[],PRP_DISPLAY,
          MAX_POSITION,MAX_AMPLITUDE,SYS_DISPLAY,DIA_DISPLAY,HR_DISPLAY,
          MAX_SYSTOLIC,MAX_DIASTOLIC,MAX_HEART,PROX[],DIST[],SIZE,
          BLEED_DOWN,PUMP_UP,IO_CONTROL,io_control,ALARM_LED,alarm_led,
          REG_A,REG_B,HEART_RATE,MAX_MMHG;

extern unsigned int RAW_DATA_POSITION,bleed_valve;

extern short DATASET_COMPLETE,MODE_IS_REST,MODE_IS_EXEC,FIRST_TIME,
          MODE_IS_STOP,BLEED_PROCESS_FINISHED,INTERVAL_UP,
          GOOD_REST_DATA,ALARM_ON,FIRST_ECG,NO_ECG_FOUND,
          AVERAGE_HR_DISPLAYED,ABORT2,ecg_control,
          ERROR_CONDITION,CLOCK_RUNNING,ARRHYTHMIA;

extern unsigned short HR_SWITCH,ECG_CONTROL,BLEED_VALVE;

extern float t_values[30];

#define T_SIZE 30
                         /*********************/
/***************************     PROCESS     ***************************/
                         /*********************/

/*
 * Routine Name          : process
 * Parameters Passed     : -
 * Parameters Returned   : -
 * Calling Routines      : preprocess
 * Routines Called       : display, find_max, median, pump, second_delay
 * Local Variables       :
 */

/*
 *   Declare the variables
 */
    char still_working, ecg_not_found, not_a_repeat, re_pump,
         first_time, acceptable_pulse, prp[4];
    int last_sys, last_dia,
        sys_check, dia_check,
        current_cuffp, last_cuffp,
```

```
      dump_pressure, error, pulses_since_pump,
      current_prox_max, current_dist_max,
      avg_prox_amplitude, avg_dist_amplitude,
      lo_prox_cnt, lo_dist_cnt, hi_dist_cnt, repump_cnt,
      max_prox, max_dist, pulses, width, length,
      sys_index, dia_index,
      dist_peak_level, dist_peak_index, dist_threshold,
      dxd_peak_level, dxd_peak_index, dxd_threshold,
      i, j, k, m, n;
  int open_dist_window, open_prox_window,
      dist_window_length, prox_window_length,
      dist_lag, prox_lag, earliest_prox, earliest_dist;
  int provisional_sys, provisional_dia, pi_atten, di_atten;
  int estimated_sys, estimated_dia,
      est_sys_index, est_dia_index;
  unsigned int ecg_ptr, last_ecg, last_prox;
  float ftemp;
  double x, y, sum_x, sum_y, sum_xy, sum_x2, sum_y2,
         SSx, SSy, SSxy, dtemp,
         sd, slope, y_int, mean_x, mean_y,
         expected_value, prediction_interval, prediction_range, z;
  int prp_value, ind_array[25];
  unsigned int avg_ecg_to_prox, avg_etp_5, max_prox_to_dist;
  int prox_max[MAX_PULSES], prox_to_dist[MAX_PULSES],
      dist_max[MAX_PULSES], cuff_pressure[MAX_PULSES],
      ecg_to_prox[MAX_PULSES], dist_med[MAX_PULSES],
      dist_X_delay[MAX_PULSES], dxd_med[MAX_PULSES],
      dist_exp[MAX_PULSES], dxd_exp[MAX_PULSES],
      dist_med_exp[MAX_PULSES], dxd_med_exp[MAX_PULSES],
      ecg_to_dist[MAX_PULSES], cuffp_raw[MAX_PULSES];

int sys_index1, dia_index1,
       estimated_sys1, estimated_dia1, est_sys_index1, est_dia_index1,
       dist_peak_lvl1, dist_peak_ind1;

int SYS_AMP, DIA_AMP, SYS_PROD, DIA_PROD,
       ERROR_PROD, ERROR_AMP;

process()
{
long temp;
int multiplier;
/*
 * The enabling of the 2 ms. data acquisition interrupt at this
 * point in the program is an attempt to fix a probable software
 * error that causes the 2 ms. interrupt to become disabled
 * inadvertantly.
 */
   REG_B &= DISABLE_PIE;
   REG_A = PIR_02;
   REG_B |= ENABLE_PIE;

/*
 *   Initialization
 */
   dist_peak_level = 0;
   still_working = TRUE;
   ecg_not_found = TRUE;
   re_pump = FALSE;
   DATASET_COMPLETE = FALSE;
   max_prox = max_dist = 0;
   ecg_ptr = pulses = m = n = k = 0;
   sum_x2 = sum_y2 = sum_xy = sum_x = sum_y = dtemp = x = y = 0;
   expected_value = prediction_interval = prediction_range = 0;
   pulses_since_pump = repump_cnt = 0;
   lo_prox_cnt = lo_dist_cnt = hi_dist_cnt = 0;
   avg_prox_amplitude = (int) AVG_PI_AMP;
```

```
   avg_dist_amplitude = (int) AVG_DI_AMP;
   width = 5;
   earliest_prox = 25 / SAMPLE_INTERVAL;
   earliest_dist = -50 / SAMPLE_INTERVAL;
   pi_atten = PI_ATTEN; di_atten = DI_ATTEN;
   last_cuffp = (int)(PUMP_UP * CUFFP_CONV);
   dump_pressure = (int)(BLEED_DOWN * CUFFP_CONV);

/*
 * If it is the first cycle in the REST mode, initialize the window
 *   opening points and the window sizes.
 */
   if (MODE_IS_REST && FIRST_TIME) {
      prox_window_length = 250 / SAMPLE_INTERVAL;
      open_prox_window = earliest_prox;
      dist_window_length = 225 / SAMPLE_INTERVAL;
      open_dist_window = earliest_dist;
      last_sys = last_dia = 0;
      dist_peak_level = 0;
   }

/*
 * If it isn't the first time in a mode, set the pulse validity check
 *   envelope limits. Use previous systolic minus 5 or 1/10 of the
 *   difference between previous systolic and diastolic, which ever
 *   is greater. Same logic but add for diastolic check.
 */
   if (!FIRST_TIME) {
      first_time = FALSE;
      if (((temp = last_sys - last_dia) / 10) > 5) {
         sys_check = last_sys - temp;
         dia_check = last_dia + temp;
      }
      else {
         sys_check = last_sys - 5;
         dia_check = last_dia + 5;
      }
   }
   else {
      first_time = TRUE;
      acceptable_pulse = TRUE;
   }

/*
 * Initialize the noise level multiplier value for the current mode.
 */
   if (MODE_IS_REST)
      multiplier = 4;
   else
      multiplier = 8;

$PAGE$
/* Start the loop */
   while (still_working && pulses < 100) {

/* ********************************************************************** */
/*                                                                        */
/*   Raw data processing                                                  */
/*                                                                        */
/* ********************************************************************** */

/*
 * Wait for an ECG but don't get ahead of RAW_DATA_POSITION.
 *  Check the flags for an immediate exit.
 */
      while (ecg_not_found) {
```

```
            if (ecg_ptr < RAW_DATA_POSITION) {
                if (ECG[ecg_ptr % SIZE] == ECG_THRESHOLD) {
                    last_ecg = ecg_ptr;
                    ecg_not_found = FALSE;
                    ECG[ecg_ptr % SIZE] = 0;
                }
                ecg_ptr++;
            }
            if (MODE_IS_STOP)
                return(1);
            if (ABORT2)
                return(2);
            if (BLEED_PROCESS_FINISHED || INTERVAL_UP) {
                still_working = FALSE;
                break;
            }
        }
        ecg_not_found = TRUE;

/*
 * Check external flags for immediate exit if necessary.
 *  If the dump valve has been opened, exit immediately.
 */
        if (MODE_IS_STOP)
            return(1);
        if (ABORT2)
            return(2);
        if (BLEED_PROCESS_FINISHED || INTERVAL_UP) {
            still_working = FALSE;
            break;
        }

/*
 *  Adjust the opening of the proximal window.
 */
        if (pulses == 5) {
            for (i = 0, temp = 0; i < pulses; i++)
                temp += ecg_to_prox[i];
            avg_etp_5 = temp / i;
            if (avg_etp_5 > 500 / (SAMPLE_INTERVAL))
                avg_etp_5 = 500 / SAMPLE_INTERVAL;
            open_prox_window = earliest_prox;
            prox_window_length = (avg_etp_5 + (100 / SAMPLE_INTERVAL)) -
                    open_prox_window;
        }

/*
 * Find the maximum proximal amplitude and the delay between
 *  ECG and proximal peak. Update proximal peak maximum if necessary.
 */
        find_max(PROX, last_ecg, open_prox_window, prox_window_length);
        prox_max[pulses] = current_prox_max = MAX_AMPLITUDE;
        if (MAX_AMPLITUDE > max_prox)
            max_prox = MAX_AMPLITUDE;
        if (pulses < 5)
            last_prox = MAX_POSITION;
        else
            last_prox = last_ecg + avg_etp_5;
        ecg_to_prox[pulses] = MAX_POSITION - last_ecg;
/*
 * Find the maximum distal amplitude and delay between
 *  proximal peak and distal peak. Update the distal peak maximum
 *   if necessary.
 */
        find_max(DIST, last_prox, open_dist_window, dist_window_length);
        prox_to_dist[pulses] = MAX_POSITION - last_prox;
        ecg_to_dist[pulses] = MAX_POSITION - last_ecg;
```

```
        dist_max[pulses] = current_dist_max = MAX_AMPLITUDE;
        if (MAX_AMPLITUDE > max_dist)
            max_dist = MAX_AMPLITUDE;

/*
 * Calculate the cuff pressure average for this pulse.
 */
        i = last_prox + open_dist_window; j = 0; temp = 0;
        while (i < RAW_DATA_POSITION  &&  j < 50) {
            temp += CUFF[i % SIZE];
            i++; j++;
        }
        if (j) {
            current_cuffp = cuff_pressure[pulses] = (temp / j) * CUFFP_CONV;
            cuffp_raw[pulses] = current_cuffp;
        }

/*
 * Display the current cuff pressure if its lower or if there was a
 * re-pump.
 */
        if (re_pump  ||  current_cuffp < last_cuffp) {
            re_pump = FALSE;
            display(&SYS_DISPLAY,"",0,current_cuffp,2);
        }

/*
 *  Check the pulse amplitude for validity. If the pulse is more than
 *  4 times the noise level, accept it. If it is outside the previous
 *  systolic-diastolic envelope, accept it. Otherwise, if the arrhythmia
 *  flag is set, ignore the pulse. If it is not set, replace the pulse
 *  with the average of the previous 3 pulses.
 */
        if (!first_time && (current_dist_max < avg_dist_amplitude * 4)) { if (current_cuffp < sys_check && current_cuffp > dia_check) { if (ARRHYTHMIA)
                    acceptable_pulse = FALSE;
                else {
                    acceptable_pulse = TRUE;
                    if (pulses >= 3) {
                        dist_max[pulses] = current_dist_max =
                            (dist_max[pulses - 1] +
                             dist_max[pulses - 2] +
                             dist_max[pulses-3]) / 3;
                    }
                }
            }
            else
                acceptable_pulse = TRUE;
        }
        else
            acceptable_pulse = TRUE;
$PAGE$
/* ******************************************************************* */
/*                                                                     */
/*    Peak data processing                                             */
/*                                                                     */
/* ******************************************************************* */

/*
 * Perform the real-time ordering of the data points.
 *  If cuff pressure is less than previous then no action is necessary.
 *  If cuff pressure is the same as previous then ignore it.
 *  If cuff pressure is greater than previous then put it in proper place.
 */
```

```
        if (acceptable_pulse) { if (cuff_pressure[pulses] < cuff_pressure[pulses - 1])
                pulses++;
            else if (cuff_pressure[pulses] > cuff_pressure[pulses - 1]) {
                i = pulses;
                not_a_repeat = TRUE;
                while (cuff_pressure[pulses] >= cuff_pressure[i - 1]  &&  i > 0) {
                    if (cuff_pressure[pulses] == cuff_pressure[i - 1])
                        not_a_repeat = FALSE;
                    i--;
                } if (not_a_repeat) {
                    i = pulses;
                    while (cuff_pressure[i] > cuff_pressure[i - 1]  &&  i > 0) {

/*
 * Re-order the cuff pressure.
 */
                        temp = cuff_pressure[i];
                        cuff_pressure[i] = cuff_pressure[i - 1];
                        cuff_pressure[i - 1] = temp;

/*
 * Re-order the distal amplitude.
 */
                        temp = dist_max[i];
                        dist_max[i] = dist_max[i - 1];
                        dist_max[i - 1] = temp;

/*
 * Re-order the proximal amplitude.
 */
                        temp = prox_max[i];
                        prox_max[i] = prox_max[i - 1];
                        prox_max[i - 1] = temp;

/*
 * Re-order the proximal to distal delay.
 */
                        temp = prox_to_dist[i];
                        prox_to_dist[i] = prox_to_dist[i - 1];
                        prox_to_dist[i - 1] = temp;

/*
 * Re-order the ecg to proximal delay.
 */
                        temp = ecg_to_prox[i];
                        ecg_to_prox[i] = ecg_to_prox[i - 1];
                        ecg_to_prox[i - 1] = temp;

/*
 * Re-order the ecg to distal peak delay.
 */
                        temp = ecg_to_dist[i];
                        ecg_to_dist[i] = ecg_to_dist[i - 1];
                        ecg_to_dist[i - 1] = temp;

i--;
                    }
                    pulses++;
                }
            }
        }
        if (pulses == 0)
            pulses++;
```

```
/*
 * Check cuff pressure against open-dump-valve value.
 */
      if (current_cuffp <= dump_pressure) {
         DATASET_COMPLETE = TRUE;
         still_working = FALSE;
      }

/*
 * If the dump valve has been opened, exit immediately. If abnormal end,
 * return immediately. If the data set is full, set the external flag
 * and exit immediately.
 */
      if (BLEED_PROCESS_FINISHED || INTERVAL_UP) {
         still_working = FALSE;
         break;
      }
      if (MODE_IS_STOP)
         return(1);
      if (ABORT2)
         return(2);
      if (pulses >= 100) {
         still_working = FALSE;
         DATASET_COMPLETE = TRUE;
         break;
      }

/*
 * Check for no ECG found during last 20 mmHg of bleeding.
 * The ECG and periodic interrupts must be disabled and then
 * re-enabled after the re-pump.
 */
      if (NO_ECG_FOUND) {
         NO_ECG_FOUND = FALSE;
         if ((last_cuffp - current_cuffp) > 20) {
            re_pump = TRUE;
            if (last_cuffp > 290)
               last_cuffp = 290;
            temp = (int)((last_cuffp + 10) / CUFFP_CONV);
            error = re_inflate(temp);
            if (error)
               return(1);
         }
      }
/*
 * If a large distal pulse is present immediately after pump-up, assume
 * that the pump-up was insufficient and re-pump 30 mmHg greater than
 * the initial pump-up value. Two such re-pumps are allowed per
 * measurement. If a third re-pump is necessary, stop the measurement
 * and re-start after a 10 second wait.
 */
      else
         if (pulses_since_pump < 6) {
            if (current_dist_max > avg_dist_amplitude * 20  &&
                current_dist_max > dist_peak_level / 10) {
               hi_dist_cnt++;
               if (hi_dist_cnt >= 2) {
                  repump_cnt++;
                  hi_dist_cnt = 0;
                  if (repump_cnt < 3) {
                     pulses_since_pump = 0;
                     re_pump = TRUE;
                     PUMP_UP += (int)(ftemp = 30 / CUFFP_CONV);
                     if ((PUMP_UP * CUFFP_CONV) > 300)
                        PUMP_UP = (int)(ftemp = 300 / CUFFP_CONV);
                     error = re_inflate(PUMP_UP);
```

```
                    if (error)
                        return(1);
                }
                else {
                    dump();
                    display(&PRP_DISPLAY,"SYS CHECK", 8,-1,0);
                    return(3);
                }
            }
        }
        else
            hi_dist_cnt = 0;
    }

/*
 * Added 11-13-84 to abort measurement when proximal pulse is insufficient.
 * Compare the proximal pulse to a multiple of the proximal noise level.
 * Use a multiplier of 4 for the rest mode and a multiplier of
 * 8 for the exercise mode.
 */
    if (pulses < 8  &&  !(re_pump)) {
        if (current_prox_max < avg_prox_amplitude * multiplier) {
            if (pi_atten < 60) {
                lo_prox_cnt++;
                if (lo_prox_cnt >= 3) {
                    dump();
                    display(&PRP_DISPLAY,"MIC.CHECK",8,-1,0);
                    error_stop();
                    return(1);
                }
            }
            else {
                set_atten(0);
                IO_CONTROL = io_control |= LOAD_PROXIMAL_ATTEN;
                IO_CONTROL = io_control &= DISABLE_PROXIMAL_ATTEN;
                pi_atten = PI_ATTEN = 0;
            }
        }
        else
            lo_prox_cnt = 0;
    }
    last_cuffp = current_cuffp;
    pulses_since_pump++;
}

$PAGE$
/* ***************************************************************** */
/*                                                                    */
/*   End of cycle processes                                           */
/*                                                                    */
/* ***************************************************************** */

/*
 * Adjust the window openings and widths for the next measurement.
 */
    for (i = 0, temp = 0; i < 10; i++)
        temp += ecg_to_prox[i];
    avg_ecg_to_prox = temp / i;
    open_prox_window = earliest_prox;
    prox_window_length = (avg_ecg_to_prox + (100 / SAMPLE_INTERVAL)) -
            open_prox_window;

/*
 * Find the product of the distal amplitude and the proximal to distal
 * delay time. Since the proximal to distal delay time is found by
 * subtracting the average ECG to proximal delay time from the actual
 * ECG to distal delay time, ensure that negative prox-to-dist delay
```

```
*   times do not occur.
 */
    for (i = 0; i < pulses; i++) {
        if ((temp = ecg_to_dist[i] - avg_ecg_to_prox) < 1)
            temp = 1;
        dist_X_delay[i] = (int)(((long)dist_max[i] * (long)temp) / 20);
    }

/*
 * Median filter the peak data
 */
/*
 * Use a 5-point filter w/o replacement(use a 3-point on first
 * and last points & make 1st and last points zero).
 */
    dist_med[0] = avg_dist_amplitude;
    dxd_med[0] = avg_dist_amplitude;

dist_med[1] = median(dist_max, 2, 3);
    dxd_med[1] = median(dist_X_delay, 2, 3);

for (i = 4, j = 2; i < pulses; i++, j++) {
        dist_med[j] = median(dist_max, i, 5);
        dxd_med[j] = median(dist_X_delay, i, 5);
    } dist_med[j] = median(dist_max, pulses - 1, 3);
    dxd_med[j] = median(dist_X_delay, pulses - 1, 3);

dist_med[pulses - 1] = avg_dist_amplitude;
    dxd_med[pulses - 1] = avg_dist_amplitude;

/*
 * Exponential filter the peak data and the median filtered data.
 */
    exp_filter(dist_med, dist_med_exp, pulses);
    exp_filter(dxd_med, dxd_med_exp, pulses);

/*
 * Find the systolic and diastolic pressures using the distal amplitude
 *  and distal delay product data(median and exponential filtered).
 */
    ftemp = 0.40;
    ERROR_PROD = find(dxd_med_exp, ftemp);

/*
 * Find the systolic and diastolic pressures using amplitude only data.
 */
    ftemp = 0.5;
    ERROR_AMP = find(dist_med_exp, ftemp);

/*
 * Decide which values to use. If the systolic product is available,
 *  use it; otherwise, use the systolic amplitude. If the diastolic
 *  amplitude is available, use it; otherwise, use the diastolic
 *  product. Display the "CHECK MIC." error if no results are available.
 */
    if (SYS_PROD)
        SYSTOLIC = SYS_PROD;
    else if (SYS_AMP)
        SYSTOLIC = SYS_AMP;

else {
        display(&PRP_DISPLAY,"MIC.CHECK", 8,-1,0);
        error_stop();
        set_atten(0);
        IO_CONTROL = io_control |= LOAD_DISTAL_ATTEN;
```

```
        IO_CONTROL = io_control &= DISABLE_DISTAL_ATTEN;
        di_atten = DI_ATTEN = 0;
        return(1);
    } if (DIA_AMP)
        DIASTOLIC = DIA_AMP;
    else if (DIA_PROD)
        DIASTOLIC = DIA_PROD;

else {
        display(&PRP_DISPLAY,"MIC.CHECK", 8,-1,0);
        error_stop();
        set_atten(0);
        IO_CONTROL = io_control |= LOAD_DISTAL_ATTEN;
        IO_CONTROL = io_control &= DISABLE_DISTAL_ATTEN;
        di_atten = DI_ATTEN = 0;
        return(1);
    }

/*
 * Display the systolic and diastolic pressures.
 */
    display(&SYS_DISPLAY,"",0,SYSTOLIC,2);
    display(&DIA_DISPLAY,"",0,DIASTOLIC,2);

/*
 * Set the pump-up and bleed-down values for the next measurement.
 *  Compare the current systolic value to the previous systolic value
 *  and add the over-pump value to the greater of the two values. This
 *  inhibits insufficient pump-up due to a low systolic reading.
 */
    if (MODE_IS_REST) { if (SYSTOLIC < last_sys)
            PUMP_UP = (int)((last_sys + 30) / CUFFP_CONV);
        else
            PUMP_UP = (int)((SYSTOLIC + 30) / CUFFP_CONV);
        BLEED_DOWN = (int)((DIASTOLIC - 20) / CUFFP_CONV);
        GOOD_REST_DATA = TRUE;
    } if (MODE_IS_EXEC) { if (SYSTOLIC < last_sys)
            PUMP_UP = (int)((last_sys + 50) / CUFFP_CONV);
        else
            PUMP_UP = (int)((SYSTOLIC + 50) / CUFFP_CONV);
        BLEED_DOWN = (int)((DIASTOLIC - 30) / CUFFP_CONV);
    } if (BLEED_DOWN < (int)(ftemp = 10.0 / CUFFP_CONV))
        BLEED_DOWN = (int)ftemp;
    else if (BLEED_DOWN > (int)(ftemp = 70.0 / CUFFP_CONV))
        BLEED_DOWN = (int)ftemp;

if (PUMP_UP < (int)(ftemp = 140.0 / CUFFP_CONV))
        PUMP_UP = (int)ftemp;

/*
 * Calculate and display average heart rate.
 */
    if ((dtemp = (double) CURRENT_INT_TIME * (double) 0.976625) <= 0)
        dtemp = 1;
    AVERAGE_HR_DISPLAYED = TRUE;
    if (HR_SWITCH & HR_SWITCH_ON) {
        HEART_RATE = Zlongreal_round(((double) HR_COUNT * 60000) / dtemp);
        if (HEART_RATE > 300)
```

```
      HEART_RATE = 999;
   display(&HR_DISPLAY,"",0,HEART_RATE,2);
}

/*
 * Calculate and display PRP.
 */
   prp_value = ((long)HEART_RATE * (long)SYSTOLIC) / 100;
   if (prp_value > 999)
      prp_value = 999;
   if ((prp[0] = (prp_value / 100) | ASCII_MASK) == ZERO)
      prp[0] = BLANK;
   prp[1] = ((prp_value % 100) / 10) | ASCII_MASK;
   prp[2] = PERIOD;
   prp[3] = (prp_value % 10) | ASCII_MASK;
   display(&PRP_DISPLAY,prp,3,-1,0);

/*
 * Check maximum systolic, diastolic, and heart rate values and set
 *   alarms as necessary.
 */
   if (SYSTOLIC > MAX_SYSTOLIC)
      ALARM_LED = alarm_led |= SYS_LED_ON;
   if (DIASTOLIC > MAX_DIASTOLIC)
      ALARM_LED = alarm_led |= DIAS_LED_ON;
   if (HEART_RATE > MAX_HEART)
      ALARM_LED = alarm_led |= HR_LED_ON;
   if (last_sys - SYSTOLIC > MAX_MMHG)
      ALARM_LED = alarm_led |= SYS_LED_ON;
   last_sys = SYSTOLIC;
   last_dia = DIASTOLIC;

/*
 * Sound audible tone for 1 second to signal end of cycle.
 */
   ALARM_LED = alarm_led |= TONE_ALARM_ON;
   ALARM_ON = YES;

/*
 * Update the proximal and distal attenuators using the maximum
 *   peak values from this cycle.
 */
   PI_ATTEN = adjust_atten(max_prox,PI_ATTEN);
   IO_CONTROL = io_control |= LOAD_PROXIMAL_ATTEN;
   IO_CONTROL = io_control &= DISABLE_PROXIMAL_ATTEN;
   pi_atten = PI_ATTEN;

DI_ATTEN = adjust_atten(max_dist,DI_ATTEN);
   IO_CONTROL = io_control |= LOAD_DISTAL_ATTEN;
   IO_CONTROL = io_control &= DISABLE_DISTAL_ATTEN;
   di_atten = DI_ATTEN;

/*
 * Return with a normal return code.
 */
   return(0);

}

/* ******************************************************************
 *
 * This code was made a subroutine to facilitate the request to
 *   calculate and display blood pressure with the distal only
 *   and product data sets.
 *
 * ******************************************************************
 */
```

```
find(dist_int, fraction)
int dist_int[];
float fraction;
{
   float dist_float[100], cuff_float[100];
   char est_sys_found, est_dia_found;

/*
 * Locate the filtered maximum amplitude and
 *  multiply by the passed constant to find estimated value threshold.
 */
   for (i = 3, dist_peak_level = 0; i < pulses - 3; i++) {
      if (dist_int[i] >= dist_peak_level) {
         dist_peak_level = dist_int[i];
         dist_peak_index = i;
      }
   } dist_threshold = (int)(dist_peak_level * fraction);
/*
 * If four contiguous values around the peak value are not more than
 *  than 10 times the noise level, the data set will considered
 *  insufficient to calculate reasonable results.
 */
   for (i = dist_peak_index - 3, j = 0; i <= dist_peak_index + 3; i++) {
      if (dist_int[i] > avg_dist_amplitude * 10)
         j++;
      else
         j = 0;
      if (j >= 4)
         break;
   } if (j < 4) {
      SYSTOLIC = DIASTOLIC = 0;
      return(4);
   }

/*
 * Find the estimated systolic point by looking for the last point
 *  that is above 50% of the product data maximum
 *  working thru the data from the peak to the beginning.
 */
   for (i = dist_peak_index, est_sys_index = 0, j = 0; i > 0; i--) {
      if (dist_int[i] < dist_threshold)
         j++;
      else
         j = 0;
      if (j >= 3) {
         estimated_sys = cuff_pressure[i + 3];
         est_sys_index = i + 3;
         est_sys_found = TRUE;
         break;
      }
   }

/*
 * If there are no points below the threshold level, set the flag
 *  to disable systolic calculation.
 */
   if (est_sys_index == 0) {
      est_sys_found = FALSE;
      SYSTOLIC = 0;
   }

/*
 * Find the estimated diastolic point by looking for the last point
```

```
*     that is above 50% of the distal maximum
*     working thru the data from the peak point to the end.
*/
   for (i = dist_peak_index, est_dia_index = 0, j = 0; i < pulses - 1; i++) {
      if (dist_int[i] < dist_threshold)
         j++;
      else
         j = 0;
      if (j >= 3) {
         estimated_dia = cuff_pressure[i - 3];
         est_dia_index = i - 3;
         est_dia_found = TRUE;
         break;
      }
   }
/*
* If there are no points below the threshold level, return an
*  insufficient distal data error.
*/
   if (est_dia_index == 0) {
      est_dia_found = FALSE;
      DIASTOLIC = 0;
   }

/*
* Convert to floating point for statistical computations.
*/
   for (i = 0; i < pulses; i++) {
      cuff_float[i] = (float)(cuff_pressure[i]);
      dist_float[i] = (float)(dist_int[i]);
   }

/*
* Find the systolic point by using the iterative method of slope
*  deviation working thru the data forwards.
*/
   if (est_sys_found) {

/*
* Initialize the sums.
*/
      provisional_sys = 999;
      sum_x = sum_y = sum_xy = sum_x2 = sum_y2 = 0;

for (i = j = k = n = 0; i < 3; i++, j++)
         sums(cuff_float[i], dist_float[i]);

/*
* Check the latest provisional value against the limit.
*/
      while (provisional_sys > estimated_sys + 5) {

/*
* Check the indexing.
*/
         while ( i < dist_peak_index + 3) {

/*
* Get the new 'x' and 'y' values.
*/
            x = cuff_float[i];
            y = dist_float[i];

/*
* If previous point didn't deviate, 'x' and 'y' were added to the
*  sums. Therefore, re-calculate s.d., slope, y-intercept.
* Re-calculate expected value, prediction interval, prediction
```

```
 *  range in any case.
 */
            if (k == 0)
                stats(j);
            calc_pred(x, j);
            expected_value = y_int + slope * x;
            prediction_range = expected_value + prediction_interval;

/*
 * Check 'y' against prediction range. If greater then increment counter.
 * Otherwise, clear counter and add 'x' and 'y' to sums.
 */
            if (y > prediction_range)
                k++;
            else {
                k = 0;
                sums(x, y);
                j++;
            }

/*
 * If 3 deviations in a row, save second value back as provisional value
 * and save its location. Reset array index to point at provisional
 * value: it will become part of the next iteration.
 */
            if (k == 3) {
                k = 0;
                ind_array[++n] = i -= 1;
                provisional_sys = cuff_pressure[i];
                i--;
                sums(cuff_float[i], dist_float[i]);
                i++; j++;
                break;
            }
            i++;
        }

/*
 * If no provisionals were found yet then make
 * the estimated value a provisional value.
 */
        if (i >= dist_peak_index + 3) {
            if (provisional_sys == 999) {
                provisional_sys = estimated_sys;
            }
            break;
        }
    }

/*
 * Reject the provisional values if the preceeding provisional is
 * also the previous data point.
 */
    if (n > 1) {
        while (ind_array[n] - 1 == ind_array[n - 1] && n > 1)
            n--;
        provisional_sys = cuff_pressure[ind_array[n]];
    }

/*
 * Provisional systolic cannot be less than the estimated systolic.
 */
    if (provisional_sys < estimated_sys) {
        provisional_sys = estimated_sys;
    }

SYSTOLIC = provisional_sys;
}
```

```
/*
 * Find the diastolic point by using the iterative method of slope
 *   deviation working thru the data backwards.
 */
   if (est_dia_found) {

/*
 * Initialize the sums.
 */
      sum_x = sum_y = sum_xy = sum_x2 = sum_y2 = 0;
      provisional_dia = 0;

for (i = pulses - 1, j = k = n = 0; j < 3; i--, j++)
         sums(cuff_float[i], dist_float[i]);

/*
 * Check the latest provisional value against the limit.
 */
      while (provisional_dia < estimated_dia - 5) {

/*
 * Check the indexing.
 */
         while ( i > dist_peak_index - 3) {

/*
 * Get the new 'x' and 'y' values.
 */
            x = cuff_float[i];
            y = dist_float[i];

/*
 * If previous point didn't deviate, 'x' and 'y' were added to the
 * sums. Therefore, re-calculate s.d., slope, y-intercept.
 * Re-calculate expected value, prediction interval, prediction
 * range in any case.
 */
            if (k == 0)
               stats(j);
            calc_pred(x, j);
            expected_value = y_int + slope * x;
            prediction_range = expected_value + prediction_interval;

/*
 * Check 'y' against prediction range. If greater then increment counter.
 * Otherwise, clear counter and add 'x' and 'y' to sums.
 */
            if (y > prediction_range)
               k++;
            else {
               k = 0;
               sums(x, y);
               j++;
            }

/*
 * If 3 deviations in a row, save second value back as provisional value
 * and save its location.
 */
            if (k == 3) {
               k = 0;
               ind_array[++n] = i += 1;
               provisional_dia = cuff_pressure[i];
               i++;
               sums(cuff_float[i], dist_float[i]);
               i--; j++;
               break;
```

```
            }
            i--;
        }

/*
 * If no provisionals were found yet then make
 *   the estimated value a provisional value.
 */
        if (i <= dist_peak_index - 3) {
            if (provisional_dia == 0) {
                provisional_dia = estimated_dia;
            }
            break;
        }
    }

/*
 * Reject the provisional values if the preceeding provisional is
 *   also the previous data point.
 */
    if (n > 1) {
        while (ind_array[n] + 1 == ind_array[n - 1]  &&  n > 1)
            n--;
        provisional_dia = cuff_pressure[ind_array[n]];
    }

/*
 * Provisional diastolic cannot be greater than the estimated diastolic.
 */
    if (provisional_dia > estimated_dia) {
        provisional_dia = estimated_dia;
    }

DIASTOLIC = provisional_dia;
    }

/*
 *   Return with code indicating results obtained:
 *          0 = normal
 *          1 = systolic result only
 *          2 = diastolic result only
 *          3 = neither result was found
 */
    return(!est_sys_found + (!est_dia_found * 2));
}

/*
 * Add the supplied values of 'x' and 'y', and the squares and cross-product
 *   to the current sums.
 */
sums(x, y)
double x, y;
{
    sum_x  += x;
    sum_y  += y;
    sum_xy += x * y;
    sum_x2 += x * x;
    sum_y2 += y * y;
}

/*
 * Calclate the necessary statistical quantities using the globally
 *   available sums of 'x' and 'y' and the supplied value of 'n'.
 */
stats(n)
int n;
{
```

```
    SSx = sum_x2 - (sum_x * sum_x) / n;
    SSy = sum_y2 - (sum_y * sum_y) / n;
    SSxy = sum_xy - (sum_x * sum_y) / n;
    mean_x = sum_x / n;
    mean_y = sum_y / n;

slope = SSxy / SSx;
    y_int = mean_y - slope * mean_x;
    if ((z = (SSy - slope * SSxy) / (n - 2)) < 0)
        z = 0;
    sd = SQRT(z);
}

/*
 * Calculate the prediction interval for the supplied 'x' value using globally
 *  available statistical quantities and the critical values of the
 *  Student's 't' test.
 */
calc_pred(x, n)
double x;
int n;
{
    int index;

if ((index = n - 2) >= T_SIZE)
        index = T_SIZE;
    if ((z = 1.0 + (1.0 / n) + ((x - mean_x) * (x - mean_x) / SSx)) < 0)
        z = 0;
    prediction_interval = t_values[index - 1] * sd * SQRT(z);
}

/*
 * Re-pump subroutine
 */
re_inflate(pumpup_value)
int pumpup_value;
{
    ECG_CONTROL = ecg_control &= DISABLE_ECG_INT;
    REG_B &= DISABLE_PIE;
    if (pump(pumpup_value) == FAIL)
        return(1);
    REG_A = PIR_02;
    REG_B |= ENABLE_PIE;
    FIRST_ECG = YES;
    ECG_CONTROL = ecg_control |= ENABLE_ECG_INT;
    return(0);
}

/*
 * Error stop subroutine. Turn off the interval clock and set the
 *  mode to STOP.
 */
error_stop()
{
    REG_B &= DISABLE_AIE;
    CLOCK_RUNNING = NO;
    ERROR_CONDITION = YES;
    stop();
/*
 * Function to open the dump valve and bleed valve.
 */
dump()
{
    IO_CONTROL = io_control &= DUMP_VALVE_OPEN;
    BLEED_VALVE = bleed_valve &= BLEED_VALVE_OPEN;
}
```

```
"C"
"68000"
$EXTENSIONS ON$
$FAR ON$
$CALL_ABS_LONG ON$
$LIB_ABS_LONG ON$
$ASM_FILE$
$INIT_ZEROES OFF$
$WARN OFF$
include "DEFINES"

extern int REG_A,REG_B,SYS_DISPLAY,PRP_DISPLAY,SELECTION,SECOND;
extern short PROGRAMMED_MAX_CUFF;
```

```
                        /********************/
/*************************      PROGRAM      *****************************/
                        /********************/

/*
  Routine Name         : program
  Parameters Passed    : *value -- address of digital value to be displayed
                         v_limit -- digit size
                         setting -- programmable switch setting at time
                                    routine was called
                         max -- maximum digit to be displayed
                         min -- minimum digit to be displayed
                         inc -- digit increment value
                         string -- string array containing message to be
                                   displayed
                         s_limit -- string size
                         displacement -- display offset
  Parameters Returned  :  --
  Calling Routines     : programming_mode
  Routines Called      : display, read_sw, delay
  Local Variables      : temp -- temporary storage
*/ program (value,v_limit,setting,max,min,inc,string,s_limit,displacement)
short v_limit,s_limit,max,min,inc,displacement;
int setting,*value;
char string[];
{int temp;
 temp = *value;

/*
  Inhibit any further update cycles by the Real-Time Clock when its parameters
  are programmed by the user.  This routine expects integer values.  The
  values of the Real-Time Clock are in the lower byte of a word.  The
  upper byte must be masked off.
*/ if (setting==hour || setting==minute || setting==year ||
      setting==month || setting==date){
    while (REG_A & UPDATE_CYCLE_IN_PROGRESS)
      ;
    temp = *value & LOW_BYTE_MASK;
    REG_B |= STOP_UPDATE_CYCLE;
  }

/*
  Programmable parameters are displayed in the ELAPSED TIME and PRP
  displays.  All other displays remain blank.
*/ display (&SYS_DISPLAY,"",0,-2,17);
  if (setting == unassigned && temp == max)
    display(&PRP_DISPLAY,"AUTOLEAD ",8,-1,0);
```

```
else
   display (&PRP_DISPLAY+displacement,string,s_limit,temp,v_limit);

/*
Monitor the operator's selections until the 12 position switch setting
is changed or the SET key depressed.
*/ read_sw();
 while (SELECTION & setting){
    while (((SELECTION & modify)==0) && (SELECTION & setting))
      read_sw();

/*
Either the operator has changed settings or the SET key has been
depressed.  Modify the programmable parameter in a circular fashion
from a minimum to maximum increment value if the SET key was depressed.
*/ if ((SELECTION & modify) && (SELECTION & setting)){
       (temp >= max) ? (temp = min) : (temp += inc);
/*
Set a flag when the CUFF parameter is modified
*/ if (setting == cuff)
       PROGRAMMED_MAX_CUFF = YES;

/*
Remove the previous modified value.  Display the new modified value.
*/ display(&PRP_DISPLAY,"",0,-2,3);
       if (setting == unassigned && temp == max)
          display(&PRP_DISPLAY,"AUTO",3,-1,0);
       else
          display(&PRP_DISPLAY+displacement,"",0,temp,v_limit);

/*
Delay 400 milliseconds.  This continously increments the parameter at a
rate of three values per second.
*/ delay(9CH,40H);
    }

/*
Get operator selection.
*/ read_sw();
 }

/*
If the Real-Time Clock Hour or Minute values were changed then reset
Seconds.
*/
    if (setting == hour || setting == minute)
       SECOND = 00H;
 /*
   Assign the modified value to the programmable parameter and resume
   Real-Time Clock update cycles.
 */

*value = temp;
   REG_B &= RESUME_UPDATE_CYCLE;
   return;
  }
```

```
"C"
"68000"
$EXTENSIONS ON$
$FAR ON$
$CALL_ABS_LONG ON$
$LIB_ABS_LONG ON$
$ASM_FILE$
$INIT_ZEROES OFF$
$WARN OFF$
include "DEFINES"

extern int    SELECTION,SWITCH_LED,switch_led,ALARM_LED,alarm_led,
              MAX_SYSTOLIC,MAX_DIASTOLIC,MAX_HEART,MAX_MMHG,MAX_CUFF,
              MONTH,DATE,YEAR,HOUR,MINUTE,LEAD,TRIGGER_LEAD;

extern short MODE_IS_PROGRAM,PROCESSING_LEAD_SELECTION,
              LEAD_SELECTION_COMPLETE,ecg_control,MODE_IS_MODIFY,
              STATUS_OF_LEAD_SELECTION;

extern unsigned short ECG_CONTROL;

#define Off        0800H
#define Systolic   0400H
#define Diastolic  0200H
#define Heart      0100H
#define mmHg       0080H
#define Cuff       0040H
#define Month      0020H
#define Date       0010H
#define Year       0008H
#define Hour       0004H
#define Minute     0002H
define Unassigned 0001H /********************/
/*********************** PROGRAMMING MODE ***************************/
                       /********************/

/*
  Routine Name          : programming_mode
  Parameters Passed     : --
  Parameters Returned   : --
  Calling Routines      : standby_mode
  Routines Called       : read_sw, program, validate
  Local Variables       : max -- maximum date value allowed to be displayed
*/ programming_mode()
{short max;

/*
  Turn off all alarm LED's and disable function of the STOP/RUN key.
*/

SWITCH_LED = switch_led &= DISABLE_SS_INT;
  ALARM_LED = alarm_led &= ALARM_LEDS_OFF;
  MODE_IS_PROGRAM = YES;
  max = 0;

/*
  Get operator selection. Return to the Standby mode if the 12 position
  switch is in the OFF position. Otherwise, program the parameter. Some
  of the parameters are from tne Real-Time Clock and must be validated
  before programming. The N/A position is being used as an automatic/
  manual option for processing the lead selection.
*/
```

```
read_sw();
while((SELECTION & off)==0){
  read_sw();
  switch(SELECTION & 0FFFH){
    case Off         : break;
    case Systolic    : program(&MAX_SYSTOLIC,2,systolic,
                               SYSMAX,SYSMIN,SYSINC,"SYS.",3,1);
                       break;
    case Diastolic   : program(&MAX_DIASTOLIC,2,diastolic,
                               DIAMAX,DIAMIN,DIAINC,"DIAS.",4,1);
                       break;
    case Heart       : program(&MAX_HEART,2,heart,
                               HRTMAX,HRTMIN,HRTINC,"H.R.",3,1);
                       break;
    case mmHg        : program(&MAX_MMHG,1,mmhg,
                               MHGMAX,MHGMIN,MHGINC,"mmHg",3,2);
                       break;
    case Cuff        : program(&MAX_CUFF,2,cuff,
                               CUFMAX,CUFMIN,CUFINC,"CUFF",3,1);
                       break;
    case Month       : validate(&MONTH,12,1,month);
                       program(&MONTH,1,month,12,1,1,"MONTH",4,2);
                       break;
    case Date        : max = validate(&DATE,0,1,date);
                       program(&DATE,1,date,max,1,1,"DATE",3,2);
                       break;
    case Year        : validate(&YEAR,99,YEAR_SETTING,year);
                       program(&YEAR,1,year,99,YEAR_SETTING,1,"YEAR",3,2);
                       break;
    case Hour        : validate(&HOUR,23,0,hour);
                       program(&HOUR,1,hour,23,0,1,"HOUR",3,2);
                       break;
    case Minute      : validate(&MINUTE,59,0,minute);
                       program(&MINUTE,1,minute,59,0,1,"MIN.",3,2);
                       break;
    case Unassigned  : program(&LEAD,0,unassigned,4,1,1,"LEAD",3,3);
                       PROCESSING_LEAD_SELECTION = NO;
                       STATUS_OF_LEAD_SELECTION = NO;
                       LEAD_SELECTION_COMPLETE = YES;

/*
 Select the trigger lead if manually programmed by the user.  Enable
 lead selection processing if the automatic mode was programmed.
*/
                       switch (LEAD){
                         case 1 : TRIGGER_LEAD = ECG_LEAD1;
                                  break;
                         case 2 : TRIGGER_LEAD = ECG_LEAD2;
                                  break;
                         case 3 : TRIGGER_LEAD = ECG_LEAD3;
                                  break;
                         case 4 : PROCESSING_LEAD_SELECTION = YES;
                                  STATUS_OF_LEAD_SELECTION = YES;
                                  LEAD_SELECTION_COMPLETE = NO;
                                  break;
                       }
/*
 Select the lead manually programmed by the user.
*/
                       if (!PROCESSING_LEAD_SELECTION){
                          ECG_CONTROL = ecg_control &= CLEAR_LEAD_SELECTION;
                          ECG_CONTROL = ecg_control |= TRIGGER_LEAD;
                       }
                       break;
  }
}
```

```
MODE_IS_PROGRAM = MODE_IS_MODIFY = NO;
SWITCH_LED = switch_led |= ENABLE_SS_INT;
}
"C"
"68000"
$EXTENSIONS ON$
$FAR ON$
$CALL_ABS_LONG ON$
$LIB_ABS_LONG ON$
$ASM_FILE$
$INIT_ZEROES OFF$
$WARN OFF$
include "DEFINES"

extern unsigned int bleed_valve;

extern int IO_CONTROL,io_control,REG_A,SECOND,REG_B,PUMP_UP,
           CUFFP_OFFSET,PRP_DISPLAY,SYS_DISPLAY,LAST_CUFF_PRESSURE,
           timer2_cntrl_reg,TIMER2_CNTRL_REG,MSB3_BUFFER,TIMER3_LATCH;

extern short MODE_IS_START,PIR_DETECTED,DATA_OK,IN_PUMP,FIRST_BLEED,K,
             ABORT2,BLEED_RATE_ESTABLISHED,CLOCK_RUNNING,ERROR_CONDITION;

extern unsigned short BLEED_VALVE;

#define avg_count 25

/*********************/
/************************    PUMP     ******************************/
                        /*********************/

/*
  Routine Name         : pump
  Parameters Passed    : --
  Parameters Returned  : pump status:
                            0 -- fail
                            1 -- pass
  Calling Routines     : manual_mode, preprocess, process, pump
  Routines Called      : acquire_data, display, stop, pump
  Local Variables      : old_time -- time in seconds when pump started
                         time -- time in seconds since pump started
                         count -- number of good data samples from the A/D
                         i -- loop counter
                         temp -- temporary storage
                         raw_cuff_pressure -- bit representation of cuff
                                              pressure
                         cuff_pressure -- digital (mmHg) representation of
                                          cuff pressure
                         total -- summation of data sampling from the A/D
                         pump_status -- flag signaling pass or fail pump up
*/ pump()
{int old_time,time,count,i,temp,raw_cuff_pressure,cuff_pressure;
 long total;
 short pump_status;

/*
  Pump up only while the the RUN mode is activated.
*/ if (MODE_IS_START){

/*
  Initialize variables.
*/
```

```
    raw_cuff_pressure = 0;
    FIRST_BLEED = IN_PUMP = YES;
    BLEED_RATE_ESTABLISHED = NO;
    K = 0;

/*
Close bleed and dump valves.  Turn on the pump.
*/

BLEED_VALVE = bleed_valve |= BLEED_VALVE_CLOSED;
    IO_CONTROL = io_control |= DUMP_VALVE_CLOSED;
    IO_CONTROL = io_control &= PUMP_ON;

/*
Record a starting pump time.
*/ while (REG_A & UPDATE_CYCLE_IN_PROGRESS)
        ;
    old_time = SECOND & LOW_BYTE_MASK;

/*
Continue pumping until the desired cuff pressure is obtained or
the measurement cycle is stopped.
*/ while (raw_cuff_pressure < PUMP_UP && MODE_IS_START){

/*
Sample cuff pressure and send to the SYSTOLIC display.
*/ for (i=count=total=0; i<avg_count; i++){
          if ((temp = acquire_data(CUFF_PRESSURE) - CUFFP_OFFSET) < 0)
            temp = 0;
          if (DATA_OK){
            total += temp;
            count++;
          }
        }
        if (count == 0)
          count = 1;
        cuff_pressure = (raw_cuff_pressure = total / count) * CUFFP_CONV;
        display (&SYS_DISPLAY,"",0,cuff_pressure,2);

/*
Display an error message and return a bad pump up status if the pump up
time has exceeded 10 seconds.
*/ while (REG_A & UPDATE_CYCLE_IN_PROGRESS)
            ;
        if ((time = (SECOND & LOW_BYTE_MASK) - old_time) < 0)
          time += 60;

/*
Do not display "CHECK CUFF" message if "abort2" processing was done
during pump up.  This will cause an false error with this routine as
"abort2" processing takes 10 seconds ("CHECK CUFF" appears if pump up
time exceeds 10 seconds).  Return a value of "YES" for a good pump
status so that processing will not return to the Standby mode.
(Max pump-up time changed to 15 seconds because of slower pump rate
 of the N-C machine. 1-14-85)
*/ if (ABORT2)
          return (YES);
```

```
    if (time > 14 && MODE_IS_START && !ABORT2){
      IO_CONTROL = io_control |= PUMP_OFF;
      IO_CONTROL = io_control &= DUMP_VALVE_OPEN;
      BLEED_VALVE = bleed_valve &= BLEED_VALVE_OPEN;
      REG_B &= DISABLE_AIE;
      CLOCK_RUNNING = NO;
      ERROR_CONDITION = YES;
      display(&SYS_DISPLAY,"  0  0  0CUFFCHECK",17,-1,0);
      stop();
      IN_PUMP = NO;
      return(NO);
    }
  }

/*
 The desired cuff pressure has been obtained.  Turn off the pumps and
 delay 3/4 second.  Perform a recursive call to this routine if the cuff
 was not properly inflated.
*/

IO_CONTROL = io_control |= PUMP_OFF;
   if (MODE_IS_START){
     PIR_DETECTED = NO;
     REG_A = PIR_500;
     REG_B |= ENABLE_PIE;
     while (!PIR_DETECTED)
        ;
     REG_A = PIR_250;
     PIR_DETECTED = NO;
     while (!PIR_DETECTED)
        ;
     REG_B &= DISABLE_PIE;
/*
 Sample the cuff pressure.
*/ for (i=count=total=0; i<avg_count; i++){
       if ((temp = acquire_data(CUFF_PRESSURE) - CUFFP_OFFSET) < 0)
         temp = 0;
       if (DATA_OK){
         total += temp;
         count++;
       }
     }
     if (count == 0)
       count = 1;
/*
 Test the cuff pressure against the desired cuff pressure.
*/ raw_cuff_pressure = total / count;
     if (raw_cuff_pressure < (PUMP_UP - PUMP_OFFSET) && MODE_IS_START){
        if ((pump_status = pump(PUMP_UP)) == NO){
          IN_PUMP = NO;
          return(NO);
        }
            else{
              IN_PUMP = NO;
              return(YES);
            }
       }
       else{
          IN_PUMP = NO;
          return(YES);
       }
    }
```

```
              else{
                IN_PUMP = NO;
                return(NO);
              }
            }
          }
"68000"

;                             /********************/
;****************************     RAM TEST      ****************************
;                             /********************/

;Routine Name           :   ram_test
;Parameters Passed      :   --
;Parameters Returned    :   -2[A6] -- bad RAM count
;Calling Routines       :   check_ram
;Routines Called        :   --
;Local Variables        :   D0 -- RAM address undergoing test and end of
;                                 buffer pointer
;                           D1 -- temporary storage
;                           A0 -- buffer pointer and temporary storage
;                           A1 -- RAM buffer start address EXTERNAL       TIMER2_CNTRL_RE,TIMER1_3_CNTRL_REG,TIMER3_LATCH
          EXTERNAL       timer2_cntrl_reg,timer1_3_cntrl_reg,MSB3_BUFFER
          GLOBAL         ram_test

PROG ram_test
          LINK           A6,#-2
          CLR            -2[A6]                          ;set bad ram count to 0
          MOVE.L         #20000H,D0                      ;get RAM start address
          ANDI.W         #000FEH,timer2_cntrl_reg        ;select prog. timer 3
          MOVE.W         timer2_cntrl_re,TIMER2_CNTRL_REG
MAIN_LP   CMPI.L         #3FFFFH,D0                      ;finished?
          BHI            FINISHED
          CMPI.L         #200FFH,D0                      ;test buffer first
          BCS            WRITE_A
RAM_BUF   MOVE.L         D0,A1                           ;get buffer start addr.
          MOVE.L         #20000H,A0                      ;initialize buffer ptr
LOOP1     MOVE.L         A0,D1                           ;end of buffer xfer?
          CMPI.L         #200FFH,D1
          BHI            WRITE_A                         ;yes-write 'AAAA'
          MOVE           [A1]+,[A0]+                     ;no--continue transfer
          BRA.S          LOOP1
WRITE_A   MOVE.L         D0,A1                           ;get block start addr.
          LEA            256[A1],A0                      ;get block end address
LOOP2     CMP.L          A0,A1                           ;finished block?
          BCC            DELAY1                          ;yes-set up delay
          MOVE.W         #0AAAAH,[A1]+                   ;no--continue 'AAAA'
          BRA.S          LOOP2
DELAY1    MOVE.W         #00001H,MSB3_BUFFER             ;delay 3ms
          MOVE.W         #0002CH,TIMER3_LATCH
DELAY_L1  MOVE.W         TIMER2_CNTRL_REG,D1
          ANDI.W         #0004H,D1
          TST.W          D1                              ;delay up?
          BNE            READ_A                          ;yes-verify 'AAAA'
          BRA.S          DELAY_L1                        ;no--continue delay
READ_A    MOVE.L         D0,A1                           ;get block start addr.
          LEA            256[A1],A0                      ;get block end addr.
LOOP3     CMP.L          A0,A1                           ;finished block?
          BCC            DELAY2                          ;yes-set up delay
          CMPI.W         #0AAAAH,[A1]                    ;no--verify 'AAAA'
          BEQ            WRITE_5                         ;good-write '5555'
          ADDQ.W         #1,-2[A6]                       ;bad--inc. bad count
WRITE_5   MOVE.W         #5555H,[A1]+                    ;write '5555' to RAM
```

```
            BRA.S       LOOP3
DELAY2      MOVE.W      #00001H,MSB3_BUFFER         ;delay 3ms
            MOVE.W      #0002CH,TIMER3_LATCH
DELAY_L2    MOVE.W      TIMER2_CNTRL_REG,D1
            ANDI.W      #0004H,D1
            TST.W       D1                          ;delay up?
            BNE         READ_5                      ;yes-verify '5555'
            BRA.S       DELAY_L2                    ;no--continue delay
READ_5      MOVE.L      D0,A1                       ;get block start addr.
            LEA         256[A1],A0                  ;get block end address
LOOP4       CMP.L       A0,A1                       ;finished block?
            BCC         BUF_RAM                     ;yes-transfer RAM
            CMPI.W      #5555H,[A1]+                ;no--verify '5555'
            BEQ         LOOP4                       ;good-continue verifying
            ADDQ.W      #1,-2[A6]                   ;bad--inc. bad count
            BRA.S       LOOP4
BUF_RAM     CMPI.L      #200FFH,D0                  ;buffer tested?
            BCS         NXT_BLK                     ;yes-test next block
            MOVE.L      D0,A1                       ;no-get blk start addr.
            MOVE.L      #20000H,A0                  ;get buffer start addr.
LOOP5       MOVE.L      A0,D1                       ;finished transfer?
            CMPI.L      #200FFH,D1
            BHI         NXT_BLK
            MOVE        [A0]+,[A1]+                 ;transfer RAM buffer
            BRA.S       LOOP5
NXT_BLK     MOVE.L      D0,A1                       ;get new blk start addr.
            LEA         256[A1],A0                  ;get new blk end addr.
            MOVE.L      A0,D0
            BRA         MAIN_LP
FINISHED    MOVE.W      -2[A6],D7                   ;send bad RAM count
            EXT.L       D7
            UNLK        A6
            RTS END
"C"
"68000"
$EXTENSIONS ON$
$FAR ON$
$CALL_ABS_LONG ON$
$LIB_ABS_LONG ON$
$WARN OFF$
$INIT_ZEROES OFF$
$ASM_FILE$
#include "DEFINES"

extern int SELECTION,SWITCH_BUFFER,SWITCH_LED,switch_led;

extern short MODE_IS_STOP,MODE_IS_PROGRAM,PREVIOUS_ERROR_CONDITION,
        SELFTEST_OLD_STATE,MODE_IS_SELFTEST,
        MODE_IS_HALT,REST_EXEC_OLD_STATE,ERROR_CONDITION,
        MODE_IS_REST,REST_MODE_STATUS,MODE_IS_EXEC,FIRST_TIME,
        MODE_IS_MANUAL,MANUAL_OLD_STATE;

#define Off         0FH
#define Systolic    0EH
#define Diastolic   0DH
#define Heart       0CH
#define mmHg        0BH
#define Cuff        0AH
#define Month       09H
#define Date        08H
#define Year        07H
#define Hour        06H
#define Minute      05H
#define Unassigned  04H
```

```
/*********************/
/************************** READ SW  ****************************/
                         /*********************/

/*
 Routine Name         : read_sw
 Parameters Passed    : --
 Parameters Returned  : --
 Calling Routines     : halt, program, programming_mode, standby_mode
 Routines Called      : delay
 Local Variables      : old_sw_buffer -- previous switch buffer contents
                        new_sw_buffer -- current switch buffer contents
                        i -- loop counter
                        temp -- temporary storage
*/ read_sw()
{
int old_sw_buffer,new_sw_buffer,i,temp;

/*
 Initialize variables.
*/ old_sw_buffer = new_sw_buffer = i = 0;
SELECTION = 0;

/*
 Get a starting value for the previous switch buffer variable.
*/
temp = old_sw_buffer = SWITCH_BUFFER & LOW_BYTE_MASK;

/*
 Monitor user selections every millisecond until three consecutive selections
 of the same setting are found.  Restart the consecutive count value when a
 difference between the previous and current setting values is found.
*/ for (i = 0 ; i < 2 ;i++){
    if (old_sw_buffer != (new_sw_buffer = SWITCH_BUFFER & LOW_BYTE_MASK))
       i = 0;
    old_sw_buffer = new_sw_buffer;
    delay(00H,64H);
  }

/*
 Allow all modes to be operational if the STOP key is selected.
*/ if (MODE_IS_STOP){

/*
 Allow operation of the Self-test mode if the 12 position switch is OFF.
 This mode can only be entered after hitting the SELF TEST key three
 times within two seconds.
*/ if (!MODE_IS_PROGRAM){

/*
 SELF TEST key debouncing.  A press and release of the key must be seen
 before selection is acknowledged.
*/ if ((old_sw_buffer & SELFTEST_DEPRESSED)==0)
         SELFTEST_OLD_STATE = 0;
      else if (SELFTEST_OLD_STATE == 0){
```

```
              SELECTION |= selftest ;
              MODE_IS_SELFTEST = YES ;
              SELFTEST_OLD_STATE = 1;
          }
      }

/*
Allow operation of the SET key.  This key does not need to be debounced.
The Programming mode requires parameter modification either by single
stepping or by three values per second.  The Manual mode requires that
the key be depressed in conjunction with the RUN key.
*/ if ((old_sw_buffer & MODIFY_DEPRESSED)==0)
         SELECTION |= modify;

/*
Allow the REST/EXER and MANUAL keys to operate if the 12 position switch
is OFF and the self-tests are not being run.
*/ if (!MODE_IS_HALT && !MODE_IS_PROGRAM){

/*
REST/EXER key debouncing.
*/ if ((old_sw_buffer & REST_EXEC_DEPRESSED) == 0 )
            REST_EXEC_OLD_STATE = 0;
/*
Either the Rest or Exercise mode was selected so make sure Manual mode
LED is off.
*/ else if (REST_EXEC_OLD_STATE == 0){
            SELECTION |= restexec;
            MODE_IS_MANUAL = NO;
            FIRST_TIME = YES;
            SWITCH_LED = switch_led &= MANUAL_LED_OFF;

/*
Store the REST/EXER LED status when a Rest or Exercise to Manual mode
transition is detected.
*/ if (REST_MODE_STATUS){
               MODE_IS_REST = REST_MODE_STATUS = NO;
               SWITCH_LED = switch_led &= REST_LED_OFF;
               MODE_IS_EXEC = YES;
               SWITCH_LED = switch_led |= EXEC_LED_ON;
            }
            else{
               MODE_IS_EXEC = NO;
               SWITCH_LED = switch_led &= EXEC_LED_OFF;
               MODE_IS_REST = REST_MODE_STATUS = YES;
               SWITCH_LED = switch_led |= REST_LED_ON;
            }
            REST_EXEC_OLD_STATE = 1;
         }

/*
MANUAL key debouncing.
*/ if ((old_sw_buffer & MANUAL_DEPRESSED)==0)
            MANUAL_OLD_STATE = 0;
```

```
/*
 Restore the REST/EXER LED status when a Manual to Rest or Exercise
 mode transition is detected.
*/
      else if (MANUAL_OLD_STATE == 0){
         SELECTION |= manual;
         FIRST_TIME = YES;
         REST_MODE_STATUS = (MODE_IS_REST) ? 0 : 1;
         MODE_IS_REST = MODE_IS_EXEC = NO;
         SWITCH_LED = switch_led &= (REST_LED_OFF & EXEC_LED_OFF);
         MODE_IS_MANUAL = YES;
         SWITCH_LED = switch_led |= MANUAL_LED_ON;
         MANUAL_OLD_STATE = 1;
      }
   }

/*
 Allow the 12 position switch to operate when the self-tests are not
 being run.
*/
   if (((old_sw_buffer & SWITCH_MASK) >= Unassigned) && !MODE_IS_SELFTEST){
      MODE_IS_PROGRAM = YES;
      switch (old_sw_buffer & SWITCH_MASK){
         case Off        : SELECTION |= off;
                           MODE_IS_PROGRAM = NO;
                           break;
         case Systolic   : SELECTION |= systolic;
                           break;
         case Diastolic  : SELECTION |= diastolic;
                           break;
         case Heart      : SELECTION |= heart;
                           break;
         case mmHg       : SELECTION |= mmhg;
                           break;
         case Cuff       : SELECTION |= cuff;
                           break;
         case Month      : SELECTION |= month;
                           break;
         case Date       : SELECTION |= date;
                           break;
         case Year       : SELECTION |= year;
                           break;
         case Hour       : SELECTION |= hour;
                           break;
         case Minute     : SELECTION |= minute;
                           break;
         case Unassigned : SELECTION |= unassigned;
                           break;
      }
   }
   if (ERROR_CONDITION && (SELECTION & ~off)){
      ERROR_CONDITION = NO;
      PREVIOUS_ERROR_CONDITION = YES;
   }
  }
 }

"C"
"68000"
$EXTENSIONS ON$
$FAR ON$
$WARN OFF$
$INIT_ZEROES OFF$
$CALL_ABS_LONG ON$
$LIB_ABS_LONG ON$
#include "DEFINES"
```

```
extern int MAX_AMPLITUDE;
extern unsigned int RAW_DATA_POSITION;
extern float AVG_MAX_AMPLITUDE;
```

/*********************/
/********************** SEACRCH_MAX **************************/
/*********************/

```
/*
  Routine Name        : search_max
  Parameters Passed   : array  -- name of array to be searched
                        length -- length of array to be searched
  Parameters Returned : index
  Calling Routines    : select_lead
  Routines Called     : -
  Local Variables     :
                        current_minima_position  -- position in array of
                                                    current minima
                        current_maxima_position  -- position in array of
                                                    current maxima
                        time_between_peaks       -- time between current
                                                    minima and maxima
                        index                    -- current position in
                                                    array
                        end                      -- last position in
                                                    array to search
                        minimum_time             -- minimum time allowed
                                                    between current
                                                    minima and maxima
                        maximum_time             -- maximum time allowed
                                                    between current
                                                    minima and maxima
                        current_minima           -- digital value of
                                                    current minima
                        current_maxima           -- digital value of
                                                    current maxima
*/ search_max(array,length)
int array[], length;

{int time_between_peaks, minimum_time, maximum_time,
     current_minima_position, current_maxima_position,
     current_minima, current_maxima,temp,end,
     peak_count, index;
 long peak_total;

/*
  Initialization
*/ current_minima_position = current_maxima_position = index = 0;
 peak_count = peak_total = current_minima = current_maxima = MAX_AMPLITUDE = 0;
 minimum_time = 2 / SAMPLE_INTERVAL;
 maximum_time = 50 / SAMPLE_INTERVAL;
 end = index + length;

/*
  Begin processing and continue until end of window
*/ while (index < end) {

/*
  Find a minmum point
*/
```

```c
   while (array[index + 1] <= array[index])
      index++;
   current_minima = array[index];
   current_minima_position = index;
   time_between_peaks = current_minima_position - current_maxima_position;

/*
 Check time between this minima and current maxima for validity; increment
 count, total, and amplitude if highest so far
*/ if (time_between_peaks >= minimum_time &&
       time_between_peaks <= maximum_time) {
       temp = current_maxima - current_minima;
       peak_total += temp;
       peak_count++;
       if (temp > MAX_AMPLITUDE)
          MAX_AMPLITUDE = temp;
   }

/*
  Find a maximum point
*/ while (array[index + 1] >= array[index])
      index++;
   current_maxima = array[index];
   current_maxima_position = index;
   time_between_peaks = current_maxima_position - current_minima_position;

/*
 Check time between this maxima and current minima for validity; increment
 count, total, and amplitude if highest so far
*/ if (time_between_peaks >= minimum_time &&
       time_between_peaks <= maximum_time) {
       temp = current_maxima - current_minima;
       peak_total += temp;
       peak_count++;
       if (temp > MAX_AMPLITUDE)
          MAX_AMPLITUDE = temp;
   }
 }

/*
 Delete the peak amplitude from the total peak amplitude count
 and determine an average maximum peak amplitude.
*/ peak_total -= MAX_AMPLITUDE;
 if (peak_count-- <= 0)
   peak_count = 1;
 AVG_MAX_AMPLITUDE = (float) peak_total / (float) peak_count;
 if (MAX_AMPLITUDE <= 205)
   MAX_AMPLITUDE = (int) AVG_MAX_AMPLITUDE;
}

"C"
"68000"
$EXTENSIONS ON$
$ASM_FILE$
$FAR ON$
$CALL_ABS_LONG ON$
```

```
$LIB_ABS_LONG ON$
$INIT_ZEROES OFF$
$WARN OFF$
include "DEFINES"

extern short IN_SECOND_DELAY,PIR_DETECTED;

extern int REG_A,REG_B;
```

/********************/
/********************* SECOND DELAY **************************/
/********************/

```
/*
 Routine Name        : second_delay
 Parameters Passed   : sec -- delay time in seconds
 Parameters Returned : --
 Calling Routines    : halt, abort2, process, check_displays
 Routines Called     : --
 Local Variables     : i -- loop counter
*/ second_delay(sec)
int sec;
{ int i;

/*
 Start a 125 millisecond periodic interrupt and adjust the variable
 "sec" to 1/8 second delay cycles.
*/

IN_SECOND_DELAY = YES;
   sec *= 8;
   REG_A = PIR_125;
   PIR_DETECTED = NO;
   REG_B |= ENABLE_PIE;

/*
 Loop the proper number of delay cycles to meet the time criteria.
*/ for (i = 1; i <= sec; i++) {
      while (!PIR_DETECTED)
         ;
      PIR_DETECTED = NO;
   }

/*
Disable periodic interrupts.
*/

REG_B &= DISABLE_PIE;
   IN_SECOND_DELAY = NO;
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int REG_B,MAX_AMPLITUDE,TRIGGER_LEAD,ECG_STATUS_BUFFER,
           SECOND_BEST,LEAD1_AMP[],LEAD2_AMP[],LEAD3_AMP[];
```

```
extern unsigned int RAW_DATA_POSITION;

extern short LEADS_PROCESSED,LEAD_SELECTION_COMPLETE,ecg_control,
         LEAD1[],LEAD2[],LEAD3[],BAD[],table2[3];

extern unsigned short I,ECG_CONTROL;

extern float AVG_MAX_AMPLITUDE,LEAD1_SIGNAL_NOISE_RATIO,
         LEAD2_SIGNAL_NOISE_RATIO,LEAD3_SIGNAL_NOISE_RATIO;

/********************/
/************************  SELECT LEAD   ****************************/
                      /********************/

/*
  Routine Name        : select_lead
  Parameters Passed   : *progress_code -- progress code to signal where
                                          resumption of lead selection
                                          processing is to take place
                        *lead_monitoring -- current lead being monitored
                        *status -- signals a change in lead monitoring
  Parameters Returned :    --
  Calling Routines    : preprocess, abort3, standby_mode
  Routines Called     : search_max, monitor_lead
  Local Variables     : summation --  statistical summation array of how
                                      often leads 1,2,3 or a bad lead was
                                      selected as the trigger lead
                        n --  loop and index counter
*/ select_lead(progress_code,lead_monitoring,status)
short *progress_code,*lead_monitoring,*status;
{int summation[4],temp,order[4];
 short ordering,n;

/*
Determine if lead selection processing is needed.
*/ switch (*progress_code){

/*
Processing on the current lead is finished.  Disable data acquisition
and find lead with the largest amplitude.  Calculate individual average
signal-to-noise ratio's (SNR's).  Set up to monitor the next lead.
*/ case 1   : REG_B &= DISABLE_PIE;
                 LEADS_PROCESSED++;
                 search_max (LEAD1_AMP,(int) RAW_DATA_POSITION);
                 if (AVG_MAX_AMPLITUDE == 0.0)
                    AVG_MAX_AMPLITUDE = 1.0;
                 if (MAX_AMPLITUDE < 123)
                    LEAD1_SIGNAL_NOISE_RATIO = 0.0;
                 else
                    LEAD1_SIGNAL_NOISE_RATIO += (float) MAX_AMPLITUDE /
                                                       AVG_MAX_AMPLITUDE;
                 search_max (LEAD2_AMP,(int) RAW_DATA_POSITION);
                 if (AVG_MAX_AMPLITUDE == 0.0)
                    AVG_MAX_AMPLITUDE = 1.0;
                 if (MAX_AMPLITUDE < 123)
                    LEAD2_SIGNAL_NOISE_RATIO = 0.0;
                 else
                    LEAD2_SIGNAL_NOISE_RATIO += (float) MAX_AMPLITUDE /
                                                       AVG_MAX_AMPLITUDE;
                 search_max (LEAD3_AMP,(int) RAW_DATA_POSITION);
                 if (AVG_MAX_AMPLITUDE == 0.0)
```

```
                AVG_MAX_AMPLITUDE = 1.0;
             if (MAX_AMPLITUDE < 123)
                LEAD3_SIGNAL_NOISE_RATIO = 0.0;
             else
                LEAD3_SIGNAL_NOISE_RATIO += (float) MAX_AMPLITUDE /
                                                    AVG_MAX_AMPLITUDE;
             *lead_monitoring += 1;
             *progress_code = 0;
             *status = NO;
             return;

/*
Continue processing with current trigger lead selected.
*/ case  0 : switch (*lead_monitoring){

/*
Monitor all three leads.
*/ case 1 : *progress_code = monitor_lead(ECG_LEAD1,status);
                          return;
                 case 2 : *progress_code = monitor_lead(ECG_LEAD2,status);
                          return;
                 case 3 : *progress_code = monitor_lead(ECG_LEAD3,status);
                          return;
                 default :

/*
Initialize variables.
*/

LEAD1[I] = LEAD2[I] = LEAD3[I] = BAD[I] = 0;
                            LEAD1_SIGNAL_NOISE_RATIO /= LEADS_PROCESSED;
                            LEAD2_SIGNAL_NOISE_RATIO /= LEADS_PROCESSED;
                            LEAD3_SIGNAL_NOISE_RATIO /= LEADS_PROCESSED;
/*
Mark the summary table based on greatest average SNR.
*/
                            if ((ECG_STATUS_BUFFER & ECG_LEAD1_FLOATING) != 0)
                               LEAD1_SIGNAL_NOISE_RATIO = 0.0;
                            if ((ECG_STATUS_BUFFER & ECG_LEAD2_FLOATING) != 0)
                               LEAD2_SIGNAL_NOISE_RATIO = 0.0;
                            if ((ECG_STATUS_BUFFER & ECG_LEAD3_FLOATING) != 0)
                               LEAD3_SIGNAL_NOISE_RATIO = 0.0;
                            if ((((LEAD1_SIGNAL_NOISE_RATIO < 1.5) &&
                                  (LEAD2_SIGNAL_NOISE_RATIO < 1.5) &&
                                  (LEAD3_SIGNAL_NOISE_RATIO < 1.5)) ||
                                 ((ECG_STATUS_BUFFER & ECG_LEADS) == FLOATING)))
                               BAD[I] = 1;
                            else if ((LEAD1_SIGNAL_NOISE_RATIO >=
                                      LEAD2_SIGNAL_NOISE_RATIO) &&
                                     (LEAD1_SIGNAL_NOISE_RATIO >=
                                      LEAD3_SIGNAL_NOISE_RATIO))
                               LEAD1[I] = 1;
                            else if ((LEAD2_SIGNAL_NOISE_RATIO >=
                                      LEAD1_SIGNAL_NOISE_RATIO) &&
                                     (LEAD2_SIGNAL_NOISE_RATIO >=
                                      LEAD3_SIGNAL_NOISE_RATIO))
                               LEAD2[I] = 1;
                            else if ((LEAD3_SIGNAL_NOISE_RATIO >=
                                      LEAD1_SIGNAL_NOISE_RATIO) &&
                                     (LEAD3_SIGNAL_NOISE_RATIO >=
                                      LEAD2_SIGNAL_NOISE_RATIO))

LEAD3[I] = 1;
```

```
/*
Access weights (9,8,7, respectively) to the last three trigger leads selected
and sum.
*/
                        for (n = 0; n < 4; n++){
                          summation[n] = 0;
                          order[n] = n+1;
                        } for (n = 0; n < 3; n++){
                          summation[0] += LEAD1[n] * table2[n];
                          summation[1] += LEAD2[n] * table2[n];
                          summation[2] += LEAD3[n] * table2[n];
                          summation[3] += BAD[n] * table2[n];
                        }

/*
Lead selection is complete when one of the leads has been selected three
consecutive times as the trigger lead.
*/
                        LEAD_SELECTION_COMPLETE = NO;
                        if (summation[0] == 24 || summation[1] == 24 ||
                            summation[2] == 24)
                          LEAD_SELECTION_COMPLETE = YES;

/*
Determine a primary and secondary trigger lead using a bubble sort.
*/
                        ordering = YES;
                        while(ordering){
                          ordering = NO;
                          for (n = 0; n < 3; n++){
                            if (summation[n] < summation[n+1]){
                              temp = summation[n];
                              summation[n] = summation[n+1];
                              summation[n+1] = temp;

temp = order[n];
                              order[n] = order[n+1];
                              order[n+1] = temp;
                              ordering = YES;
                            }
                          }
                        } switch (order[0]){
                          case 1 : TRIGGER_LEAD = ECG_LEAD1;
                                   SECOND_BEST =
                                     (LEAD2_SIGNAL_NOISE_RATIO >
                                      LEAD3_SIGNAL_NOISE_RATIO ) ?
                                      ECG_LEAD2 : ECG_LEAD3;
                                   break;
                          case 2 : TRIGGER_LEAD = ECG_LEAD2;
                                   SECOND_BEST =
                                     (LEAD1_SIGNAL_NOISE_RATIO >
                                      LEAD3_SIGNAL_NOISE_RATIO ) ?
                                      ECG_LEAD1 : ECG_LEAD3;
                                   break;
                          case 3 : TRIGGER_LEAD = ECG_LEAD3;
                                   SECOND_BEST =
                                     (LEAD1_SIGNAL_NOISE_RATIO >
                                      LEAD2_SIGNAL_NOISE_RATIO ) ?
                                      ECG_LEAD1 : ECG_LEAD2;
                                   break;
                          case 4 : TRIGGER_LEAD = BAD_LEAD;
                        }
```

```
                        I = ++I % 3;
                        ECG_CONTROL = ecg_control &= FLOAT_RESET_LOW;
                        ECG_CONTROL = ecg_control != FLOAT_RESET_HIGH;

/*
 Start over with lead I.
*/
                        LEADS_PROCESSED = 0;
                        *lead_monitoring = 1;
                        *progress_code = 0;
                        *status = NO;
                        return;
                }
        }
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int IO_CONTROL,io_control,SWITCH_LED,switch_led;

extern unsigned int bleed_valve;

extern short FAILED_SELFTEST,MODE_IS_SELFTEST;

extern unsigned short BLEED_VALVE;

/********************/
/*************************   SELFTEST MODE   ****************************/
                        /********************/

/*
 Routine Name        :   selftest_mode
 Parameters Passed   :   --
 Parameters Returned :   --
 Calling Routines    :   main, standby_mode
 Routines Called     :   check_rom, check_ram, check_system,
                         check_real_time_clock, check_cuff_pressure,
                         check_displays
 Local Variables     :   temp -- temporary storage
                         old_LED_status -- stores LED state prior to
                                           selftest activity to restore
                                           after tests are completed.
*/
selftest_mode()
{int temp,old_LED_status;

MODE_IS_SELFTEST = YES;

/*
 Remember the current LED status.
*/ old_LED_status = switch_led;
 SWITCH_LED = switch_led &= SWITCH_LEDS_OFF;

/*
 Do not allow user to stop self-test activity.
*/
```

```
  SWITCH_LED = switch_led &= DISABLE_SS_INT;

/*
 Open the dump and bleed valves now to allow the pressure transducer to
 stabilize before testing.
*/

BLEED_VALVE = bleed_valve &= BLEED_VALVE_OPEN;
  IO_CONTROL = io_control &= DUMP VALVE OPEN;
/*
 Perform the self-tests.
*/

FAILED_SELFTEST = NO;
  check_rom();
  check_ram();
  check_system();
  check_displays();
  check_real_time_clock();
  check_cuff_pressure();

/*
 Restore the LED status.
*/

SWITCH_LED = switch_led = old_LED_status;
  MODE_IS_SELFTEST = NO;
)

"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int IO_CONTROL,io_control;

/*********************/
/************************    SET ATTEN    ****************************/
                        /*********************/

/*
 Routine Name         : set_atten
 Parameters Passed    : value -- attenuator value
 Parameters Returned  :
 Calling Routines     : adjust_atten
 Routines Called      : --
 Local Variables      : --
*/

/*
 This routine formats the attenuator value to BCD and loads it.
*/ set_atten(value)
int value;
(

/*
 If value is less than 10.0dB clear 10.0dB bit value.
 Otherwise, set that bit.
*/
```

```c
  if (value < 100)
     IO_CONTROL = io_control &= SET_ATTEN_0db;
  else{
     IO_CONTROL = io_control |= SET_ATTEN_10db;
     value -= 100;
  }

/*
 Determine 1.0dB and 0.1dB BCD values.
*/

IO_CONTROL = io_control &= HIGH_BYTE_MASK;
  IO_CONTROL = io_control |= ((value / 10)<<4) | (value % 10) & LOW_BYTE_MASK;
}
```

"68000"

```
;                         /********************/
;************************    SET_SR         ****************************/
;                         /********************/

;Routine Name        : set_sr
;Parameters Passed   : -2[A6] -- interrupt mask level to be set
;Parameters Returned :   --
;Calling Routines    : monitor_lead
;Routines Called     :   --
;Local Variables     : D0    -- temporary storage
;                      -2[A6] -- temporary storage PROG
          GLOBAL set_sr
set_sr
          LINK     A6,#-2
          CLR      -2[A6]           ;clear local variable space allocation
          MOVE     8[A6],D0         ;get interrupt mask
          MOVE     SR,-2[A6]        ;get current Status Register contents
          OR       D0,-2[A6]        ;mask interrupt with current Status Register
          MOVE     -2[A6],SR        ;replace Status Register with masked value
          UNLK     A6
          RTS
       END
```

"C"
"68000"
$EXTENSIONS ON$
$FAR ON$
$CALL_ABS_LONG ON$
$LIB_ABS_LONG ON$
$ASM_FILE$
$INIT_ZEROES OFF$
$WARN OFF$
include "DEFINES"

```c
extern int SYS_DISPLAY,SWITCH_LED,switch_led,REG_A,SECOND,
           SAMPLE_INDEX,REG_B,PRP_DISPLAY,ALARM_LED,alarm_led,
           SAMPLE_TIME;

extern short DIAGNOSTIC_SELFTEST,MODE_IS_PROGRAMM,PREVIOUS_ERROR_CONDITION,
             FAILED_SELFTEST,STATUS_OF_LEAD_SELECTION_PROCESSING,
             PROCESSING_LEAD_SELECTION,MODE_IS_REST,ecg_control,
             MODE_IS_STANDBY,MODE_IS_SELFTEST,MODE_IS_EXEC,ALARM_ON,
             EXEC_WAS_PREVIOUS_MODE,GOOD_REST_DATA,CLOCK_RUNNING,
             MODE_IS_MANUAL,MODE_TRANSITION,LEAD_STATUS,LEAD_PROGRESS,
             LEAD_MONITORING,LEAD_SELECTION_COMPLETE,MODE_IS_START,
             LEADS_PROCESSED,LEAD1[],LEAD2[],LEAD3[],BAD[],
             ERROR_CONDITION,SAMPLING_PI_DI,PI_DI_AMP_AVG_COMPLETE;
```

```
extern unsigned short ECG_CONTROL,HR_SWITCH;

extern float AVG_PI_AMP,AVG_DI_AMP;
```

```
                        /********************/
/************************    STANDBY_MODE    ******************************/
                        /********************/
```

```
/*
   Routine Name         :   standby_mode
   Parameters Passed    :   --
   Parameters Returned  :   --
   Calling Routines     :   main
   Routines Called      :   read_sw, display, stop, preprocess, select_lead,
                            manual_mode, programming_mode, selftest_mode
   Local Variables      :   temp -- temporary storage
                            condition --  current STBPM operation to
                                                perform
                            old_condition -- previous STBPM operation
                                                performed
                            selftest_timer -- time in seconds between
                                                depressions of the SELF TEST
                                                key
                            selftest_flag -- number of times the SELF TEST
                                                key is depressed within two
                                                seconds
                            start --  flag signaling the start of an STBPM
                                        operation
                            lead_selected -- flag signaling first time a
                                                lead was selected since last
                                                mode transition
                            new_mode -- flag signaling new mode transition
*/ standby_mode()
{
int temp;
static short old_condition;
short lead_selected,new_mode,selftest_timer,selftest_flag,
      start,condition,alarm_timer;
 new_mode = lead_selected = NO;
 old_condition = 0;
 SAMPLING_PI_DI = YES;
 REG_A = PIR_02;
 REG_B |= ENABLE_PIE;

for(;;){

/*
 Reset variables.
*/

MODE_IS_STANDBY = YES;
    start = NO;
    selftest_flag = 0;
    selftest_timer = 0;

/*
 Keep monitoring the status of all modes until a "start" condition is
 met.
*/ while (!start){
       condition = 0;
       read_sw();

/*
 The Self-test mode can be entered only if the operator depresses the
```

SELF TEST key three times in two seconds.
*/

```
      while (REG_A & UPDATE_CYCLE_IN_PROGRESS)
         ;
      temp = (SECOND & LOW_BYTE_MASK) - selftest_timer;
      if (temp < 0 )
         temp += 60;
      if (temp > 2 )
         selftest_flag = 0;
      if (MODE_IS_SELFTEST){
         if (selftest_flag == 0){
            while (REG_A & UPDATE_CYCLE_IN_PROGRESS)
              ;
            selftest_timer = SECOND & LOW_BYTE_MASK;
         }
         selftest_flag += 1;
         if (selftest_flag == 3){
            if (!DIAGNOSTIC_SELFTEST)
              display(&SYS_DISPLAY,"TESTSELF ",8,-2,8);
            start = YES;
            condition = 1;
         }
      }
/*
 Test for activation of the Programming mode.
*/ else if (MODE_IS_PROGRAM){
         condition = 2;
         start = YES;
      }
/*
 Test for selection of the Manual mode.
*/ else if (MODE_IS_MANUAL){
         if (!(FAILED_SELFTEST && !DIAGNOSTIC_SELFTEST)){
            condition = 3;
            if (!ERROR_CONDITION)
              display(&SYS_DISPLAY, "MAN. ", 4, -2, 12);
            SWITCH_LED = switch_led |= ENABLE_SS_INT;
         }
      }

/*
 Test for selection of the Rest mode.
*/ else if (MODE_IS_REST){
         condition = 4;
         if (EXEC_WAS_PREVIOUS_MODE){
            EXEC_WAS_PREVIOUS_MODE = GOOD_REST_DATA = NO;
         }
      }

/*
 Test for selection of the Exercise mode.  A Rest measurement must
 precede an Exercise cycle.
*/ else if (MODE_IS_EXEC){
         if (GOOD_REST_DATA)
            condition = 5;
         else if (!(FAILED_SELFTEST && !DIAGNOSTIC_SELFTEST)){
            display(&SYS_DISPLAY,"RESTFIRST",8,-2,8);
            SWITCH_LED  = switch_led &= DISABLE_SS_INT;
```

```
        }
    }

/*
Processing of the lead selection is lowest priority.
*/ if (PROCESSING_LEAD_SELECTION && !start)
           select_lead (&LEAD_PROGRESS,&LEAD_MONITORING,&LEAD_STATUS);

/*
Enable pi/di amplitude averaging.  It is activated here to ensure
that the sampling rate has been activated.  The ECG lead selection
activates a 2 millisecond sampling rate which is the rate for pi/
di amplitude averaging.  This must be activated in only one location.
*/

SAMPLING_PI_DI = YES;

if ((LEAD_SELECTION_COMPLETE && new_mode) ||
            (LEAD_SELECTION_COMPLETE && PREVIOUS_ERROR_CONDITION)){
          lead_selected = YES;
          new_mode = NO;
        }

/*
Clear the LED alarm states if:  (1) the elapsed time is not running,
(2) no previous error conditions are detected, and (3) the Manual
mode is not currently selected.
*/ if (!CLOCK_RUNNING && !ERROR_CONDITION && (condition != 3)){
          ALARM_LED = alarm_led &= ALARM_LEDS_OFF;

/*
The message "READY" is sent to the ELAPSED TIME display when a good ECG
lead has been selected.  Allow the STOP/RUN key to operate even if the
self-tests failed under the Diagnostic Self-test mode.
*/ if (lead_selected && !start && !MODE_IS_SELFTEST &&
             !(FAILED_SELFTEST && !DIAGNOSTIC_SELFTEST) &&
             !(MODE_IS_EXEC && !GOOD_REST_DATA) &&
             PI_DI_AMP_AVG_COMPLETE){
           if (HR_SWITCH & HR_SWITCH_ON)
             display (&SYS_DISPLAY,"  0   0   0 0.0READY",17,-1,0);
           else
             display (&SYS_DISPLAY,"  0   0    0.0READY",17,-1,0);
           SWITCH_LED = switch_led |= ENABLE_SS_INT;
          }
/*
Send blanks to the ELAPSED TIME display when no ECG trigger lead has
been selected.  Disable the STOP/RUN key, leaving the STBPM in the Stop
mode of operation.
*/ else if (!(FAILED_SELFTEST && !DIAGNOSTIC_SELFTEST) && !start
                  && !MODE_IS_SELFTEST && !(MODE_IS_EXEC && !GOOD_REST_DATA)){
            if (HR_SWITCH & HR_SWITCH_ON)
              display (&SYS_DISPLAY,"  0   0   0 0.0    ",17,-1,0);
            else
              display (&SYS_DISPLAY,"  0   0    0.0    ",17,-1,0);
            SWITCH_LED = switch_led &= DISABLE_SS_INT;
            stop();
          }
/*
Inform the user if the self-tests failed under the Non-diagnostic mode.
Disable the STOP/RUN key.
```

```
    */
            else if (!start && FAILED_SELFTEST && !DIAGNOSTIC_SELFTEST){
              display(&SYS_DISPLAY,"FAIL ",4,-2,12);
              SWITCH_LED = switch_led &= DISABLE_SS_INT;
            }
         }
/*
 Some error conditions (Arrhythmias, sys, dia and hr limit, etc.) sound
 the tone alarm.  Other error conditions (Check ECG, Check Cuff, Check
 Sys, etc.) do not sound the tone alarm and disable the processing to
 disable the tone alarm (Real-Time Clock AIE interrupts). The tone alarm
 is left on when two of these different error conditions occur at the same
 time.  This check allows the tone alarm to remain on for only one second
 when this situation occurs.
 */ if ((PREVIOUS_ERROR_CONDITION || ERROR_CONDITION) && ALARM_ON){
            while (REG_A & UPDATE_CYCLE_IN_PROGRESS)
               ;
            temp = (SECOND & LOW_BYTE_MASK) - alarm_timer;
            if (temp < 0 )
               temp += 60;
            if (temp > 1){
               ALARM_LED = alarm_led &= TONE_ALARM_OFF;
               ALARM_ON = NO;
            }
         }
         if (MODE_IS_START)
            start = YES;
         MODE_IS_SELFTEST = NO;
         MODE_IS_PROGRAM = NO;

/*
 Test for a mode transition.
 */ if (old_condition != condition){
            new_mode = YES;
            MODE_TRANSITION = YES;
            REG_B &= DISABLE_AIE;
            CLOCK_RUNNING = NO;
         }
         old_condition = condition;
      }

/*
 The start of a mode was activated.  Inhibit lead selection and averaging
 of the pi and di amplitudes.
 */

SAMPLING_PI_DI = NO;
      REG_B &= DISABLE_PIE;
      ECG_CONTROL = ecg_control &= DISABLE_ECG_INT;
      PROCESSING_LEAD_SELECTION = NO;
      MODE_IS_STANDBY = NO;

switch (condition){
         case 5 : preprocess();
                  EXEC_WAS_PREVIOUS_MODE = YES;
                  break;
         case 4 : preprocess();
                  break;
         case 3 : manual_mode();
                  break;
         case 2 : programming_mode();
                  break;
         case 1 : selftest_mode();
                  break;
```

}
    condition = 0;

/*
 Obtain time for alarm on check.
*/
        while (REG_A & UPDATE_CYCLE_IN_PROGRESS)
            ;
        alarm_timer = SECOND & LOW_BYTE_MASK;

/*
 Reset variables associated with pi and di ampTitude averaging.
*/

SAMPLE_TIME = SAMPLE_INDEX = 0;
    PI_DI_AMP_AVG_COMPLETE = NO;
/*
 Resume lead selection from the start if the user has not manually
 selected the trigger lead. Set the sampling rate for pi and di
 amplitude processing when lead selection is manually selected by the
 user. The sampling rate will be set by the lead selection routine
 if the user does not select the lead.
*/ if (STATUS_OF_LEAD_SELECTION_PROCESSING == YES){
       lead_selected = NO;
       PROCESSING_LEAD_SELECTION = YES;
       LEAD_SELECTION_COMPLETE = NO;
       LEADS_PROCESSED = LEAD_PROGRESS = LEAD_STATUS = 0;
       LEAD_MONITORING = 1;
       for (temp = 0; temp < 3; temp++)
          LEAD1[temp] = LEAD2[temp] = LEAD3[temp] = BAD[temp] = 0;
    }
    else{
       REG_A = PIR_02;
       REG_B |= ENABLE_PIE;
       SAMPLING_PI_DI = YES;
    }
"68000"
;                            /********************/
;**********************    START    **************************/
;                            /********************/

; Routine Name         :   start
; Parameters Passed    :   --
; Parameters Returned  :   --
; Calling Routines     :   reset/power-up of STBPM
; Routines Called      :   main
; Local Variables      :   --

EXTERNAL    main
        GLOBAL      start

PROG start   MOVEA.L    #0H,A6
        JMP        main

END
"C"
"68000"
$EXTENSIONS ON$
$ASM_FILE$
$FAR ON$
$WARN OFF$

```
$INIT_ZEROES OFF$
$CALL_ABS_LONG ON$
$LIB_ABS_LONG ON$
#include "DEFINES"

extern short MODE_IS_STOP,MODE_IS_START;

extern int SWITCH_LED,switch_led;
```

/********************/
/**********************  STOP   **************************/
/********************/

```
/*
 Routine Name         : stop
 Parameters Passed    : --
 Parameters Returned  : --
 Calling Routines     : manual_mode, stop_start_interrupt, pump, abort2,
                        real_time_interrupt, preprocess, standby_mode
 Routines Called      : --
 Local Variables      : --
*/ stop()
{

/*
 Change states from RUN to STOP.
*/

MODE_IS_STOP = YES;
  SWITCH_LED = switch_led |= STOP_LED_ON;
  MODE_IS_START = NO;
  SWITCH_LED = switch_led &= START_LED_OFF;
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"
```

/********************/
/**********************  TWO COMPLEMENT  **************************/
/********************/

```
/*
 Routine Name         : two_complement
 Parameters Passed    : data -- 12 bit result from A/D
 Parameters Returned  : two's complement of "data"
 Calling Routines     : real_time_interrupt
 Routines Called      : --
 Local Variables      : --
*/ two_complement(data)
int data;
{

/*
 Mask off upper four bits and return positive representation of data if
 data bit 16 of the A/D converted data is set. Otherwise, extend negative
 sign and return data.
```

```
  if (data & AD_DATA_SIGN_BIT)
     return(data & AD_DATA_POSITIVE_MASK);
  else
     return(data | AD_DATA_NEGATIVE_MASK);
}
"C"
"68000"
$EXTENSIONS ON$
$ASM_FILE$
$FAR ON$
$WARN OFF$
$INIT_ZEROES OFF$
$CALL_ABS_LONG ON$
$LIB_ABS_LONG ON$
#include "DEFINES"

extern int REG_A,REG_B,MONTH,YEAR,DATE,SECOND;

#define january 01
#define february 02
#define march 03
#define april 04
#define may 05
#define june 06
#define july 07
#define august 8
#define september 9
#define october 10
#define november 11
#define december 12
```

/*********************/
/*********************** VALIDATE ***************************/
/*********************/

```
/*
Routine Name         : validate
Parameters Passed    : value -- Real-Time Clock value to be validated
                       max -- maximum limitation of value to be validated
                       min -- minimum limitation of value to be validated
                       setting -- current setting of the programmable
                                  timer at time of routine call
Parameters Returned  : max_date -- maximum date value to be displayed
Calling Routines     : programming_mode, check_real_time_clock, validate
Routines Called      : validate
Local Variables      : max_date -- maximum date value for current month
                                   setting
                       temp -- temporary storage
                       month_value -- current Real-Time Clock value for the
                                      MONTH setting at time of routine call
                       year_value -- current Real-Time Clock value for the
                                     YEAR setting at time of routine call
*/ validate(value,max,min,setting)
short max,min;
int *value,setting;
{int max_date,temp;
 short month_value,year_value;

/*
 Get value from the Real-Time Clock.
*/
```

```
while (REG_A & UPDATE_CYCLE_IN_PROGRESS)
   ;
temp = *value & LOW_BYTE_MASK;
/*
 For DAY 12 position switch setting, validate MONTH and YEAR and use them to
 determine valid DAY settings.  If DAY is invalid, set it to 1.  In all
 cases determine the maximum valid DAY and return this value.
*/ if (setting == date){
    validate (&MONTH,12,1,month);
    validate (&YEAR,99,YEAR_SETTING,year);
    while (REG_A & UPDATE_CYCLE_IN_PROGRESS)
       ;
    month_value = MONTH & LOW_BYTE_MASK;
    year_value = YEAR & LOW_BYTE_MASK;
    switch(month_value){
      case february  : if (year_value % 4 == 0 && year_value % 100 != 0 ||
                           year_value % 400 == 0)
                         max_date = 29;
                       else
                         max_date = 28;
                       break;
      case april     :
      case june      :
      case september :
      case november  : max_date = 30;
                       break;
      case january   :
      case march     :
      case may       :
      case july      :
      case august    :
      case october   :
      case december  : max_date = 31;
                       break;
    }
    if (temp > max_date || temp < 1){
      while (REG_A & UPDATE_CYCLE_IN_PROGRESS)
         ;
      REG_B |= STOP_UPDATE_CYCLE;
      DATE = 1;
      REG_B &= RESUME_UPDATE_CYCLE;
    }
    return(max_date);
  }

/*
 For invalid MONTH, YEAR, HOUR  and MINUTE data, set values to minimal data.
 Set the Real-Time Clock Seconds value to zero when the setting is MINUTE
 or HOUR.
*/ else if (temp < min || temp > max){
    *value = min;
    if (setting == hour || setting == minute){
      while (REG_A & UPDATE_CYCLE_IN_PROGRESS)
         ;
      REG_B |= STOP_UPDATE_CYCLE;
      SECOND = 00H;
      REG_B &= RESUME_UPDATE_CYCLE;
    }
  }
}
"68000"

;                          /********************/
;**************************      ZINVALID      ********************************/
;                          /********************/
```

```
; Routine Name       : Zinvalid
; Parameters Passed  :   --
; Parameters Returned :  --
; Routines Called    :   --
; Local Variables    :   --

GLOBAL Zinvalid

PROG

Zinvalid
        RTS

END
"C"
"68000"
$ASM_FILE$
$WARN OFF$
$EXTENSIONS ON$
$FAR ON$
$CALL_ABS_LONG ON$
$LIB_ABS_LONG ON$
$INIT_ZEROES OFF$
$INTERRUPT ON$

/********************/
/************************  ACIA INTERRUPT  ****************************/
                    /********************/

/*
 Routine Name       : acia_interrupt
 Parameters Passed  :   --
 Parameters Returned :  --
 Calling Routines   : level 2 interrupt
 Routines Called    :   --
 Local Variables    :   --
*/ acia_interrupt()
()

$INTERRUPT OFF$
"C"
"68000"
$ASM_FILE$
$WARN OFF$
$EXTENSIONS ON$
$FAR ON$
$CALL_ABS_LONG ON$
$LIB_ABS_LONG ON$
$INIT_ZEROES OFF$
#include "DEFINES"

extern int bleed(),display();
extern long Zlongreal_round();

extern unsigned long HR_COUNT,ECG_PULSE_COUNT,PREVIOUS_INT_TIME,
                CURRENT_INT_TIME;
extern unsigned int bleed_valve;
extern int ECG_STATUS_BUFFER,REG_A,REG_B,SEC_COUNT,ECG[],SIZE,
        HR_DISPLAY,LAST_CUFF_PRESSURE,CUFFP_OFFSET,
        ALARM_LED,alarm_led;
extern unsigned int RAW_DATA_POSITION;
extern short MODE_IS_START,MODE_IS_EXEC,MODE_IS_REST,FIRST_ECG,
        AVERAGE_HR_DISPLAYED,ecg_control,DATA_OK,ALARM_ON,
        BLEED_PROCESS_FINISHED,ARRHYTHMIA;
``` extern unsigned short BLEED_VALVE,ECG_CONTROL,HR_SWITCH;

$INTERRUPT ON$

/********************/
/*********************** ECG INTERRUPT **************************/
/********************/

```
/*
 Routine Name        : ecg_interrupt
 Parameters Passed   : --
 Parameters Returned : --
 Calling Routines    : level 4 interrupt
 Routines Called     : bleed, display
 Local Variables     : time1 -- array of time between pulses used for
                                the running six pulse intermediate heart
                                rate calculation
                       time2 -- array of time between pulses used for
                                the running three pulse arrhythmia
                                calculation
                       last_pulse_time -- previous time between pulses
                       current_pulse_time -- a running three pulse count
                                             of time between pulses
                       intermediate_hr -- a running six pulse count of
                                          time between pulses
                       temp -- temporary storage
                       time_between_pulses --  delay time between ECG
                                               triggers
                       i -- index
                       j -- index
                       dtemp -- double precision temporary storage
                       deviate75 -- -25 percent of last time between pulses
                       deviate125 -- +25 percent of last time between pulses
                       flast_pulse_time -- last time between pulses in
                                           single precision
                       fcurrent_pulse_time -- current time between pulses
                                              in single precision
*/
ecg_interrupt()
{static int time1[PULSE_SAMPLE],time2[HR_SAMPLE],last_pulse_time,
            current_pulse_time,intermediate_hr;
 int temp;
 unsigned int time_between_pulses;
 short i,j;
 double dtemp;
 float deviate75,deviate125,half_pulse_time,flast_pulse_time,
       fcurrent_pulse_time;

/*
 Test for a valid ECG interrupt.
*/ if (!(ECG_STATUS_BUFFER & ECG_INTERRUPT_PENDING)){

/*
 Service ECG interrupt only if processing the Rest or Exercise mode.
*/ if (MODE_IS_START && (MODE_IS_EXEC || MODE_IS_REST)){

/*
 Mark the ECG.
*/

ECG[RAW_DATA_POSITION % SIZE] = 1;

/*
 Reinitialize all variables on the first ECG of every new measurement
 cycle.
```

```
    if (FIRST_ECG){
      FIRST_ECG = NO;
      CURRENT_INT_TIME = PREVIOUS_INT_TIME = HR_COUNT = ECG_PULSE_COUNT = 0;
      SEC_COUNT = intermediate_hr = last_pulse_time = current_pulse_time = 0;
      for (temp = 0; temp <= PULSE_SAMPLE; temp++)
        time1[temp] = time2[temp] = time2[temp+PULSE_SAMPLE] = 0;
      ECG_CONTROL = ecg_control &= DISABLE_ECG_INT;
      ECG_CONTROL = ecg_control |= ENABLE_ECG_INT;
      bleed(CURRENT_INT_TIME);
      return;
    }

/*
 Do arrhythmia detection, and calculate and display the intermediate heart
 rate from the start of a measurement until the bleed process is finished.
*/ if (!BLEED_PROCESS_FINISHED){

/*
 Determine index values for the running pulse rate and intermediate heart
 rate time counts.
*/ i = ECG_PULSE_COUNT % PULSE_SAMPLE;
       j = ECG_PULSE_COUNT % HR_SAMPLE;

/*
 Perform running time counts for pulse rate and intermediate heart rate.
*/ time_between_pulses = CURRENT_INT_TIME - PREVIOUS_INT_TIME;
       PREVIOUS_INT_TIME = CURRENT_INT_TIME;
       if (ECG_PULSE_COUNT < 3){
          current_pulse_time += time1[i] = time_between_pulses;
          last_pulse_time = current_pulse_time;
       }
       else{
          current_pulse_time -= time1 [i];
          current_pulse_time += time1 [i] = time_between_pulses;
       }
       if (ECG_PULSE_COUNT < 6)
          intermediate_hr += time2 [j] = time_between_pulses;
       else{
          intermediate_hr -= time2 [j];
          intermediate_hr += time2 [j] = time_between_pulses;
       }

/*
 Do arrhythmia detection on a running three pulse time interval.
*/

ARRHYTHMIA = NO;
       if (ECG_PULSE_COUNT >= PULSE_SAMPLE){
          flast_pulse_time = (float) last_pulse_time;
          fcurrent_pulse_time = (float) current_pulse_time;

/*
 An arrhythmia has occurred when the current running three pulse time
 deviates by +- 25 percent from the last running three pulse time.
 Sound the tone alarm for one second and turn on the ARRHYTHMIA LED alarm.
*/ if ((deviate75 = flast_pulse_time * .75) >= fcurrent_pulse_time ||
              fcurrent_pulse_time >= (deviate125 = flast_pulse_time * 1.25)){
```

```
              ALARM_LED = alarm_led |= (ARR_LED_ON | TONE_ALARM_ON);
              ARRHYTHMIA = ALARM_ON = YES;
            }
            last_pulse_time = current_pulse_time;
          }

/*
Bleed and increment the Heart Rate count if no arrhythmia occurred.
*/
          if (!ARRHYTHMIA){
            bleed (time_between_pulses);
            HR_COUNT++;
          }
/*
Display the intermediate heart rate every two seconds until the final
Heart Rate is displayed at the end of a measurement. The intermediate
Heart Rate is a running average of the last six pulse interval times
which do include arrhythmias.
*/ if (ECG_PULSE_COUNT++ >= HR_SAMPLE - 1 &&
              !AVERAGE_HR_DISPLAYED && SEC_COUNT >= 1){
            if ((dtemp = (double) intermediate_hr * (double) 0.976625) <= 0)
              dtemp = 1;
            if (HR_SWITCH & HR_SWITCH_ON){
              temp = Zlongreal_round(360000.0 / dtemp);
              if (temp > 300)
                temp = 999;
              display(&HR_DISPLAY,"",0,temp,2);
            }
            else
              display(&HR_DISPLAY,"",0,-2,2);
            SEC_COUNT = 0;
          }
        }
      }
    }

/*
Reset whether or not a valid interrupt occurred.
*/

ECG_CONTROL = ecg_control &= DISABLE_ECG_INT;
  ECG_CONTROL = ecg_control |= ENABLE_ECG_INT;
}

$INTERRUPT OFF$
"C"
"68000"
$ASM_FILE$
$WARN OFF$
$EXTENSIONS ON$
$FAR ON$
$CALL_ABS_LONG ON$
$LIB_ABS_LONG ON$
$INIT_ZEROES OFF$
$INTERRUPT ON$

/********************/
/************************ GPIA INTERRUPT ***************************/
                        /********************/

/*
Routine Name       : gpia_interrupt
Parameters Passed  : --
Parameters Returned : --
```

```
  Calling Routines      : level 1 interrupt
  Routines Called       : --
  Local Variables       : --
*/ gpia_interrupt()
()

$INTERRUPT OFF$

"C"
"68000"
$ASM_FILE$
$WARN OFF$
$EXTENSIONS ON$
$FAR ON$
$CALL_ABS_LONG ON$
$LIB_ABS_LONG ON$
$INIT_ZEROES OFF$
$INTERRUPT ON$
```

```
                    /********************************/
/************************ PROGRAMMABLE TIMER INTERRUPT ***************/
                    /********************************/

/*
  Routine Name          : programmable_timer_interrupt
  Parameters Passed     : --
  Parameters Returned   : --
  Calling Routines      : level 3 interrupt
  Routines Called       : --
  Local Variables       : --
*/ programmable_timer_interrupt()
()

$INTERRUPT OFF$
"C"
"68000"
$ASM_FILE$
$WARN OFF$
$EXTENSIONS ON$
$FAR ON$
$CALL_ABS_LONG ON$
$LIB_ABS_LONG ON$
$INIT_ZEROES OFF$
#include "DEFINES"

extern int abort2(),stop(),acquire_data(),display(),search_max(),
          two_complement();

extern unsigned long CURRENT_INT_TIME,PREVIOUS_INT_TIME;

extern int REG_B,REG_C,LEAD1_AMP[],LEAD2_AMP[],LEAD3_AMP[],PROX[],DIST[],
          CUFF[],SIZE,CUFFP_OFFSET,ALARM_LED,PRP_DISPLAY,SEC_COUNT,
          IO_CONTROL,io_control,TRIGGER_LEAD,ECG_STATUS_BUFFER,
          REG_A,INTERVAL_END,alarm_led,SAMPLE_INDEX,SAMPLE_TIME,
          PI_COUNT,DI_COUNT,
          PI_AMP[],DI_AMP[],ELAPSED_DISPLAY,ELAPSED_TIME;

extern unsigned int bleed_valve, RAW_DATA_POSITION;

extern short IN_CAL_CUFFP,IN_PUMP,IN_SECOND_DELAY,SHOW_TIME,
          PIR_DETECTED,PROCESSING_LEAD_SELECTION,DELAY,DELAY_TIME,
```

```
       DATA_OK,MODE_IS_START,MODE_IS_REST,MODE_IS_EXEC,ABORT2,
       BLEED_PROCESS_FINISHED,DATASET_COMPLETE,SAMPLING_PI_DI,
       ALARM_ON,ABORT3,ELAPSED_SEC1,ELAPSED_SEC2,ELAPSED_MIN1,
       ELAPSED_MIN2,ecg_control,INTERVAL_UP,ARRHYTHMIA,
       CLOCK_RUNNING,ERROR_CONDITION,PI_DI_AMP_AVG_COMPLETE,
       NO_ECG_FOUND,FIRST_TIME,MEASUREMENT_COMPLETE;

extern unsigned short ECG_CONTROL,BLEED_VALVE;

extern float AVG_MAX_AMPLITUDE,AVG_PI_AMP,AVG_DI_AMP,
             SUM_PI_AMP,SUM_DI_AMP,AVG_PI_ARRAY[],AVG_DI_ARRAY[];

$INTERRUPT ON$

/******************************/
/************************ REAL TIME CLOCK INTERRUPT ************************/
                    /******************************/

/*
  Routine Name         : real_time_clock_interrupt
  Parameters Passed    :  --
  Parameters Returned  :  --
  Calling Routines     : level 5 interrupt
  Routines Called      : acquire_data, display, stop
  Local Variables      : temp -- temporary storage
                         i -- loop counter and index
                         *elapsed_display -- elapsed display address
                         reg_b -- equivalent to the global variable REG_B of
                                  the Real-Time Clock.
                         reg_c -- equivalent to the global variable REG_C of
                                  the Real-Time Clock.
*/ real_time_clock_interrupt()
{int temp,i;
 int reg_c,reg_b,*elapsed_display;
 char saturated;

/*
  Reset and store all register flags.
*/ reg_c = REG_C;
 reg_b = REG_B;

/*
  Test for valid Real-Time Clock Interrupt.
*/ if ((reg_c & REAL_TIME_CLOCK_INT_PENDING)==0)
   return;

/*
  Test for a periodic interrupt.
*/ if ((reg_c & PF_MASK) && (reg_b & PIE_MASK)){

/*
  Periodic interrupt was caused by the "preprocess" routine to allow
  sampling of the pi and di channels in between measurement cycles to
  determine average pi and di amplitudes.
*/ if (SAMPLING_PI_DI && (SAMPLE_INDEX <= 500)){
      PI_AMP[SAMPLE_INDEX] = DI_AMP[SAMPLE_INDEX] = 0;
      temp = two_complement(acquire_data(PROXIMAL_SENSOR));
```

```
      if (DATA_OK)
        PI_AMP[SAMPLE_INDEX] = temp;
      temp = two_complement(acquire_data(DISTAL_SENSOR));
      if (DATA_OK)
        DI_AMP[SAMPLE_INDEX] = temp;
      SAMPLE_INDEX++;
      if ((SAMPLE_TIME+=2) == ONE_SEC){
        search_max(PI_AMP,SAMPLE_INDEX);
        if (AVG_MAX_AMPLITUDE > 50.0)
          AVG_MAX_AMPLITUDE = 50.0;
        SUM_PI_AMP -= AVG_PI_ARRAY[i = PI_COUNT % 10];
        SUM_PI_AMP += AVG_PI_ARRAY[i] = AVG_MAX_AMPLITUDE;
        PI_COUNT++;
        if (PI_COUNT >= 20)
          PI_COUNT = 10;
        if (PI_COUNT < 10)
          AVG_PI_AMP = SUM_PI_AMP / PI_COUNT;
        else
          AVG_PI_AMP = SUM_PI_AMP / 10.0;

search_max(DI_AMP,SAMPLE_INDEX);
        if (AVG_MAX_AMPLITUDE > 50.0)
          AVG_MAX_AMPLITUDE = 50.0;
        SUM_DI_AMP -= AVG_DI_ARRAY[i = DI_COUNT % 10];
        SUM_DI_AMP += AVG_DI_ARRAY[i] = AVG_MAX_AMPLITUDE;
        DI_COUNT++;
        if (DI_COUNT >= 20)
          DI_COUNT = 10;
        if (DI_COUNT < 10)
          AVG_DI_AMP = SUM_DI_AMP / DI_COUNT;
        else
          AVG_DI_AMP = SUM_DI_AMP / 10.0;

SAMPLE_TIME = SAMPLE_INDEX = 0;
        PI_DI_AMP_AVG_COMPLETE = YES;
      }
    }
/*
Periodic interrupt was caused by "select_lead" routine.
*/ if (PROCESSING_LEAD_SELECTION){

/*
Delay 50 milliseconds to miss ECG triggers caused by lead switching.
*/ if (DELAY && (DELAY_TIME++ == 25)){
        DELAY = NO;
        DELAY_TIME = 0;
        return;
      }

/*
Sample and store data on raw ECG lead multiplexer channels.
*/ if (RAW_DATA_POSITION <= 1000){
        temp = two_complement(acquire_data(ECG_LEAD1_RAW));
        if (DATA_OK)
          LEAD1_AMP[RAW_DATA_POSITION] = temp;
        temp = two_complement(acquire_data(ECG_LEAD2_RAW));
        if (DATA_OK)
          LEAD2_AMP[RAW_DATA_POSITION] = temp;
        temp = two_complement(acquire_data(ECG_LEAD3_RAW));
        if (DATA_OK)
          LEAD3_AMP[RAW_DATA_POSITION] = temp;
```

```
         RAW_DATA_POSITION++;
      }
   }

/*
 Periodic interrupt was caused by either the "cal_cuffp", "pump", or
 "second_delay" routine.  Set the periodic interrupt detected flag.
*/ else if (IN_CAL_CUFFP || IN_PUMP || IN_SECOND_DELAY)
      PIR_DETECTED = YES;

/*
 Periodic interrupt was caused by the Rest or Exercise modes.
*/ else if (MODE_IS_START && (MODE_IS_REST || MODE_IS_EXEC)){

/*
 If the cuff is still undergoing depressurization, increment
 the total time for current measurement.  Sample and store the
 proximal, distal, and cuff pressure data.
*/ if (!BLEED_PROCESS_FINISHED){
         CURRENT_INT_TIME += 2;
         if (!DATASET_COMPLETE){
            temp = two_complement(acquire_data(PROXIMAL_SENSOR));
            if (DATA_OK)
               PROX[RAW_DATA_POSITION % SIZE] = temp;
            temp = two_complement(acquire_data(DISTAL_SENSOR));
            if (DATA_OK)
               DIST[RAW_DATA_POSITION % SIZE] = temp;
            temp = acquire_data(CUFF_PRESSURE) - CUFFP_OFFSET;
            if (DATA_OK)
               CUFF[RAW_DATA_POSITION % SIZE] = temp;
            RAW_DATA_POSITION++;
         }
      }
   }
}

/*
 Test for alarm interrupt.
*/ if ((reg_c & AF_MASK) && (reg_b & AIE_MASK)){

/*
 The Rest or Exercise mode generated a one second interrupt to update
 the ELAPSED TIME display.
*/ if (MODE_IS_REST || MODE_IS_EXEC){

/*
 Turn off tone alarm if it is on.
*/ if (ALARM_ON){
          ALARM_LED = alarm_led &= TONE_ALARM_OFF;
          ALARM_ON = NO;

/*
 If the "abort3" routine was activated then disable updates to the
 ELAPSED TIME display and inform user.
```

```
      if (ABORT3)<
        ABORT3 = NO;
        REG_B &= DISABLE_AIE;
        CLOCK_RUNNING = NO;
        ERROR_CONDITION = YES;
        display(&PRP_DISPLAY,"ECG CHECK",8,-1,0);
        return;
      >
    >

/*
 Update the ELAPSED TIME display.  Maximum time displayed is 99:99.
 If time becomes greater than 99:99, the assumption is made that the
 most current STBPM cycle was not terminated.  Processing then
 resumes to the Standby mode once the LED's, dump valve, interrupts,
 etc. are deactivated.
*/

SEC_COUNT+=1;
    if ((ELAPSED_SEC2+=1) > 9)<
      ELAPSED_SEC2 = 0;
      if ((ELAPSED_SEC1+=1) > 5)<
        ELAPSED_SEC1 = 0;
        if ((ELAPSED_MIN2+=1) > 9)<
          ELAPSED_MIN2 = 0;
          if ((ELAPSED_MIN1+=1) > 9)<
            ELAPSED_MIN1 = 0;
            IO_CONTROL = io_control |= PUMP_OFF;
            IO_CONTROL = io_control &= DUMP_VALVE_OPEN;
            BLEED_VALVE = bleed_valve &= BLEED_VALVE_OPEN;
            ECG_CONTROL = ecg_control &= DISABLE_ECG_INT;
            REG_B &= (DISABLE_AIE && DISABLE_PIE);
            CLOCK_RUNNING = NO;
            REG_A &= DISABLE_PIR;
            stop();
          >
        >
      >
    >

/*
 Update the displays if it is proper to do so.
*/
    if (SHOW_TIME) <
      elapsed_display = &ELAPSED_DISPLAY;
      if (ELAPSED_MIN1 == 0)
        *elapsed_display++ = BLANK;
      else
        *elapsed_display++ = ELAPSED_MIN1 | ASCII_MASK;
      *elapsed_display++ = ELAPSED_MIN2 | ASCII_MASK;
      *elapsed_display++ = COLON;
      *elapsed_display++ = ELAPSED_SEC1 | ASCII_MASK;
      *elapsed_display = ELAPSED_SEC2 | ASCII_MASK;
    >

ELAPSED_TIME = (((ELAPSED_MIN1 * 1000) + (ELAPSED_MIN2 * 100))+
                    (ELAPSED_SEC1 * 10)) + ELAPSED_SEC2;

/*
 Check for end of measurement cycle interval.  Do not allow a new
 interval to begin if the current measurement cycle is not finished.
*/ if (ELAPSED_TIME >= INTERVAL_END)<
      INTERVAL_UP = YES;
```

```
          if ((MODE_IS_REST || MODE_IS_EXEC) && !MEASUREMENT_COMPLETE)
            INTERVAL_UP = NO;
      }

/*
 Set the appropriate flag to inform the "process" routine when an ECG has
 not occurred for 2 seconds.  Call the "abort2" routine to select the
 second best lead choice and restart the measurement cycle when no ECG
 has been detected for five seconds.
*/
      if (MODE_IS_START){
        if (((temp = CURRENT_INT_TIME - PREVIOUS_INT_TIME) >= TWO_SEC)
            && !BLEED_PROCESS_FINISHED){
          NO_ECG_FOUND = YES;
          if (temp >= FIVE_SEC){
            abort2();
            return;
          }
        }

/*
 Sample raw ECG lead data for saturation every second.  The current trigger
 lead is no longer valid when saturation is found on all three channels.
 Call the "abort2" routine to select the second best lead choice and restart
 the measurement cycle.
*/ saturated = FALSE;
        if ((acquire_data(ECG_LEAD1_PEAK) > 4080) &&
            (acquire_data(ECG_LEAD2_PEAK) > 4080) &&
            (acquire_data(ECG_LEAD3_PEAK) > 4080))
          saturated = TRUE;

if (!BLEED_PROCESS_FINISHED && ((saturated && ARRHYTHMIA) ||
            ((TRIGGER_LEAD == ECG_LEAD1) &&
             (ECG_STATUS_BUFFER & ECG_LEAD1_FLOATING == YES)) ||
            ((TRIGGER_LEAD == ECG_LEAD2) &&
             (ECG_STATUS_BUFFER & ECG_LEAD2_FLOATING == YES)) ||
            ((TRIGGER_LEAD == ECG_LEAD3) &&
             (ECG_STATUS_BUFFER & ECG_LEAD3_FLOATING == YES))))
          abort2();
      }
    }
  }
}

$INTERRUPT OFF$

"68000"
        GLOBAL  cr_lf
        GLOBAL  table1
        GLOBAL  table2
        GLOBAL  t_values

PROG cr_lf    DC.B   13, 10                          ;USED IN OUTPUT TO RS232
         EVEN table1   DC.L   1,10,100,1000,10000             ;Used in "display"
         EVEN table2   DC.B   7,8,9                           ;Used in "select_lead"
         EVEN t_values REAL   12.706, 4.303, 3.182, 2.776, 2.571   ;Used in "process"
         REAL   2.447, 2.365, 2.306, 2.262, 2.228
```

```
              REAL    2.201, 2.179, 2.160, 2.145, 2.131
              REAL    2.120, 2.110, 2.101, 2.093, 2.086
              REAL    2.080, 2.074, 2.069, 2.064, 2.060
              REAL    2.056, 2.052, 2.048, 2.045, 1.960

END
"C"
"68000"
$ASM_FILE$
$WARN OFF$
$EXTENSIONS ON$
$FAR ON$
$CALL_ABS_LONG ON$
$LIB_ABS_LONG ON$
$INIT_ZEROES OFF$
#include "DEFINES"

extern int stop();

extern unsigned int bleed_valve;

extern int SWITCH_LED,switch_led,IO_CONTROL,io_control,SWITCH_BUFFER;

extern short MODE_IS_STOP,MODE_IS_START,MODE_IS_MANUAL,MODE_IS_MODIFY,
             SAMPLING_PI_DI,ERROR_CONDITION,PREVIOUS_ERROR_CONDITION;

extern unsigned short SS_INT_STATUS,BLEED_VALVE;

$INTERRUPT ON$

/*************************/
/************************* STOP START INTERRUPT *************************/
                        /*************************/

/*
 Routine Name        : stop_start_interrupt
 Parameters Passed   : --
 Parameters Returned : --
 Calling Routines    : level 6 interrupt
 Routines Called     : stop
 Local Variables     : --
*/ stop_start_interrupt()
{

/*
 Disable STOP/RUN interrupt key and service valid STOP/RUN interrupts.
*/ if ((SS_INT_STATUS & SS_INT_PENDING) == 0)
    return;
  SWITCH_LED = switch_led &= DISABLE_SS_INT;

if (ERROR_CONDITION){
    PREVIOUS_ERROR_CONDITION = YES;
    ERROR_CONDITION = NO;
  }

/*
 Last state was STOP so change to RUN.
*/ if (MODE_IS_STOP){
    MODE_IS_START = YES;
    SWITCH_LED = switch_led |= START_LED_ON;
    MODE_IS_STOP = NO;
    SWITCH_LED = switch_led &= STOP_LED_OFF;
```

```
    if (MODE_IS_MANUAL && !(SWITCH_BUFFER & MODIFY_DEPRESSED))
      MODE_IS_MODIFY = YES;
}
/*
Last state was RUN so change to STOP.  Disable pump and open the
dump and bleed valves.
*/ else if (MODE_IS_START){
   SAMPLING_PI_DI = NO;
   IO_CONTROL = io_control |= PUMP_OFF;
   IO_CONTROL = io_control &= DUMP_VALVE_OPEN;
   BLEED_VALVE = bleed_valve &= BLEED_VALVE_OPEN;
   stop();
 }

/*
Reenable STOP/RUN key interrupts.
*/

SWITCH_LED = switch_led  |= ENABLE_SS_INT;
}

$INTERRUPT OFF$
"68000"

; Exception processing is handled here.  The microprocessor resumes
; normal instruction decoding at the given memory address of the
; exception vector.  A symbol is placed in the first systolic display
; address.  All further execution remains in a tight loop.

PROG
     GLOBAL BUS_ERROR,ADDR_ERROR,INSTR_ERROR,DIV_ERROR,OVFL_ERROR,PRIV_ERROR
     GLOBAL TRAPV_ERROR,TRACE_ACT,EM_1010.EM_1111,RES_1,RES_2,RES_3

BUS_ERROR
       MOVE      #22H,44020H        ; display A """
       BRA       LOOP
ADDR_ERROR
       MOVE      #23H,44020H        ; display A "#"
       BRA       LOOP
INSTR_ERROR
       MOVE      #24H,44020H        ; display A "$"
       BRA       LOOP
DIV_ERROR
       MOVE      #25H,44020H        ; display A "%"
       BRA       LOOP
OVFL_ERROR
       MOVE      #26H,44020H        ; display A "&"
       BRA       LOOP
TRAPV_ERROR
       MOVE      #2BH,44020H        ; display A "+"
       BRA       LOOP
PRIV_ERROR
       MOVE      #27H,44020H        ; display A "'"
       BRA       LOOP
TRACE_ACT
       MOVE      #28H,44020H        ; display A "("
       BRA       LOOP
EM_1010
       MOVE      #29H,44020H        ; display A ")"
       BRA       LOOP
EM_1111
       MOVE      #2AH,44020H        ; display A "*"
       BRA       LOOP
```

```
RES_1
        MOVE        #2CH,44020H         ; display A ","
        BRA         LOOP
RES_2
        MOVE        #2DH,44020H         ; display A "-"
        BRA         LOOP
RES_3
        MOVE        #2EH,44020H         ; display A "."

LOOP
        BRA         LOOP                ; indefinite loop

END
```
"C"
"68000"
$EXTENSIONS ON$
$ASM_FILE$
$FAR ON$
$INIT_ZEROES OFF$

/*
 This file contains all addressing for the hardware devices.
*/

/*
 MC146818 Real-Time Clock address map
*/

$ORG 040000H$
int SECOND;
int SEC_ALARM;
int MINUTE;
int MIN_ALARM;
int HOUR;
int HR_ALARM;
int DAY_WEEK;
int DATE;
int MONTH;
int YEAR;
int REG_A;
int REG_B;
int REG_C;
int REG_D;
$END_ORG$ /*
 Display address map
*/

$ORG 044020H$
int SYS_DISPLAY;
$END_ORG$
$ORG 044026H$
int DIA_DISPLAY;
$END_ORG$
$ORG 04402CH$
int HR_DISPLAY;
$END_ORG$
$ORG 044032H$
int PRP_DISPLAY;
$END_ORG$
$ORG 04403AH$
int ELAPSED_DISPLAY;
$END_ORG$ /*
 Front panel controls
*/

```
$ORG 044044H$ int ALARM_LED;
int SWITCH_LED;
int SWITCH_BUFFER;

$END_ORG$

/*
 Interval time access and stop/start interrupt status
*/

$ORG 04404AH$
int INTERVAL_MIN;
unsigned short SS_INT_STATUS;
unsigned short INTERVAL_SEC;
$END_ORG$ /*
 Heart Rate on/off switch
*/

$ORG 04404DH$
unsigned short HR_SWITCH;

/*
 K-Sound or Oscillometric LED change
*/

$ORG 04404EH$
int DUAL_LED;
$END_ORG$

/*
 MC6840 Programmable Timer Module address map
*/

$ORG 048010H$
int TIMER1_3_CNTRL_REG;
int TIMER2_CNTRL_REG;
int MSB1_BUFFER;
int TIMER1_LATCH;
int MSB2_BUFFER;
int TIMER2_LATCH;
int MSB3_BUFFER;
int TIMER3_LATCH;
$END_ORG$ /*
 MC6850 Asynchronous Communications Interface Adapter (ACIA) #1
*/

$ORG 04C000H$
int ACIA1_CNTRL_STAT_REG;
int ACIA1_TRNSMT_RECEIVE_REG;
$END_ORG$

/*
 MC68488 General Purpose Interface Adaptor (GPIA)
*/

$ORG 050000H$
int INT_MASK_REG;
$END_ORG$

/*
 Multiplexer analog channel select and filter test control
*/
```

```
$ORG 054000H$
int MULTIPLEXER;
$END_ORG$

/*
 A/D Converted Data
*/

$ORG 058000H$
int AD_CONVERSION;
$END_ORG$

/*
 MC6850 Asynchronous Communications Interface Adapter (ACIA) #2
*/

$ORG 05C000H$
int ACIA2_CNTRL_STAT_REG;
int ACIA2_TRNSMT_RECEIVE_REG;
$END_ORG$

/*
 Miscellaneous I/O control
 Includes dump valve, pump enable, A/D conversion and attenuator control
*/

$ORG 060000H$
int IO_CONTROL;
$END_ORG$

/*
 ECG control of test circuitry, lead selection, float reset and ECG
 interrupt reset.
 Bleed valve opening control
*/

$ORG 064000H$
unsigned short ECG_CONTROL;
unsigned short BLEED_VALVE;
$END_ORG$

/*
 ECG status of pending interrupts and floating leads
*/

$ORG 068000H$
int ECG_STATUS_BUFFER;
$END_ORG$
"C"
"68000"
$EXTENSIONS ON$
$ASM_FILE$
$FAR ON$
$INIT_ZEROES OFF$ /*
 This file contains all RAM global variables
*/ short ABORT2,                   /* flag-abort2 successful recovery */

ABORT3,                   /* flag-abort3 needs processing    */

ALARM_ON,                 /* flag-tone alarm on              */

ARRHYTHMIA,               /* flag-arrhythmia condition was
                                        detected by ECG interrupt
                                        handler                    */
```

| | |
|---|---|
| AVERAGE_HR_DISPLAYED, | /* flag-final Heart Rate displayed don't display intermediate Heart Rates */ |
| BAD[3], | /* summary table denoting last three trigger lead selections were bad */ |
| BLEED_PROCESS_FINISHED, | /* flag-cuff is depressurized */ |
| BLEED_RATE_ESTABLISHED, | /* flag-change in cuff pressure has met bleed rate twice in succession */ |
| CLOCK_RUNNING, | /* flag-elapsed time is updated */ |
| DATA_OK, | /* flag-A/D conversion is valid */ |
| DATASET_COMPLETE, | /* */ |
| DELAY, | /* flag-lead selection delay of 50 ms (required after switching leads) is activated */ |
| DELAY_TIME, | /* time in ms since lead selection delay was activated after switching leads */ |
| DIAGNOSTIC_SELFTEST, | /* flag-diagnostic self-test mode */ |
| ecg_control, | /* read/write equivalent of "ECG_CONTROL" */ |
| ELAPSED_MIN1, | /* minute digit of elapsed time */ |
| ELAPSED_MIN2, | /* minute x 10 digit of elapsed time */ |
| ELAPSED_SEC1, | /* second digit of elapsed time */ |
| ELAPSED_SEC2, | /* second x 10 digit of elapsed time */ |
| ERROR_CONDITION, | /* flag-error condition occurred */ |
| EXEC_WAS_PREVIOUS_MODE, | /* flag-previous STBPM operation was the Exercise mode */ |
| FAILED_SELFTEST, | /* flag-STBPM failed self-test sequence */ |
| FIRST_BLEED, | /* flag-first time in "bleed" routine */ |
| FIRST_ECG, | /* flag-first ECG of the measurement cycle */ |
| FIRST_TIME, | /* flag-first time entering this mode */ |
| GOOD_REST_DATA, | /* flag-a valid Rest measurement cycle was completed */ |
| IN_CAL_CUFFP, | /* flag-in "cal_cuffp" routine */ |
| IN_PUMP, | /* flag-in "pump" routine */ |
| IN_SECOND_DELAY, | /* flag-in "second_delay" routine */ |

```
INITIAL_BLEED,              /* flag-first bleed attempt of the
                               Rest mode                       */

INTERVAL_UP,                /* flag-the interval time between
                               measurement cycles is up        */

K,                          /* the number of times the bleed
                               has matched the change in cuff
                               pressure in succession          */

LEAD_MONITORING,            /* current lead monitoring during
                               lead selection                  */

LEAD_PROGRESS,              /* what point lead selection
                               processing is at                */

LEAD_SELECTION_COMPLETE,    /* trigger lead was selected three
                               times in succession             */

LEAD_STATUS,                /* flag-new lead to be monitored   */

LEADS_PROCESSED,            /* total number of lead selection
                               cycles was completed            */

LEAD1[3],                   /* summary table denoting last three
                               trigger lead selections were for
                               lead I                          */

LEAD2[3],                   /* summary table denoting last three
                               trigger lead selections were for
                               lead II                         */

LEAD3[3],                   /* summary table denoting last three
                               trigger lead selections were for
                               lead III                        */

MANUAL_OLD_STATE,           /* flag-for key debouncing a 0 to 1
                               transition must be seen at
                               the switch buffer to denote
                               a valid user selection of
                               the MANUAL key                  */

MEASUREMENT_COMPLETE,       /* flag-processing finished by the
                               "process" routine. Blood
                               pressure measurements have
                               been taken                      */

MODE_IS_EXEC,               /* flag-current STBPM operation is
                               the Exercise mode               */

MODE_IS_HALT,               /* flag-current STBPM operation is
                               the Halt mode                   */

MODE_IS_MANUAL,             /* flag-current STBPM operation is
                               the Manual mode                 */

MODE_IS_MODIFY,             /* flag-current STBPM operation is
                               the Modify mode                 */

MODE_IS_PROGRAM,            /* flag-current STBPM operation is
                               the Programming mode            */

MODE_IS_REST,               /* flag-current STBPM operation is
                               the Rest mode                   */

MODE_IS_SELFTEST,           /* flag-current STBPM operation is
                               the Self-test mode              */
```

```
MODE_IS_STANDBY,              /* flag-current STBPM operation is
                                 the Standby mode              */

MODE_IS_START,                /* flag-current STBPM operation is
                                 the Run mode                  */

MODE_IS_STOP,                 /* flag-current STBPM operation is
                                 the Stop mode                 */

MODE_TRANSITION,              /* flag-a mode transition was seen */

NO_ECG_FOUND,                 /* flag-no ECG trigger has been seen
                                 for the past two seconds      */

NULL,                         /* flag-remove leading blanks from
                                 displayed values (default)    */

PI_DI_AMP_AVG_COMPLETE,       /* flag-first pi and di amplitude
                                 average calculated            */

PIR_DETECTED,                 /* flag-periodic interrupt occurred*/

PREVIOUS_ERROR_CONDITION,     /* flag-previous error condition */

PROCESSING_LEAD_SELECTION,    /* flag-the 12 position switch has
                                 been programmed to allow the
                                 system software to select the
                                 ECG trigger lead              */

PROGRAMMED_MAX_CUFF,          /* flag-use new programmed max cuff
                                 value when pumping up the
                                 cuff                          */
REST_EXEC_OLD_STATE,          /* flag-for key debouncing a 0 to 1
                                 transition must be seen at
                                 the switch buffer to denote
                                 a valid user selection of
                                 the REST/EXER key             */

REST_MODE_STATUS,             /* flag-"remembers" last state of
                                 REST/EXER LED                 */

SAMPLING_PI_DI,               /* flag-signals Real-Time Clock
                                 interrupt to sample the pi &
                                 di channels and calculate an
                                 average amplitude for each    */

SELFTEST_OLD_STATE,           /* flag-for key debouncing a 0 to 1
                                 transition must be seen at
                                 the switch buffer to denote
                                 a valid user selection of
                                 the SELF TEST key             */

SHOW_TIME,                    /* enables the updating of the elapsed
                                 time displays; it has no effect
                                 on the operation of elapsed time
                                 itself, only on the display   */

STATUS_OF_LEAD_SELECTION_PROCESSING;
                              /* flag-system software is processing
                                 the lead selection            */ unsigned short I;             /* index to summary table for lead
                                 selection                     */ int alarm_led,                /* read/write equivalent of
                                 ALARM_LED                     */
```

```
BLEED_CRACK_POINT,        /* bleed valve opening value used to
                             start the bleed process          */

BLEED_DOWN,               /* contains cuff depressurization
                             value                            */

CUFF[2000],               /* cyclic array of cuff pressure
                             values used for blood pressure
                             measurements                     */

CUFFP_OFFSET,             /*                                  */

DI_AMP[1002],             /* array containing di amplitudes
                             used to record an average di
                             amplitude between measurement
                             cycles                           */

DI_ATTEN,                 /* read/write current distal atten-
                             uator setting                    */

DI_COUNT,                 /* number of di amplitude samples
                             recorded for use in determining an
                             average di amplitude             */

DIASTOLIC,                /* final Diastolic pressure reading
                             visible to the user at the
                             DIASTOLIC display                */

DIST[2000],               /* cyclic array of distal amplitudes
                             used for blood pressure
                             measurements                     */

ECG[2000],                /* cyclic array of ECG triggers. A
                             "1" indicates an ECG trigger; a
                             "0" indicates no ECG trigger     */

ELAPSED_TIME,             /* current elapsed time visible to
                             user at the ELAPSED TIME display */

HEART_RATE,               /* final Heart Rate displayed at the
                             HEART RATE display               */ io_control,               /* read/write equivalent to
                             "IO_CONTROL"                     */

INTERVAL_END,             /* interval end time as set by the
                             user at the INTERVAL TIME thumb-
                             wheels                           */

LAST_CUFF_PRESSURE,       /* last cuff pressure sampled       */

LEAD,                     /* flag-signals current selection by
                             user of the 12 position switch
                             previously defined as N/A        */

LEAD1_AMP[2000],          /* array containing lead I raw peak
                             data                             */

LEAD2_AMP[2000],          /* array containing lead II raw peak
                             data                             */

LEAD3_AMP[2000],          /* array containing lead III raw peak
                             data                             */

MAX_AMPLITUDE,            /*                                  */

MAX_CUFF,                 /* 12 position switch current value
                             of the MAXIMUM CUFF PRESSURE     */
```

| | |
|---|---|
| MAX_DIASTOLIC, | /* 12 position switch current value of the MAXIMUM DIASTOLIC */ |
| MAX_HEART, | /* 12 position switch current value of the MAXIMUM HEART RATE */ |
| MAX_MMHG, | /* 12 position switch current value of the MAXIMUM CUFF PRESSURE */ |
| MAX_POSITION, | /* */ |
| MAX_SYSTOLIC, | /* 12 position switch current value of the MAXIMUM SYSTOLIC */ |
| multiplexer, | /* read/write equivalent of "MULTIPLEXER" */ |
| PI_AMP[1002], | /* array containing pi amplitudes used to record an average pi amplitude between measurement cycles */ |
| PI_ATTEN, | /* read/write current proximal attenuator setting */ |
| PI_COUNT, | /* number of pi amplitude samples recorded for use in determining an average pi amplitude */ |
| PROX[2000], | /* cyclic array of proximal amplitudes used for blood pressure measurements */ |
| PUMP_UP, | /* contains cuff pressurization value */ |
| SAMPLE_INDEX, | /* pi and di array indexes used when determining average amplitude*/ |
| SAMPLE_TIME, | /* time spent sampling pi and di channels when determing average amplitudes */ |
| SEC_COUNT, | /* flag-current number of seconds that have gone by since resetting this flag */ |
| SECOND_BEST, | /* contains the secondary choice for trigger lead selection */ |
| SELECTION, | /* flag-shows valid user selections*/ |
| SIZE, | /* programmable array size for data acquisition. Set at containing 2 seconds worth of data */ |
| SYSTOLIC, | /* final Systolic pressure reading visible to the user at the SYSTOLIC display */ |
| switch_led, | /* read_write equivalent of "SWITCH_LED" */ |
| timer1_3_cntrl_reg, | /* read/write equivalent of "TIMER1_3_CONTRL_REG" */ |
| timer2_cntrl_reg, | /* read/write equivalent of "TIMER2_CONTRL_REG" */ |

```
       TRIGGER_LEAD;                    /* ECG trigger lead configuration  */ unsigned int bleed_valve,               /* read/write equivalent of
                                           "BLEED_VALVE"                   */

RAW_DATA_POSITION;         /* index to cyclic data acquisition
                                           arrays.                         */ unsigned long CURRENT_INT_TIME,         /* current time between pulses in
                                           milliseconds                    */

ECG_PULSE_COUNT,          /* number of ECG triggers seen in
                                           current measurement cycle       */

HR_COUNT,                 /* number of valid non-arrhythmia
                                           ECG tigger's for use in calculat-
                                           ing the final Heart Rate        */

PREVIOUS_INT_TIME;        /* previous time between pulses in
                                           milliseconds                    */ float AVG_DI_AMP,                       /* di average amplitude            */

AVG_DI_ARRAY[10],                 /* array of 10 most recent AVG_DI_AMP
                                           values.                         */

AVG_MAX_AMPLITUDE,                /* average maximum amplitude       */

AVG_PI_AMP,                       /* pi average amplitude            */

AVG_PI_ARRAY[10],                 /* array of 10 most recent AVG_PI_AMP
                                           values.                         */

LEAD1_SIGNAL_NOISE_RATIO,         /* signal-to-noise ratio for lead I
                                           lead I                          */

LEAD2_SIGNAL_NOISE_RATIO,         /* signal-to-noise ratio for
                                           lead II                         */

LEAD3_SIGNAL_NOISE_RATIO,         /* signal-to-noise ratio for
                                           lead III                        */

SUM_DI_AMP,                       /* sum of the elements in
                                           AVG_PI_ARRAY                    */

SUM_PI_AMP;                       /* sum of the elements in
                                           AVG_PI_ARRAY                    */

"68000"

;Exception processing vector assignment

EXTERNAL start,BUS_ERROR,ADDR_ERROR,INSTR_ERROR,DIV_ERROR,OVFL_ERROR
    EXTERNAL TRAPV_ERROR,TRACE_ACT,EM_1010,EM_1111,RES_1,RES_2,RES_3
    EXTERNAL PRIV_ERROR
    EXTERNAL acia_interrupt,gpia_interrupt,real_time_clock_interrupt
    EXTERNAL programmable_timer_interrupt,stop_start_interrupt,ecg_interrupt
    EXTERNAL MONITOR_ENTRY ORG 0
    DC.L   26FFEH                       ;Reset: initial supervisor stack
                                        ;          pointer
    DC.L   start                        ;Reset: initial program counter
;ORG 8
    DC.L   BUS_ERROR                    ;Bus error vector
```

```
;ORG 0CH
   DC.L   ADDR_ERROR                        ;Address error vector

;ORG 10H
   DC.L   INSTR_ERROR                       ;Illegal instruction vector ;ORG 14H
   DC.L   DIV_ERROR                         ;Zero divide ;ORG 18H
   DC.L   OVFL_ERROR                        ;CHK instruction ;ORG 1CH
   DC.L   TRAPV_ERROR                       ;TRAPV instruction ;ORG 20H
   DC.L   PRIV_ERROR                        ;Privileged violation vector ;ORG 24H
   DC.L   TRACE_ACT                         ;Trace vector ;ORG 28H
   DC.L   EM_1010                           ;Line 1010 emulator ;ORG 2CH
   DC.L   EM_1111                           ;Line 1111 emulator ;ORG 30H
   DC.L   RES_1                             ;Unassigned,reserved #1

;ORG 34H
   DC.L   RES_2                             ;Unassigned,reserved #2

;ORG 38H
   DC.L   RES_3                             ;unassigned,reserved #3

ORG 64H
   DC.L   gpia_interrupt                    ;Level 1 interrupt autovector ORG 68H
   DC.L   acia_interrupt                    ;Level 2 interrupt autovector
 ORG 6CH
   DC.L   programmable_timer_interrupt      ;Level 3 interrupt autovector ORG 70H
   DC.L   ecg_interrupt                     ;Level 5 interrupt autovector ORG 74H
   DC.L   real_time_clock_interrupt         ;Level 4 interrupt autovector ORG 78H
   DC.L   stop_start_interrupt              ;Level 6 interrupt autovector ORG 80H
   DC.L   MONITOR_ENTRY                     ;TRAP instruction vector
/*
The following defined constants are used throughout the system software:
*/

/*
Logical
*/ define YES 1
define NO 0
#define TRUE 1
```

```
#define FALSE 0
#define PASS 1
#define FAIL 0

/*
 Masks
*/ define LEVEL0_INTERRUPT  0F8FFH
define LEVEL4_INTERRUPT  0400H
#define HIGH_BYTE_MASK    0FF00H
#define LOW_BYTE_MASK     0FFH
#define SWITCH_MASK       0FH
#define HIGH_BIT_MASK     0F0H
define LOW_BIT_MASK      0FH /*
 Multiplexer channels and analog filter test control
*/ define DISTAL_SENSOR 00H
define PROXIMAL_SENSOR 01H
#define CUFF_PRESSURE 02H
#define OSCIL_CUFF_PRESSURE 03H
#define ECG_LEAD1_PEAK 04H
#define ECG_LEAD2_PEAK 05H
#define ECG_LEAD3_PEAK 06H
#define PLUS_5V 07H
#define PLUS_15V 08H
#define MINUS_15V 09H
#define MINUS_5V 0AH
#define ANALOG_GROUND 0BH
#define DIGITAL_GROUND 0CH
#define ECG_LEAD1_RAW 0DH
#define ECG_LEAD2_RAW 0EH
#define ECG_LEAD3_RAW 0FH
#define ENABLE_ANALOG_FILTER_TEST 0EFH
#define DISABLE_ANALOG_FILTER_TEST 10H
define CLEAR_MUX_CHANNEL 0F0H /*
 ECG status buffer
*/ define FLOATING 07H
define ECG_LEAD1_FLOATING 04H
#define ECG_LEAD2_FLOATING 02H
#define ECG_LEAD3_FLOATING 01H
#define ECG_INTERRUPT_PENDING 08H
define ECG_LEADS 07H /*
 ECG control
*/ define DISABLE_ECG_TESTS 70H
define CLEAR_LEAD_SELECTION 0F3H
#define ECG_LEAD1 00H
#define ECG_LEAD2 04H
#define ECG_LEAD3 08H
#define FLOAT_RESET_HIGH 02H
#define FLOAT_RESET_LOW 0FDH
#define ENABLE_ECG_INT 01H
define DISABLE_ECG_INT 0FEH /*
 Bleed valve control
*/
```

```
#define BLEED_VALVE_OPEN 00H
#define BLEED_VALVE_CLOSED 0FFH

/*
 Miscellaneous I/O control
*/ define DUMP_VALVE_OPEN 7FFFH
define DUMP_VALVE_CLOSED 8000H
#define PUMP_ON 0DFFFH
#define PUMP_OFF 2000H
#define LOAD_PROXIMAL_ATTEN 0400H
#define DISABLE_PROXIMAL_ATTEN 0FBFFH
#define LOAD_DISTAL_ATTEN 0200H
#define DISABLE_DISTAL_ATTEN 0FDFFH
#define SET_ATTEN_0db 0FE00H
#define SET_ATTEN_10db 0100H
#define SET_ATTEN_19_9db 0F999H
#define AD_READ 0800H
define AD_START 0F7FFH /*
 Programmable parameter's selection range and incrementation values
*/ define SYSMAX   300
define SYSMIN   120
#define SYSINC   10
#define DIAMAX   180
#define DIAMIN   80
#define DIAINC   10
#define CUFMIN   100
#define CUFMAX   300
#define CUFINC   10
#define MHGMAX   50
#define MHGMIN   0
#define MHGINC   5
#define HRTMAX   250
#define HRTMIN   40
#define HRTINC   10

/*
 Real-Time Clock
*/ define REAL_TIME_CLOCK_INT_PENDING 80H
define UPDATE_CYCLE_IN_PROGRESS 80H
#define RESUME_UPDATE_CYCLE 07FH
#define STOP_UPDATE_CYCLE 80H
#define TIME_BASE_4_194304MHz 00H
#define SELECT_4_194304MHz_TIME_BASE 8FH
#define RESET_DIVIDER_CHAIN 70H
#define BINARY_MODE 04H
#define HOUR_24 02H
#define DAYLIGHT_SAVINGS_TIME 01H
#define DIVIDER_SELECTION_BITS 70H
define RTC_DONT_CARE_CODE 0FFH /*
 Real-Time Clock update ended interrupt controls
*/ define DISABLE_UIE 0EFH
define ENABLE_UIE 10H
#define UF_MASK 10H
#define UIE_MASK 10H
```

```
/*
 Real-Time Clock periodic interrupt controls
*/ define PIR_500 0FH
define PIR_250 0EH
#define PIR_125 0DH
#define PIR_063 0CH
#define PIR_04 08H
#define PIR_02 07H
#define PIR_01 06H
#define DISABLE_PIR 0F0H
#define ENABLE_PIE 40H
#define DISABLE_PIE 0BFH
#define PF_MASK 40H
define PIE_MASK 40H /*
 Real-time Clock alarm interrupt controls
*/ define ENABLE_AIE 20H
define DISABLE_AIE 0DFH
#define AF_MASK 20H
define AIE_MASK 20H /*
 Switch LED's
*/ define OSCIL_LED_ON 80H
define OSCIL_LED_OFF 7FH
#define LAMP_TEST_ON 0DFH
#define LAMP_TEST_OFF 20H
#define SWITCH_LEDS_ON 1FH
#define SWITCH_LEDS_OFF 0E0H
#define STOP_LED_OFF 0FEH
#define STOP_LED_ON  01H
#define START_LED_OFF 0FDH
#define START_LED_ON 02H
#define ENABLE_SS_INT 40H
#define DISABLE_SS_INT 0BFH
#define SS_INT_PENDING 10H
#define REST_LED_OFF 0FBH
#define REST_LED_ON  04H
#define EXEC_LED_OFF 0F7H
#define EXEC_LED_ON  08H
#define MANUAL_LED_OFF 0EFH
define MANUAL_LED_ON  10H /*
 Switch buffer
*/ define SELFTEST_DEPRESSED 80H
define REST_EXEC_DEPRESSED 40H
#define MANUAL_DEPRESSED   20H
define MODIFY_DEPRESSED   10H /*
 Heart rate on/off switch
*/ define HR_SWITCH_ON 20H

/*
 Alarm LED's
*/
```

```
#define ALARM_LEDS_ON 1FH
#define ALARM_LEDS_OFF 0E0H
#define TONE_ALARM_ON 20H
#define TONE_ALARM_OFF 0DFH
#define ECG_LED_ON 10H
#define ECG_LED_OFF 0EFH
#define HR_LED_ON 08H
#define HR_LED_OFF 0F7H
#define DIAS_LED_ON 04H
#define DIAS_LED_OFF 0FBH
#define SYS_LED_ON 02H
#define SYS_LED_OFF 0FDH
#define ARR_LED_ON 01H
define ARR_LED_OFF 0FEH /*
 GPIA control
*/ define DISABLE_GPIA_INT 00H

/*
 ACIA control
*/ define MASTER_RESET 03H
define CLOCK_DIVIDE_RATIO_16 01H
#define B7_EVEN_1_STOP 08H
#define B8_EVEN_1_STOP 18H
#define DISABLE_ACIA_RX_INT 7FH
define DISABLE_ACIA_TX_INT 9FH /*
 Programmable timer control
*/ define SELECT_PT1 01H
define SELECT_PT3 0FEH
#define PT3_TIME_OUT 04H
#define CONTINOUS_OPERATING_MODE 0C7H
#define PRESCALE_8 01H
#define ALL_TIMERS_OPERATIVE 0FEH
#define ALL_TIMERS_INOPERATIVE 01H
#define ENABLE_CLOCK 02H
#define COUNTING_MODE_16_BIT 0FBH
#define DISABLE_PT_INT 9FH
#define ENABLE_PT_INT 60H
#define DISABLE_PT_OUTPUT 7FH
define ENABLE_PT_OUTPUT 80H /*
 A/D converted data control
*/ define AD_DATA_MASK 0FFFH
define AD_DATA_NOT_READY 8000H
#define AD_DATA_NEGATIVE_MASK 0F800H
#define AD_DATA_POSITIVE_MASK 7FFH
define AD_DATA_SIGN_BIT 800H /*
 ASCII data
*/ define ASCII_MASK 30H
define BLANK 20H
#define COLON 3AH
#define PERIOD 2EH
#define ZERO 30H
```

```
/*
 Lead selection routine
*/ define AUTOMATIC_LEAD_SELECTION 04
define BAD_LEAD 99

/*
 Programming mode
*/ define YEAR_SETTING 85
define selftest  8000H
#define restexec  4000H
#define manual    2000H
#define modify    1000H
#define off       0800H
#define systolic  0400H
#define diastolic 0200H
#define heart     0100H
#define mmhg      0080H
#define cuff      0040H
#define month     0020H
#define date      0010H
#define year      0008H
#define hour      0004H
#define minute    0002H
define unassigned  0001H /*
 Processing routine
*/ define ONE_SEC 1000
define TWO_SEC 2000
#define FIVE_SEC 5000
#define FORTY_mmHg 355
#define FIVE_mmHg 44
#define THREE_mmHg 27
#define SAMPLE_INTERVAL  2         /* milliseconds */
#define ECG_THRESHOLD  1
#define MEDIAN_FILTER_WIDTH  3
#define MAX_PULSES  100
#define HR_SAMPLE 6
#define PULSE_SAMPLE 3

/*
 Macro's
*/ define convert(data) ((((data & 0FFFH) * .002441406) - 5.0))
define square_wave_output(frequency) (((400000 / frequency) -1))

/*
  CUFFP_CONV = 300 mmHg / ((6.5) / 10) * 4096)
             = mmHg /((voltage range / maximum volts)*largest digital value)
*/ define CUFFP_CONV  0.112680288
define AVG_COUNT 5
#define PUMP_OFFSET 89
```

What is claimed is:

1. A blood pressure monitoring system for measuring blood pressure during stress testing or other physical activity, said blood pressure monitoring system comprising:
an inflatable cuff adapted to encircle a patient's arm;
means for inflating and deflating said inflatable cuff within a selected range of pressures;
pressure transducer means responsive to cuff pressure and having an output signal indicative thereof;
audio transducer means for detecting pulse sounds at said inflatable cuff;
a plurality of electrocardiographic leads, each coupling an electrocardiographic signal from said patient; and
controller means comprising:
trigger signal generation means coupled to said plurality of electrocardiographic leads for periodically measuring the amount of noise present on each of said plurality of electrocardiographic leads and for selecting a particular lead having the least amount of noise to be utilized as a trigger signal; and
measurement means for obtaining a measure of systolic and diastolic blood pressure from said pulse sounds at selected cuff pressures in response to said trigger signal.

2. The blood pressure monitoring system according to claim 1 wherein said means for inflating and deflating said inflatable cuff comprises at least one electric air pump and a controllable deflation valve.

3. The blood pressure monitoring system according to claim 1 wherein said controllable deflation valve deflates and inflatable cuff at a rate of between 3 mmHg and 5 mmHg per heartbeat.

4. The blood pressure monitoring system according to claim 1 wherein said plurality of electrocardiographic Leads comprises three electrocardiographic Leads.

5. The blood pressure monitoring system according to claim 1 wherein said controller means comprises an appropriately programmed microprocessor.

6. The blood pressure monitoring system according to claim 1 wherein said trigger signal generation means further includes means for detecting the presence or absence of an electrocardiographic signal and wherein loss of said signal from said particular Lead will cause a second Lead to be utilized for trigger signal generation.

7. The blood pressure monitoring system according to claim 1 wherein said trigger signal generation means periodically measures the amount of 60 Hertz noise on each of said plurality of electrocardiographic Leads.

8. A blood pressure monitoring system from measuring blood pressure during stress testing or other physical activity, said blood pressure monitoring system comprising:
an inflatable cuff adapted to encircle a patient's arm;
means for inflating and inflatable cuff;
means for deflating said inflatable cuff at a selectable rate;
pressure transducer means responsive to cuff pressure and having an output signal indicative thereof;
audio transducer means for detecting pulse sounds at said inflatable cuff;
a plurality of electrocardiographic Leads, each coupling an electrocardiographic signal from said patient; and
controller means comprising:
trigger signal generation means coupled to said plurality of electrocardiographic Leads for periodically measuring the amount of noise present on each of said plurality of electrocardiographic Leads and for selecting a particular Lead having the least amount of noise to be utilized as a trigger signal;
deflation control means for selecting said selectable rate of deflation in response to said trigger signal wherein said deflation rate is controlled by said patient's heart rate whereby maximum accuracy of blood measurement may be obtained; and
measurement means for obtaining a measure of systolic and diastolic blood pressure from said pulse sounds to selected cuff pressures in response to said trigger signal.

9. The blood pressure monitoring system according to claim 8 wherein said deflation control means also includes means for selecting a maximum permissible deflation rate whereby a minimum measurement times may be utilized.

10. The blood pressure monitoring system according to claim 8 wherein said means for inflating said inflatable cuff comprises at least one electric air pump.

11. The blood pressure monitoring system according to claim 8 wherein said means for deflating said inflatable cuff at a selectable rate comprises a controllable deflation valve.

12. The blood pressure monitoring system according to claim 8 wherein said plurality of electrocardiographic Leads comprises three electrocardiographic Leads.

13. The blood pressure monitoring system according to claim 8 wherein said controller means comprises an appropriately programmed microprocessor.

14. The blood pressure monitoring system according to claim 8 wherein said trigger signal generation means further includes means for detecting the presence or absence of an electrocardiographic signal and wherein said loss of said signal from said particular Lead will cause a second Lead to be utilized for trigger signal generation.

15. The blood pressure monitoring system according to claim 8 wherein said trigger signal generation means periodically measures the amount of 60 Hertz noise on each of said plurality of electrocardiographic Leads.

16. A blood pressure monitoring system for measuring blood pressure during stress testing or other physical activity, said blood pressure monitoring system comprising:
an inflatable cuff adapted to encircle a patient's arm;
means for inflating said inflatable cuff to a selectable pressure;
means for deflating said inflatable cuff;
pressure transducer means responsive to cuff pressure and having an output signal indicative thereof;
audio transducer means for detecting pulse sounds at said inflatable cuff;
a plurality of electrocardiographic Leads, each coupling an electrocardiographic signal from said patient; and
controller means comprising:
trigger signal generation means coupled to said plurality of electrocardiographic Leads for periodically measuring the amount of noise present on each of said plurality of electrocardiographic Leads and for selecting a particular Lead having the least amount of noise to be utilized as a trigger signal;

measurement means for obtaining a measure of systolic and diastolic blood pressure from said pulse sounds at selected cuff pressures in response to said trigger signal; and inflation control means for controlling inflation of said inflatable cuff to a selectable pressure which is based upon said measured systolic blood pressure.

17. The blood pressure monitoring system according to claim 16 wherein said means for inflating said inflatable cuff to a selectable pressure comprises at least one electric air pump.

18. The blood pressure monitoring system according to claim 16 wherein said means for deflating said deflatable cuff includes means for deflating said inflatable cuff at a selectable deflation rate.

19. The blood pressure monitoring system according to claim 18 further including deflation control means coupled to said trigger signal generation means for selecting said selectable deflation rate in response to said trigger signal wherein said deflation rate is controlled by said patient's heart rate whereby maximum accuracy of blood pressure measurement may be obtained.

20. The blood pressure monitoring system according to claim 16 wherein said plurality of electrocardiographic Leads comprises three electrocardiographic Leads.

21. The blood pressure monitoring system according to claim 16 wherein said controller means comprises an appropriately programmed microprocessor.

22. The blood pressure monitoring system according to claim 16 wherein said trigger signal generation means further includes means for detecting the presence or absence of an electrocardiographic signal and wherein loss of said signal from said particular Lead will cause a second Lead to be utilized for trigger signal generation.

23. A blood pressure monitoring system, comprising:
an inflatable cuff adapted to encircle a patient's arm, said inflatable cuff having a proximal edge disposed toward said patient's shoulder and a distal edge disposed toward said patient's elbow;
means for inflating and deflating said inflatable cuff within a selected range of pressures;
pressure transducer means responsive to cuff pressure and having an output signal indicative thereof;
proximal audio transducer means for detecting pulse sounds at said proximal edge of said inflatable cuff and for generating an output signal indicative thereof;
distal audio transducer means for detecting pulse sounds at said distal edge of said inflatable cuff and for generating an output signal indicative thereof; and, controller means comprising:
amplitude measurement means coupled to said distal audio transducer means and said pressure transducer means for measuring the amplitude of pulse sound detected at said distal audio transducer means at selected cuff pressures;
time delay measurement means coupled to said distal audio transducer means, said proximal audio transducer means and said pressure transducer means for measuring the time delay between a pulse sound detected at said proximal audio transducer means and said pulse sound detected at said distal audio transducer means at selected cuff pressures; and,
processing means for multiplying the amplitude of pulse sound detected at said distal audio transducer means by said time delay between said pulse sound detected at said proximal audio transducer means and said pulse sound detected at said distal audio transducer means at each of said selected cuff pressures to obtain a measurement of systolic and diastolic blood pressure therefrom.

24. The blood pressure monitoring system according to claim 23 wherein said means for inflating and deflating said inflatable cuff comprises at least one electric air pump and a controllable deflation valve.

25. The blood pressure monitoring system according to claim 23 wherein said controllable deflation valve deflates said inflatable cuff at a rate of between 3 mmHg and 5 mmHg per heartbeat.

26. The blood pressure monitoring system according to claim 23 wherein said proximal audio transducer and said distal audio transducer comprise microphones for converting audio inputs to an electrical output signal.

27. The blood pressure monitoring system as claimed in claim 23, including:
a plurality of electrocardiograph Leads, each coupling an electrocardiographic signal from said patient;
and said controller means includes trigger signal generation means coupled to said plurality of electrocardiographic Leads for periodically measuring the amount of noise present on each of said plurality of electrocardiograph Leads and for selecting a particular Lead having the least amount of noise to be utilized as a trigger signal, wherein said amplitude measurement means and said time delay measurement means operate in response to said trigger signal, and filter means coupled to said processing means for filtering the product resultant from multiplying the amplitude by the time delay.

28. The blood pressure monitoring system according to claim 27 wherein said plurality of electrocardiographic Leads comprise three electrocardiographic Leads.

29. The blood pressure monitoring system according to claim 27 wherein said controller means comprises an appropriately programmed microprocessor.

30. The blood pressure monitoring system according to claim 27 wherein said trigger signal generation means further includes means for detecting the presence or absence of an electrocardiographic signal and wherein the loss of said signal from said particular Lead will cause a second Lead to be utilized for trigger signal generation.

31. The blood pressure monitoring system according to claim 27 wherein said trigger signal generation means periodically measures the amount of 60 Hertz noise on each of said plurality of electrocardiographic Leads.

32. The blood pressure monitoring system according to claim 27 wherein said filter means includes means for performing statistical analysis of said resultant product to obtain a more accurate measure of systolic and diastolic blood pressure.

33. A method of obtaining accurate blood pressure measurement comprising the steps of:
placing an inflatable cuff around the arm of a patient;
inflating said inflatable cuff to a selected pressure;
slowing deflating said inflatable cuff;
measuring the amplitude of pulse sounds above and below said inflatable cuff at selected cuff pressures;
measuring the time delay between each pulse sound above said inflatable cuff and said pulse sound below said inflatable cuff at selected cuff pressures; and multiplying said amplitude of said pulse sound below said inflatable cuff at selected cuff pressures by said time delay between said pulse sound above said inflatable cuff and said pulse sound below said inflatable cuff at said selected cuff pressures to obtain a measure of systolic and diastolic blood pressure.

34. The method as claimed in claim 33, including the step of filtering the product resultant from said multiplying step.

* * * * *